US012637464B2

(12) United States Patent
Olson et al.

(10) Patent No.: US 12,637,464 B2
(45) Date of Patent: May 26, 2026

(54) TETRACYCLIC COMPOUNDS FOR TREATING BRAIN DISORDERS

(71) Applicant: The Regents of the University of California, Oakland, CA (US)

(72) Inventors: David E. Olson, Oakland, CA (US); Jeremy R. Tuck, Oakland, CA (US); Lee E. Dunlap, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 324 days.

(21) Appl. No.: 18/554,762

(22) PCT Filed: Apr. 13, 2022

(86) PCT No.: PCT/US2022/024626
§ 371 (c)(1),
(2) Date: Oct. 10, 2023

(87) PCT Pub. No.: WO2022/221415
PCT Pub. Date: Oct. 20, 2022

(65) Prior Publication Data
US 2024/0208973 A1      Jun. 27, 2024

Related U.S. Application Data

(60) Provisional application No. 63/174,266, filed on Apr. 13, 2021.

(51) Int. Cl.
| | |
|---|---|
| *C07D 471/18* | (2006.01) |
| *A61K 31/4748* | (2006.01) |
| *A61P 25/00* | (2006.01) |
| *C07D 471/14* | (2006.01) |

(52) U.S. Cl.
CPC ............ *C07D 471/14* (2013.01); *A61P 25/00* (2018.01)

(58) Field of Classification Search
CPC C07D 471/18; C07D 471/04; A61K 31/4748; A61P 25/00
USPC ............................................ 546/66; 514/288
See application file for complete search history.

(56) References Cited

U.S. PATENT DOCUMENTS

| | | | |
|---|---|---|---|
| 3,525,750 A | 8/1970 | Renner | |
| 3,553,232 A | 1/1971 | Hester | |
| 3,637,744 A | 1/1972 | Yardley et al. | |
| 3,652,588 A | 3/1972 | Hester | |
| 4,478,750 A | 10/1984 | Gadient | |
| 4,581,354 A | 4/1986 | Bell | |
| 4,841,056 A | 6/1989 | Hunter | |
| 4,902,691 A | 2/1990 | Cohen et al. | |
| 5,068,234 A | 11/1991 | D'Ambra et al. | |
| 5,219,859 A | 6/1993 | Festal et al. | |
| 5,494,928 A | 2/1996 | Boes | |

| | | | |
|---|---|---|---|
| 5,627,077 A | 5/1997 | Dyllick-brenzinger et al. |
| 5,814,642 A | 9/1998 | Goto et al. |
| 5,843,682 A | 12/1998 | Sigler et al. |
| 5,852,046 A | 12/1998 | Lang et al. |
| 6,017,945 A | 1/2000 | Rawson et al. |
| 6,380,238 B1 | 4/2002 | Adams et al. |
| 6,380,242 B1 | 4/2002 | Arora et al. |
| 6,407,092 B1 | 6/2002 | Hester et al. |
| 6,468,999 B1 | 10/2002 | Jacobsen et al. |
| 6,548,493 B1 | 4/2003 | Robichaud et al. |
| 6,552,017 B1 | 4/2003 | Robichaud et al. |
| 6,635,639 B2 | 10/2003 | Arora et al. |
| 6,828,314 B2 | 12/2004 | Frank et al. |
| 6,903,090 B2 | 6/2005 | Frank et al. |
| 8,338,447 B2 | 12/2012 | Hung et al. |
| 8,367,655 B2 | 2/2013 | Rajagopalan |
| 9,481,676 B2 | 11/2016 | Hung et al. |
| 11,254,640 B2 | 2/2022 | Olson et al. |
| 11,414,423 B1 | 8/2022 | Olson et al. |
| 11,697,651 B2 | 7/2023 | Muratore et al. |
| 2002/0022616 A1 | 2/2002 | Fu |
| 2002/0169322 A1 | 11/2002 | Arora et al. |
| 2002/0173503 A1 | 11/2002 | Robichaud et al. |
| 2003/0199491 A1 | 10/2003 | Hennequin |
| 2003/0212055 A1 | 11/2003 | Hennequin |
| 2003/0220321 A1 | 11/2003 | Frank et al. |
| 2003/0225058 A1 | 12/2003 | Frank et al. |
| 2003/0232828 A1 | 12/2003 | Bernotas et al. |
| 2003/0236278 A1 | 12/2003 | Bernotas et al. |
| 2004/0023947 A1 | 2/2004 | Martin et al. |
| 2004/0092502 A1 | 5/2004 | Fevig et al. |
| 2004/0242884 A1 | 12/2004 | Larsen et al. |
| 2005/0070558 A1 | 3/2005 | Vidal et al. |
| 2005/0250767 A1 | 11/2005 | Weiner et al. |
| 2006/0105030 A1 | 5/2006 | Windt-hanke et al. |
| 2006/0148808 A1 | 7/2006 | Robichaud et al. |

(Continued)

FOREIGN PATENT DOCUMENTS

| | | |
|---|---|---|
| AU | 614343 B2 | 8/1991 |
| CA | 2049642 A1 | 2/1992 |

(Continued)

OTHER PUBLICATIONS (Aug. 16, 2002) Chemical Abstracts Services, CAS Registry No. 405312-66-5, 2 pages.

(Continued)

*Primary Examiner* — Charanjit Aulakh

(74) *Attorney, Agent, or Firm* — Mintz Levin Cohn Ferris Glovsky and Popeo, P.C.

(57) ABSTRACT

Provided herein are tetracyclic heterocyclic compounds which can be useful for methods of treating a disease or for increasing neural plasticity. The compounds can also be useful for increasing dendritic spine density.

19 Claims, 15 Drawing Sheets

(56)     References Cited

U.S. PATENT DOCUMENTS

| | | |
|---|---|---|
| 2006/0199829 A1 | 9/2006 | Anandan et al. |
| 2006/0247228 A1 | 11/2006 | Umeda et al. |
| 2007/0197603 A1 | 8/2007 | Consonni et al. |
| 2007/0213359 A1 | 9/2007 | Burstein et al. |
| 2007/0254875 A1 | 11/2007 | Zhi et al. |
| 2009/0318446 A1 | 12/2009 | Fischer et al. |
| 2010/0022580 A1 | 1/2010 | Hung et al. |
| 2010/0152163 A1 | 6/2010 | Hung et al. |
| 2010/0317863 A1 | 12/2010 | Kuzmich et al. |
| 2011/0003793 A1 | 1/2011 | Guzzo et al. |
| 2011/0003836 A1 | 1/2011 | Mcknight et al. |
| 2011/0003840 A1 | 1/2011 | Rajagopalan |
| 2011/0229555 A1 | 9/2011 | Helson et al. |
| 2011/0245222 A1 | 10/2011 | Payan et al. |
| 2012/0245161 A1 | 9/2012 | Choi-sledeski et al. |
| 2012/0296569 A1 | 11/2012 | Shahaf et al. |
| 2013/0040977 A1 | 2/2013 | Mcknight et al. |
| 2013/0178618 A1 | 7/2013 | Boulanger |
| 2013/0190293 A1 | 7/2013 | Chakravarty et al. |
| 2013/0195866 A1 | 8/2013 | Bacskai et al. |
| 2013/0217675 A1 | 8/2013 | Chakravarty et al. |
| 2013/0225558 A1 | 8/2013 | Chakravarty et al. |
| 2014/0155384 A1 | 6/2014 | Protter et al. |
| 2014/0206711 A1 | 7/2014 | Chakravarty et al. |
| 2014/0228353 A1 | 8/2014 | Protter et al. |
| 2014/0275531 A1 | 9/2014 | Bollu et al. |
| 2014/0275548 A1 | 9/2014 | Basinger et al. |
| 2014/0296209 A1 | 10/2014 | Protter et al. |
| 2014/0303144 A1 | 10/2014 | Protter et al. |
| 2014/0343018 A1 | 11/2014 | Mcknight et al. |
| 2015/0057301 A1 | 2/2015 | Mcknight et al. |
| 2015/0141345 A1 | 5/2015 | Gozes et al. |
| 2015/0266884 A1 | 9/2015 | Protter et al. |
| 2016/0002237 A1 | 1/2016 | Rajagopalan |
| 2016/0207921 A1 | 7/2016 | Armer et al. |
| 2018/0263964 A1 | 9/2018 | Bamdad et al. |
| 2020/0030309 A1 | 1/2020 | Olson |
| 2020/0087305 A1 | 3/2020 | Tomesch et al. |
| 2020/0375967 A1 | 12/2020 | Stamets |
| 2021/0115042 A1 | 4/2021 | Armer et al. |
| 2022/0143051 A1 | 5/2022 | Manfredi et al. |
| 2022/0251040 A1 | 8/2022 | Olson et al. |
| 2022/0304980 A1 | 9/2022 | Arnold et al. |
| 2023/0117791 A1 | 4/2023 | Olson et al. |
| 2023/0150963 A1 | 5/2023 | Baggott |
| 2023/0202965 A1 | 6/2023 | Short et al. |
| 2023/0295106 A1 | 9/2023 | Olson et al. |
| 2024/0124456 A1 | 4/2024 | Cheng et al. |
| 2025/0057822 A1 | 2/2025 | Olson et al. |
| 2025/0122164 A1 | 4/2025 | Olson et al. |

FOREIGN PATENT DOCUMENTS

| | | |
|---|---|---|
| CA | 2715282 A1 | 8/2009 |
| CN | 102977091 A | 3/2013 |
| CN | 102977092 A | 3/2013 |
| EP | 0473550 A1 | 3/1992 |
| GB | 2550110 A | 11/2017 |
| JP | 2017031088 A | 2/2017 |
| NL | 6515701 A | 6/1966 |
| TW | 201927300 A | 7/2019 |
| WO | 199423720 A1 | 10/1994 |
| WO | 199524200 A1 | 9/1995 |
| WO | 199840102 A1 | 9/1998 |
| WO | 200038677 A1 | 7/2000 |
| WO | 200064899 A1 | 11/2000 |
| WO | 200170223 A1 | 9/2001 |
| WO | 2002059124 A2 | 8/2002 |
| WO | 2003091257 A1 | 11/2003 |
| WO | 2004005389 A1 | 1/2004 |
| WO | 2004064738 A2 | 8/2004 |
| WO | 2007118314 A1 | 10/2007 |
| WO | 2008117935 A1 | 10/2008 |
| WO | 2008157845 A1 | 12/2008 |
| WO | 2009035473 A2 | 3/2009 |
| WO | 2009036996 A2 | 3/2009 |
| WO | 2009103022 A1 | 8/2009 |
| WO | 2011103433 A1 | 8/2011 |
| WO | 2012112966 A1 | 8/2012 |
| WO | 2012154261 A1 | 11/2012 |
| WO | 2013007698 A1 | 1/2013 |
| WO | 2013191704 A1 | 12/2013 |
| WO | 2017216279 A1 | 12/2017 |
| WO | 2018045178 A1 | 3/2018 |
| WO | 2018064465 A1 | 4/2018 |
| WO | 2018209341 A1 | 11/2018 |
| WO | 2019099402 A1 | 5/2019 |
| WO | 2020169851 A1 | 8/2020 |
| WO | 2020176597 A1 | 9/2020 |
| WO | 2020176599 A1 | 9/2020 |
| WO | 2020181050 A1 | 9/2020 |
| WO | 2020186027 A1 | 9/2020 |
| WO | 2021076572 A1 | 4/2021 |
| WO | 2021178691 A1 | 9/2021 |
| WO | 2022020352 A1 | 1/2022 |
| WO | 2022051670 A1 | 3/2022 |
| WO | 2022067165 A1 | 3/2022 |
| WO | 2022081631 A1 | 4/2022 |
| WO | 2022120181 A1 | 6/2022 |
| WO | 2022120475 A1 | 6/2022 |
| WO | 2022170268 A1 | 8/2022 |
| WO | 2022221415 A2 | 10/2022 |
| WO | 2022246554 A1 | 12/2022 |
| WO | 2023283364 A2 | 1/2023 |
| WO | 2023018480 A1 | 2/2023 |
| WO | 2023018864 A1 | 2/2023 |
| WO | 2023023298 A1 | 2/2023 |
| WO | 2023059546 A1 | 4/2023 |
| WO | 2023073423 A1 | 5/2023 |
| WO | 2023077127 A2 | 5/2023 |
| WO | 2023081306 A1 | 5/2023 |
| WO | 2023081753 A1 | 5/2023 |
| WO | 2023092195 A1 | 6/2023 |
| WO | 2023108164 A2 | 6/2023 |
| WO | 2023108165 A2 | 6/2023 |
| WO | 2023108174 A1 | 6/2023 |
| WO | 2023114472 A1 | 6/2023 |
| WO | 2023115006 A1 | 6/2023 |
| WO | 2023115060 A1 | 6/2023 |
| WO | 2023115165 A1 | 6/2023 |
| WO | 2023115166 A1 | 6/2023 |
| WO | 2023122135 A1 | 6/2023 |
| WO | 2024059495 A1 | 3/2024 |
| WO | 2025014719 A2 | 1/2025 |
| WO | 2025080608 A1 | 4/2025 |
| WO | 2025080609 A1 | 4/2025 |
| WO | 2025137596 A1 | 6/2025 |

OTHER PUBLICATIONS (Dec. 26, 2004) Chemical Abstracts Services, CAS Registry No. 802581-10-8, 2 pages.

(Jan. 10, 2013) Chemical Abstracts Services, CAS Registry No. 1416330-38-5, 2 pages.

(Nov. 16, 1984) Chemical Abstracts Services, CAS Registry No. 7546-69-2, 2 pages.

(Nov. 16, 1984) Database Registry, Chemical Abstracts Services, CAS Registry No. 7546-76-1, 2 pages.

(Nov. 16, 1984) Database Registry, Chemical Abstracts Services, CAS Registry No. 7546-72-7, 2 pages.

(Nov. 16, 1984) Database Registry, Chemical Abstracts Services, CAS Registry No. 7546-73-8, 2 pages.

(Nov. 16, 1984) Database Registry, Chemical Abstracts Services, CAS Registry No. 7546-75-0, 2 pages.

(Nov. 27, 2012) Chemical Abstracts Services, CAS Registry No. 1407483-64-0, 2 pages.

(2018) Depression, The National Institute of Mental Health: www.nimh.nih.gov, 13 pages.

European Search Report for EP Application 17857489.3, mailed on Apr. 8, 2020, 6 pages.

International Search Report and Written Opinion for PCT/US2022/024626, mailed Jul. 1, 2022, 9 pages.

(56)                References Cited

OTHER PUBLICATIONS

International Search Report and Written Opinion for PCT/US2022/079217, mailed Feb. 1, 2023, 9 pages.
International Search Report and Written Opinion for PCT/US2022/081927, mailed Apr. 17, 2023, 11 pages.
Search Report and Written Opinion issued in International Application No. PCT/US2020/019858, mailed on Jul. 15, 2020, 11 pages.
Search Report and Written Opinion received for International Application No. PCT/US2020/055507, mailed on Mar. 1, 2021, 12 pages.
Search Report and Written Opinion received for PCT Application No. PCT/US2017/054277, mailed on Dec. 14, 2017, 10 pages.
Search Report and Written Opinion received for PCT Application No. PCT/US2020/019856, mailed on Jun. 2, 2021, 11 pages.
(2016) PUBCHEM-SID-274223890, 5 pages.
Supplementary European Search Report and Search Opinion for PCT/US2020019858, mailed Mar. 11, 2022, 9 pages.
Party Observations received for European Application No. 17857489.3, mailed on Feb. 15, 2022, 2 pages.
Abate et al. (2005) "Interaction of Chiral MS-245 Analogs at h5-HT6 Receptors", Bioorganic & medicinal chemistry letters, 15(15):3510-3513.
Anderson et al. (Sep. 2003) "The Process of Structure-Based Drug Design", Chemistry and Biology, 10(9):787-797.
Antonaci et al. (May 17, 2016) "Recent Advances in Migraine Therapy", SpringerPlus, 5:1-14.
Borovac, Josipa (Mar. 24, 2016) "Side Effects of a Dopamine Agonist Therapy for Parkinson's Disease: A Mini-Review of Clinical Pharmacology", Yale Journal of Biology and Medicine, 89:37-47.
Cameron et al. (2021) "A Non-Hallucinogenic Psychedelic Analogue with Therapuetic Potential", Nature, 589:474-479 (24 pages).
Cameron et al. (Jul. 2019) "Chronic, Intermittent Microdoses of the Psychedelic N,N-Dimethyltryptamine (DMT) Produce Positive Effects on Mood and Anxiety in Rodents", ACS Chemical Neuroscience, 10(7):3261-3270.
Cameron et al. (Oct. 2018) "Dark Classics in Chemical Neuroscience: N,N-Dimethyltryptamine (DMT)", ACS Chemical Neuroscience, 9(10):2344-2357.
Cameron et al. (Jul. 2018) "Effects of N,N-Dimethyltryptamine on Rat Behaviors Relevant to Anxiety and Depression", ACS Chemical Neuroscience, 9(7):1582-1590 (22 pages).
Cameron et al. (Apr.-Jun. 2020) "Psychedelic Microdosing: Prevalence and Subjective Effects", Jounal of Psychoactive Drugs, 52(2):113-122.
Chang-Fong et al. (Jan. 21, 2002) "Evaluation of Isotryptamine Derivatives at 5-HT2 Serotonin Receptors", Bioorganic & Medicinal Chemistry Letters, 12(2):155-158.
Chen et al. (Apr. 2022) "Iboga-type Alkaloids with Indolizidino[8,7-b]Indole Scaffold and Bisindole Alkaloids from Tabernaemontana Bufalina Lour", Phytochemistry, 196:113089.
Chiba et al. (Jun. 5, 2010) "Cabergoline, a Dopamine Receptor Agaonist, has an Antidepressant-like Property and Enhances Brain-derived Neurotrophic Factor Signaling", Psychpharmacology, 211(3):291-301 (23 pages).
Church et al. (2013) "'Ecstasy' Enhances Noise-induced Hear", Hearing Research, 302:96-106.
Dong et al. (May 13, 2021) "Psychedelic-inspired Drug Discovery Using an Engineered Biosensor", Cell, 184(10):2779-2792.e18.
Dunlap et al. (Jan. 2020) "Identification of Psychoplastogenic N,N-Dimethylaminoisotryptamine (isoDMT) Analogues through Structure-Activity Relationship Studies", Journal of Medicinal Chemistry, 63(3):1142-1155 (36 pages).
Eiter et al. (1952) "Zur Konstitution des Folicanthins: II. Mitteilung uber Folicanthin, ein neues Alkaloid aus den Blattern des Calycanthus floridus L", Monastshefte Fur Chemies—Chemical Monthly, 83(6):1453-1476.
Fitzgerald et al. (1999) "High-Affinity Agonist Binding Correlates with Efficacy (Intrinsic Activity) at the Human Serotonin 5-HT2A and 5-HT2C Receptors: Evidence Favoring the Ternary Complex and Two-State Models of Agonist Action", Journal of Neurochemistry, 72(5):2127-2134.
Glennon et al. (2000) "Binding of Beta-Carbolines and Related Agents at Serotonin (5-HT(2) and 5-HT(1A)), Dopamine (D(2)) and Benzodiazepine Receptors", Drug & Alcohol Dependence, 60(2):121-132.
Glennon et al. (1983) "DOM-stimulus Generalization to LSD and Other Hallucinogenic Indolealkylamines", European Journal of Pharmacology, 86:453-459.
Glennon et al. (Jan. 1, 1984) "Synthesis and Evaluation of a Novel Series of N,N-Dimethylisotryptamines", Journal of Medicinal Chemistry, 27(1):41-45.
Goadsby et al. (Nov. 11, 2005) "Comparative Efficacy of Eletriptan and Sumatriptan in Reducing Headache Recurrence in High-Risk Migraine Patients", Journal of the Neurological Sciences, 1533, 1 page.
Golda et al. (Jun. 1987) "Animal Model of Depression: Drug Induced Changes Independent of Changes in Exploratory Activity", Activitas nervosa superior, 29(2):114-115.
Golda et al. (Mar. 1986) "Animal Model of Depression: Imipramine, Bromocriptine and Lisuride Alleviate Motor Depression", Activitas Nervosa Superior, 28(1):26-27 (4 pages).
Golda et al. (1984) "Reactivity to the Electric Shocks and Motor Depression as a Consequence of Inescapable Shocking: The Effect of Acute Lisuride Treatment", Sb Ved Pr Lek Fak Karlovy Univerzity Hradci Kralove, 27(4):377-392.
Halford, Bethany (Dec. 2020) "Ibogaine Inspires Potential Neuropsychiatric Treatment", C&E News, 3 pages.
Harris et al. (Nov.-Dec. 2012) "Cabergoline Associated with First Episode Mania", Psychosomatics, 53(6):595-600 (10 pages).
Hester et al. (Jan. 1, 1968) "Azepinoindoles. I. Hexahydroazepino[4,5-b]indoles", Journal of Medicinal Chemistry, 11:101-106.
Hougaku et al. (Jan. 1994) "Therapeutic Effect of Lisuride Maleate on Post-Stroke Depression", Japanese Journal of Geriatrics, 31:52-59.
Huang et al. (2005) "Comparison of the Use of Aqueous and Nonaqueous Buffers in Association with Cyclodextrin for the Chiral Separation of 3,4-methylenedioxymethamphetamine and Related Compounds", Electrophoresis, 26(20):3904-3909.
Izumi et al. (Dec. 2000) "Open Pergolide Treatment of Tricyclic and Heterocyclic Antidepressant-Resistant Depression", Journal of Affective Disorders, 61:127-132.
Konopaske et al. (Dec. 2014) "Prefrontal Cortical Dendritic Spine Pathology in Schizophrenia and Bipolar disorder", JAMA Psychiatry, 71(12):1323-1331.
Lacivita et al. (2006) "Selective Agents for Serotonin (2C) (5-HT2C) Receptor", Current Topics in Medicinal Chemistry, 6(18):1927-1970.
Lieberman et al. (Nov. 1981) "Use of Lisuride in Advanced Parkinson's Disease. Potent Dopamine and Serotonin Agonist", New York State Journal of Medicine, 81(12):1751-1755.
Luquin et al. (1987) "Parenteral Administration of Lisuride in Parkinson's Disease", Advances in Neurology, 45:561-568.
Ly et al. (Jun. 12, 2018) "Psychedelics Promote Structural and Functional Neural Plasticity", Cell Reports, 23(11):3170-3182.
Masuda et al. (2000) "The Effect of Globopentaosylceramide on a Depression Model, Mouse Forced Swimming", The Tohoku journal of experimental medicine, 191(1):47-54.
Meintzschel et al. (Oct. 12, 2005) "Modification of Practice-Dependent Plasticity in Human Motor Cortex by Neuromodulators", Cerebral Cortex, 16(8):1106-1115.
Meyer et al. (Jan. 2001) "The Effect of Paroxetine on 5-HT 2A Receptors in Depression: An [18F]Setoperone PET Imaging Study", The American Journal of Psychiatry, 158(1):78-85.
Moyer et al. (2015) "Dendritic Spine Alterations in Schizophrenia", Neuroscience Letters, 601:46-53 (18 pages).
Nakamura et al. (1989) "Effects in Animal Models of Depression of Lisuride Alone and Upon Coadministration with Antidepressants", Nihon Yakurigaku Zasshi. Folia pharmacol.japonica, 94(1):81-89.
Odaka et al. (Jun. 2014) "Cabergoline, Dopamine D2 REceptor Agonist, Prevents Neuronal Cell Death under Oxidative Stress via Reducing Excitotoxicity", PLoS One, 9(6):12 pages.

(56)                    References Cited

OTHER PUBLICATIONS

Penzes et al. (Mar. 2011) " Dendritic Spine Pathology in Neuropsychiatric Disorders", Nature Neuroscience Review, 14(3):285-293.
(Jul. 23, 2013) "Product Monograph", Pfizer Cananda Inc., 1-2.
Pieroni et al. (2015) "Rational Design and Synthesis of Thioridazine Analogues as Enhancers of the Antituberculosis Therapy", Journal of medicinal chemistry, 58(15):5842-5853 (43 pages).
PubChem (Oct. 20, 2014) "1,2,3,4-Tetrahydropyrrolo[2,3-b]Indole", PubChem CID 82415753, 8 pages.
PubChem (Jun. 16, 2016) "3,4-Trimethylen-inden", PubChem SID 314981250, 5 pages.
PubChem (Aug. 8, 2005) "Carbazole, 9-(1-methyl-2-piperidyl)methyl-", PubChem CID 43403, 10 Pages.
Pumphrey et al. (Jun. 11, 2012) "Rhll2-Catalyzed Synthesis of $\alpha$-, $\beta$-, or $\delta$-Carbolines from Aryl Azides", Angewandte Chemie International Edition, 51(24): 5920-5923 (10 pages).
Sanches et al. (2016) "Antidepressant Effects of a Single Dose of Ayahuasca in Patients with Recurrent Depression: A SPECT Study", Journal of clinical psychopharmacology, 36(1):77-81.
Sharma et al. (Dec. 2009) "Intranasal Cabergoline: Pharmacokinetic and Pharmacodynamic Studies", AAPS PharmSciTech, 10(4):1321-1330.
Teruya (1967) "Studies on 2-benzimidazolethiol Derivatives. V. Structure-activity Relationship on Analgesic Action of 1-(Dialkylamino-alkyl)-2-(P-ethoxyphenylthio)benzimidazole", Journal of the Pharmaceutical Society of Japan, doi: 10.1248/yakushi1947.87.3_301., 87(3):301-309.
Thiel, Karla (May 2004) "Structure-Aided Drug Design's Next Generation", Nature Biology, 22(5):513-519.
Tittarelli et al. (2015) "Recreational Use, Analysis and Toxicity of Tryptamines", Current Neuropharmacology, 13(1):26-46.
Vargas et al. (Oct. 2021) "Psychedelics and Other Psychoplastogens for Treating Mental Illness", Frontiers in Psychiatry, 12:1-19.
Whitehouse et al. (2019) "Development of Inhibitors against *Mycobacterium abscessus* tRNA (m1G37) Methyltransferase (TrmD) Using Fragment-Based Approaches", Journal of medicinal chemistry, 62(15):7210-7232.
Zetler et al. (Jan. 1968) "Die Wirkung von 11 Indol-Alkaloiden auf das Meerschweinchen-Herz in vivo und in vitro, verglichen mit 2 synthetischen Azepinoindolen, Chinidin und Quindonium", Naunyn-Schmiedebergs Archiv für Pharmakologie und experimentelle Pathologie 260, 26-49.
Zetler et al. (1970) "Inhibition of Cardiac Effects of Noradrenaline by Eleven Indole Alkaloids, Two Azepinoindoles, Quinidine, Quindonium, and Propranolol", Pharmacology, 4:129-142.
Zetler et al. (1972) "Refractory Period and Strophanthin Actions, as Influenced by Four Indole Alkaloids and Two Synthetic Azepinoindoles", Pharmacology, 8:235-243.
Zubenko et al. (2019) "Pyridine-Azepine Structural Modification of 3,4-Dihydro-nor-isoharmine", Russian Journal of Organic Chemistry, 55(1):74-82.
International Search Report and Written Opinion for PCT/US2023/073837, mailed on Jan. 26, 2024, 9 pages.
(Jan. 10, 2024) Third Party Observations received for European Application No. 17857489.3, 7 pages.
Blair et al. (2000) "Effect of Ring Fluorination on the Pharmacology of Hallucinogenic Tryptamines", Journal of Medicinal Chemistry, 43(24):4701-4710.
Carman et al. (1976) "Negative Effects of Melatonin on Depression", The American Journal of Psychiatry, 133(10):1181-1186.
Colley, Claire (Sep. 7, 2015) "This is What it Feels Like to Treat Depression with Magic Mushrooms", https://www.vice.com/en/article/8gk5wz/microdosing-psilocybin-depression-184, 10 pages.
Database (Dec. 2, 2011) "CAS Registry No. 1347326-94-6", 1 page.
Database (Dec. 20, 2013) "CAS Registry No. 1499823-45-8", 2 pages.
Database (Dec. 23, 2013) "CAS Registry No. 1501213-32-6", 2 pages.

Database (Dec. 24, 2013) "CAS Registry No. 1502739-86-7", 2 pages.
Database (Dec. 25, 2013) "CAS Registry No. 1503723-45-2", 2 pages.
Database (Dec. 27, 2013) "CAS Registry No. 1505385-98-7", 2 pages.
Database (Jan. 2, 2014) "CAS Registry No. 1509251-72-2", 2 pages.
Database (Jan. 7, 2014) "CAS Registry No. 1513834-45-1", 2 pages.
Database (Jan. 8, 2014) "CAS Registry No. 1513937-46-6", 2 pages.
Database (Jan. 2014) "CAS Registry No. 1514378-08-5", 2 pages.
Database (Jan. 9, 2014) "CAS Registry No. 1515073-46-7", 2 pages.
Database (Jan. 9, 2014) "CAS Registry No. 1515565-33-9", 2 pages.
Database (Jan. 10, 2014) "CAS Registry No. 1516490-69-9", 2 pages.
Database (Jan. 14, 2014) "CAS Registry No. 1519408-31-1", 2 pages.
Database (Jan. 16, 2014) "CAS Registry No. 1521620-08-5", 2 pages.
Database (Jan. 19, 2014) "CAS Registry No. 1523634-22-1", 2 pages.
Database (Jan. 20, 2014) "CAS Registry No. 1524903-93-2", 2 pages.
Database (Jan. 20, 2014) "CAS Registry No. 1525468-14-7", 2 pages.
Database (Jan. 30, 2014) "CAS Registry No. 1533723-14-6", 2 pages.
Database (Jan. 30, 2014) "CAS Registry No. 1533998-25-2", 2 pages.
Database (Feb. 9, 2014) "CAS Registry No. 1540077-46-0", 2 pages.
Database (Feb. 10, 2014) "CAS Registry No. 1540652-24-1", 2 pages.
Database (Nov. 16, 1984) "CAS Registry No. 15918-67-9", 2 pages.
Database (Nov. 16, 1984) "CAS Registry No. 15918-68-0", 2 pages.
Database (Nov. 16, 1984) "CAS Registry No. 15918-91-9", 2 pages.
Database (Nov. 16, 1984) "CAS Registry No. 15923-19-0", 2 pages.
Database (Jun. 14, 2015) "CAS Registry No. 1779925-03-9", 2 pages.
Database (Jun. 17, 2015) "CAS Registry No. 1781710-62-0", 2 pages.
Database (Jun. 17, 2015) "CAS Registry No. 1781798-70-6", 2 pages.
Database (Jun. 17, 2015) "CAS Registry No. 1781904-21-9", 2 pages.
Database (Jun. 17, 2015) "CAS Registry No. 1781908-34-6", 2 pages.
Database (Jun. 17, 2015) "CAS Registry No. 1782881-47-3", 2 pages.
Database (Jun. 19, 2015) "CAS Registry No. 1784120-59-7", 2 pages.
Database (Jun. 21, 2015) "CAS Registry No. 1785609-23-5", 2 pages.
Database (Feb. 17, 2017) "CAS Registry No. 2072109-20-5", 2 pages.
Database (Feb. 17, 2017) "CAS Registry No. 2072109-30-7", 2 pages.
Database (Apr. 16, 2002) "CAS Registry No. 405305-92-2", 2 pages.
Database (Apr. 16, 2002) "CAS Registry No. 405305-95-5", 2 pages.
Database (Apr. 16, 2002) "CAS Registry No. 405311-77-5", 2 pages.
Database (May 24, 2004) "CAS Registry No. 685503-57-5", 2 pages.
Database (Aug. 31, 2004) "CAS Registry No. 736129-10-5", 2 pages.
Database (Oct. 1, 2004) "CAS Registry No. 755746-20-4", 2 pages.
Database (Oct. 7, 2004) "CAS Registry No. 757934-75-1", 2 pages.

(56)             References Cited

OTHER PUBLICATIONS

Database (Oct. 28, 2004) "CAS Registry No. 770702-18-6", 2 pages.
Database (Nov. 11, 2004) "CAS Registry No. 778568-40-4", 2 pages.
Database (Nov. 14, 2004) "CAS Registry No. 780030-99-1", 2 pages.
Marek et al. (1989) "Evidence for Involvement of 5-Hydroxytryptaminei Receptors in Antidepressant-Like Drug Effects on Differential-Reinforcement-of-Low-Rate 72-Second Behavior", The Journal of Pharmacology and Experimental Therapeutics, 250(1):60-71.
Nichols, David E. (2018) "Dark Classics in Chemical Neuroscience: Lysergic Acid Diethylamid (LSD)", ACS Chemical Neuroscience, 9(10):2331-2343.
PubChem (2021) "5-Bromo-6-chloro-N,Ndiethylnicotinamide", SID-441175770, 5 pages.
PubChem (2018) "SID-368776104", 5 pages.
Ray, Thomas S. (2010) "Psychedelics and the Human Receptorome", PLOS One, 5(2):1-17.
Turton et al. (2014) "A Qualitative Report on the Subjective Experience of Intravenous Psilocybin Administered in an fMRI Environment", Current Drug Abuse Reviews, 7(2):117-127.
(2005) "Chapter 11: Serotonin and Histamine." In Shao Fuyuan and Wang Yuhui (Eds.), Molecular Neuropharmacology, Shanghai Science and Technology Press, 4th ed., pp. 261-263.
(2015) "Chapter 5: Pathogenesis of Alzheimer's Disease and Progress in Drug Research", In Wang X. (Ed.), Practical Molecular Pharmacology, Peking Union Medical College Press, ISBN 978-7-5679-0411-8., 2nd ed., pp. 127.
Extended European Search Report and Search Opinion for EP Application No. 22788861.7, mailed on Aug. 4, 2025, 5 pages.
International Search Report and Written Opinion for PCT/US2024/050417, mailed on Jan. 16, 2025, 11 pages.
International Search Report and Written Opinion received for PCT/US2024/050418, mailed on Feb. 5, 2025, Feb. 5, 2025, 12 pages.
Loach et al. (2014) "C7-Derivatization of C3-alkylindoles Including Tryptophans and Tryptamines", The Journal of Organic Chemistry, 79:11254-11263.
Mantegani et al. (1998) "5 (10→ 9) Abeo-ergoline Derivatives: Synthesis, 5-HT1A-receptor Affinity and Selectivity", European Journal of Medicinal Chemistry, 33(4):279-292.
PubChem (Aug. 9, 2005) "Ergoline-8-beta-carboxamide, 9,10-didehydro-N,N-diethyl-12-methoxy-6-methyl-", CID 3039341, National Center for Biotechnology Information, Retrieved from https://pubchem.ncbi.nlm.nih.gov/ compound/3039341, 10 pages.
Ward et al. (1988) "Ergolines as Selective 5-HT1 Agonists", Journal of Medicinal Chemistry, 31(8):1512-1519.

FIG. 5A
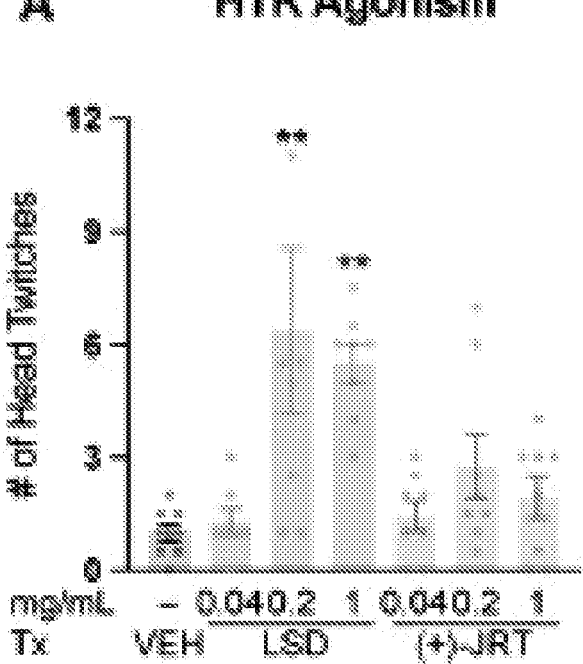
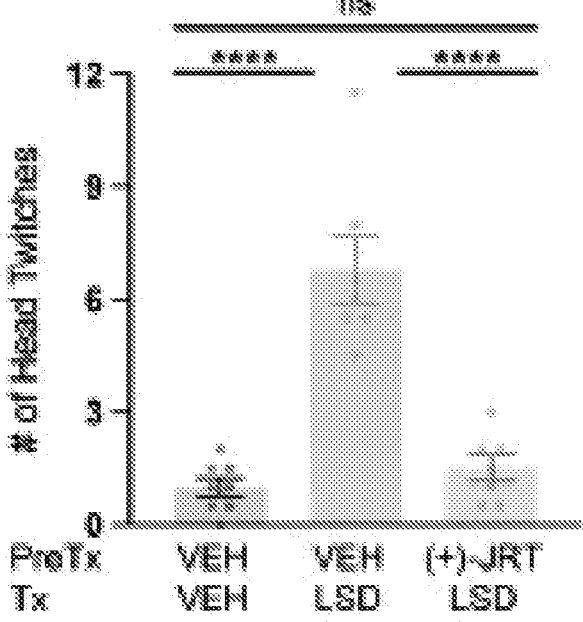

FIG. 6

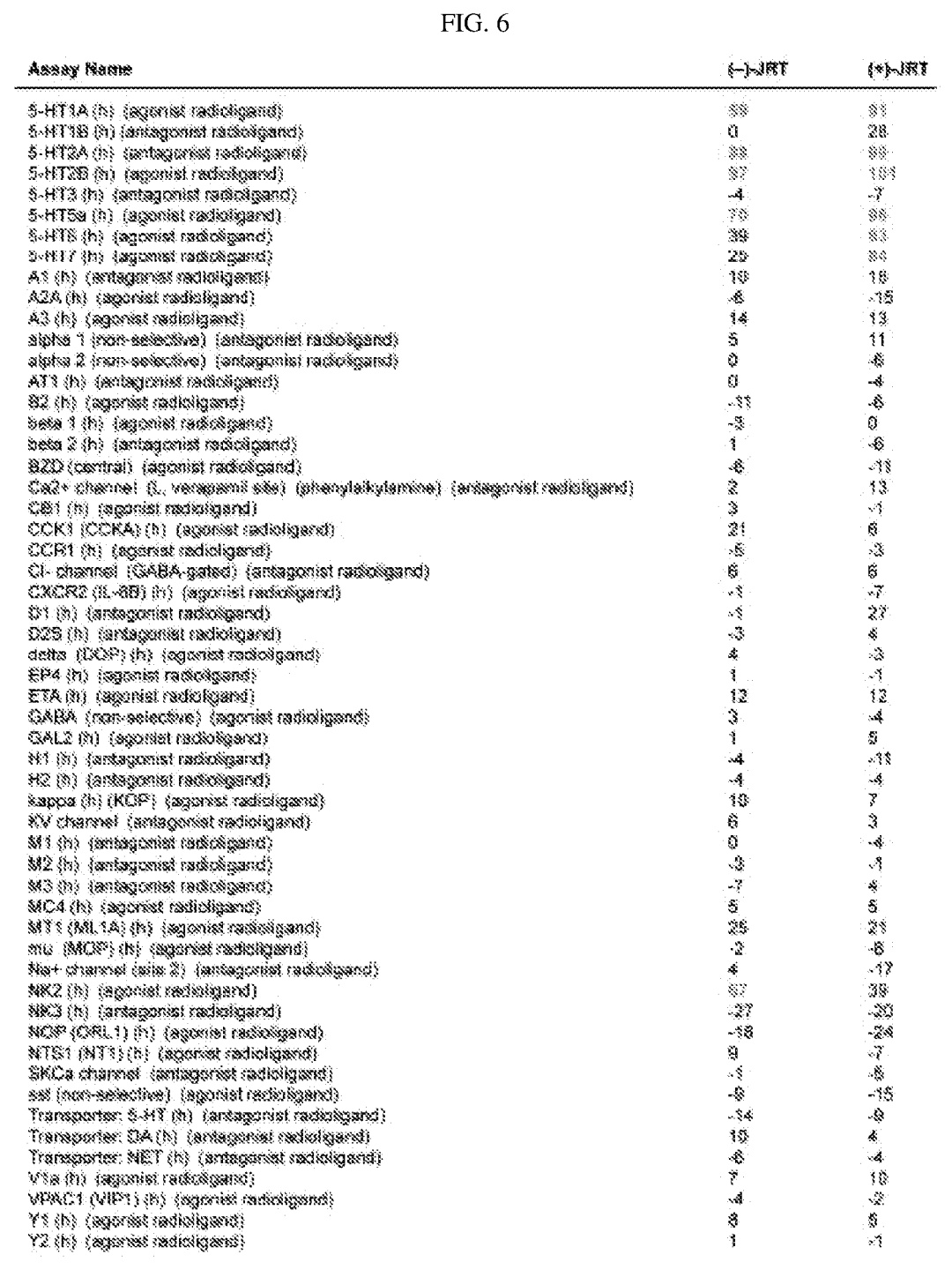

| Assay Name | (−)-JRT | (+)-JRT |
|---|---|---|
| 5-HT1A (h) (agonist radioligand) | 88 | 88 |
| 5-HT1B (h) (antagonist radioligand) | 0 | 28 |
| 5-HT2A (h) (antagonist radioligand) | 88 | 88 |
| 5-HT2B (h) (agonist radioligand) | 87 | 100 |
| 5-HT3 (h) (antagonist radioligand) | -4 | -7 |
| 5-HT5a (h) (agonist radioligand) | 70 | 88 |
| 5-HT6 (h) (agonist radioligand) | 39 | 83 |
| 5-HT7 (h) (agonist radioligand) | 25 | 84 |
| A1 (h) (antagonist radioligand) | 19 | 18 |
| A2A (h) (agonist radioligand) | -6 | -15 |
| A3 (h) (agonist radioligand) | 14 | 13 |
| alpha 1 (non-selective) (antagonist radioligand) | 5 | 11 |
| alpha 2 (non-selective) (antagonist radioligand) | 0 | -6 |
| AT1 (h) (antagonist radioligand) | 0 | -4 |
| B2 (h) (agonist radioligand) | -11 | -6 |
| beta 1 (h) (agonist radioligand) | -5 | 0 |
| beta 2 (h) (antagonist radioligand) | 1 | -6 |
| BZD (central) (agonist radioligand) | -6 | -11 |
| Ca2+ channel (L, verapamil site) (phenylalkylamine) (antagonist radioligand) | 2 | 13 |
| CB1 (h) (agonist radioligand) | 3 | -1 |
| CCK1 (CCKA) (h) (agonist radioligand) | 21 | 6 |
| CCR1 (h) (agonist radioligand) | -5 | -3 |
| Cl- channel (GABA-gated) (antagonist radioligand) | 6 | 6 |
| CXCR2 (IL-8B) (h) (agonist radioligand) | -3 | -7 |
| D1 (h) (antagonist radioligand) | -1 | 27 |
| D2S (h) (antagonist radioligand) | -3 | 4 |
| delta (DOP) (h) (agonist radioligand) | 4 | -3 |
| EP4 (h) (agonist radioligand) | 1 | -1 |
| ETA (h) (agonist radioligand) | 12 | 12 |
| GABA (non-selective) (agonist radioligand) | 3 | -4 |
| GAL2 (h) (agonist radioligand) | 1 | 5 |
| H1 (h) (antagonist radioligand) | -4 | -11 |
| H2 (h) (antagonist radioligand) | -4 | -4 |
| kappa (h) (KOP) (agonist radioligand) | 19 | 7 |
| KV channel (antagonist radioligand) | 6 | 3 |
| M1 (h) (antagonist radioligand) | 0 | -4 |
| M2 (h) (antagonist radioligand) | -3 | -1 |
| M3 (h) (antagonist radioligand) | -7 | 4 |
| MC4 (h) (agonist radioligand) | 5 | 5 |
| MT1 (ML1A) (h) (agonist radioligand) | 25 | 23 |
| mu (MOP) (h) (agonist radioligand) | -2 | -6 |
| Na+ channel (site 2) (antagonist radioligand) | 4 | -17 |
| NK2 (h) (agonist radioligand) | 87 | 39 |
| NK3 (h) (antagonist radioligand) | -27 | -20 |
| NOP (ORL1) (h) (agonist radioligand) | -18 | -24 |
| NTS1 (NT1) (h) (agonist radioligand) | 9 | -7 |
| SKCa channel (antagonist radioligand) | -1 | -6 |
| sst (non-selective) (agonist radioligand) | -9 | -15 |
| Transporter: 5-HT (h) (antagonist radioligand) | -14 | -9 |
| Transporter: DA (h) (antagonist radioligand) | 19 | 4 |
| Transporter: NET (h) (antagonist radioligand) | -6 | -4 |
| V1a (h) (agonist radioligand) | 7 | 18 |
| VPAC1 (VIP1) (h) (agonist radioligand) | -4 | -2 |
| Y1 (h) (agonist radioligand) | 8 | 5 |
| Y2 (h) (agonist radioligand) | 1 | -1 |

Injection Volume        : 15 uL
Data File Name           : 01042021B1.lcd
Method File Name      : CHIRAL-MET-B50-1.0mL.lcm
Report File Name       : Default.lcr
Data Acquired            : 01-04-2021 15:50:44
Description                 : COLUMN::CHIRAL PAK IC(250mmX 4.6mm,5μm)
Mobile Phase A :0.1%DEA in n-Hexane
 Mobile Phase B :IPA
 A:B:50:50
Flow:1.0mL/min 1  PDA Multi 1/240nm 4nm PeakTable PDA Ch1 240nm 4nm

| Peak# | Ret. Time | Area | Height | Area % |
|---|---|---|---|---|
| 1 | 7.711 | 3788998 | 231995 | 42.180 |
| 2 | 9.890 | 5193924 | 249782 | 57.820 |
| Total | | 8982922 | 481778 | 100.000 |

Injection Volume          : 15 uL
Data File Name            : 01042021B2.lcd
Method File Name          : CHIRAL-MET-B50-1.0mL.lcm
Report File Name          : Default.lcr
Data Acquired             : 01-04-2021  16:16:22
Description        : COLUMN::CHIRAL PAK IC(250mmX 4.6mm,5μm)
Mobile Phase A :0.1%DEA in n-Hexane
 Mobile Phase B :IPA
 A:B:50:50
Flow:1.0mL/min 1  PDA Multi 1/240nm 4nm PeakTable PDA Ch1 240nm 4nm

| Peak# | Ret. Time | Area | Height | Area % |
|---|---|---|---|---|
| 1 | 7.805 | 9642643 | 582879 | 100.000 |
| Total | | 9642643 | 582879 | 100.000 |

Injection Volume        : 10 uL
Data File Name          : 01042021B3.lcd
Method File Name        : CHIRAL-MET-B50-1.0mL.lcm
Report File Name        : Default.lcr
Data Acquired           : 01-04-2021  16:34:43
Description             : COLUMN::CHIRAL PAK IC(250mmX 4.6mm,5μm)
Mobile Phase A :0.1%DEA in n-Hexane
 Mobile Phase B :IPA
 A:B:50:50
Flow:1.0mL/min PeakTable PDA Ch1 240nm 4nm

| Peak# | Ret. Time | Area | Height | Area % |
|---|---|---|---|---|
| 1 | 7.960 | 31705 | 1915 | 0.561 |
| 2 | 10.140 | 5619691 | 267077 | 99.439 |
| Total | | 5651396 | 268993 | 100.000 |

FIG. 11
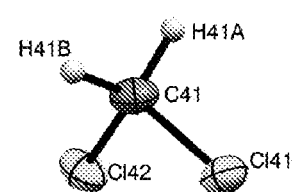
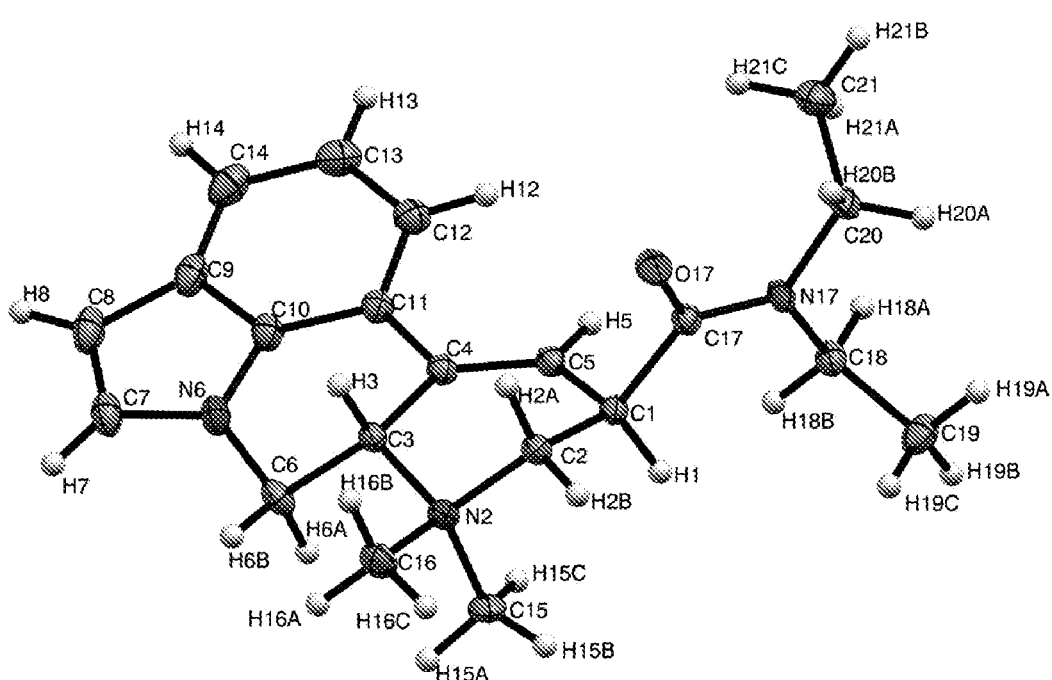

TETRACYCLIC COMPOUNDS FOR TREATING BRAIN DISORDERS

CROSS-REFERENCE TO RELATED APPLICATIONS

This application claims priority to U.S. Provisional Appl. No. 63/174,266, filed Apr. 13, 2021, which is incorporated herein in its entirety for all purposes.

STATEMENT AS TO RIGHTS TO INVENTIONS MADE UNDER FEDERALLY SPONSORED RESEARCH AND DEVELOPMENT

This invention was made with Government support under Grant No. R01GM128997 awarded by the National Institutes of Health. The Government has certain rights in this invention.

BACKGROUND

Altered synaptic connectivity and plasticity has been observed in the brains of individuals with neuropsychiatric and neurological diseases/disorders. Psychoplastogens promote neuronal growth and improve neuronal architecture through mechanisms that may involve the activation of the serotonin 5-HT$_2$ receptors. Modulators of these biological targets, such as, for example, N,N-dimethyltryptamine (DMT), ibogaine, and lysergic acid diethylamide (LSD) have demonstrated psychoplastogenic properties. For example, LSD and other analogs of the ergoline scaffold are capable of rectifying deleterious changes in neuronal structure that are associated with neuropsychiatric and neurological diseases/disorders. Such structural alterations include, for example, the loss of dendritic spines and synapses in the prefrontal cortex (PFC) as well as reductions in dendritic arbor complexity. Furthermore, pyramidal neurons in the PFC exhibit top-down control over areas of the brain controlling motivation, fear, reward, and cognition. Hallucinogenic psychoplastogens have demonstrated antidepressant, anxiolytic, and anti-addictive effects in the clinic. However, their subjective effects have limited their clinical utility. Moreover, hallucinogenic compounds are contraindicated for psychotic illnesses like schizophrenia, which are well known to involve the loss of dendritic spines in the PFC. Thus, non-hallucinogenic psychoplastogens may have distinct advantages over their hallucinogenic counterparts.

Provided herein are compounds with clinically relevant therapeutic efficacy that have improved physicochemical properties, and possess reduced hallucinogenic (e.g., non-hallucinogenic) properties as compared to their hallucinogenic (e.g., ergoline) counterparts.

BRIEF SUMMARY OF THE INVENTION

In one embodiment, provided herein is a compound, or a pharmaceutically acceptable salt thereof, having a structure of Formula (K):

(K)

wherein: each R$^{1a}$, R$^{1b}$, R$^{1c}$, and R$^{1d}$ is independently H, C$_{1-6}$ alkyl, C$_{2-6}$ alkenyl, C$_{2-6}$ alkynyl, C$_{1-6}$ alkoxy, C$_{1-6}$ alkoxyalkyl, halogen, C$_{1-6}$ haloalkyl, C$_{1-6}$ haloalkoxy, —NO$_2$, or —CN; alternatively, two R$^{1a}$ groups on adjacent ring atoms are combined to form a C$_{4-8}$ cycloalkyl or 4 to 8 membered heterocycloalkyl having 1 to 2 heteroatoms, each independently N, O, or S; R$^{2a}$ and R$^{2b}$ are each independently H, C$_{1-6}$ alkyl, C$_{3-6}$ cycloalkyl, C$_{1-6}$ alkoxy, C$_{1-6}$ alkoxyalkyl, C$_{1-6}$ haloalkyl, or C$_{1-6}$ haloalkoxy; alternatively, R$^{2a}$ and R$^{2b}$ are combined to form a 4 to 8 membered heterocycloalkyl having 1 to 2 heteroatoms, each independently N, O, or S; R$^3$ is H, C$_{1-6}$ alkyl, C$_{1-6}$ alkoxy, C$_{1-6}$ alkoxyalkyl, C$_{1-6}$ haloalkyl, or C$_{1-6}$ haloalkoxy; R$^{3a}$ is absent or C$_{1-6}$ alkyl; alternatively, R$^3$ and R$^{3a}$ are combined to form a 3 to 8 membered heterocycloalkyl having 1 to 2 heteroatoms, each independently N, O, or S; subscripts m and p are each independently 0 to 2; and subscripts n and r are each independently 0 to 3.

In another embodiment, provided herein is a compound, or a pharmaceutically acceptable salt thereof, having a structure of Formula (J):

(J)

wherein: each R$^{1a}$, R$^{1b}$, R$^{1c}$, and R$^{1d}$ is independently H, C$_{1-6}$ alkyl, C$_{2-6}$ alkenyl, C$_{2-6}$ alkynyl, C$_{1-6}$ alkoxy, C$_{1-6}$ alkoxyalkyl, halogen, C$_{1-6}$ haloalkyl, C$_{1-6}$ haloalkoxy, —NO$_2$, or —CN; alternatively, two R$^{1a}$ groups on adjacent ring atoms are combined to form a C$_{4-8}$ cycloalkyl or 4 to 8 membered heterocycloalkyl having 1 to 2 heteroatoms, each independently N, O, or S; R$^{2a}$ and R$^{2b}$ are each independently H, C$_{1-6}$ alkyl, C$_{3-6}$ cycloalkyl, C$_{1-6}$ alkoxy, C$_{1-6}$ alkoxyalkyl, C$_{1-6}$ haloalkyl, or C$_{1-6}$ haloalkoxy; alternatively, R$^{2a}$ and R$^{2b}$ are combined to form a 4 to 8 membered heterocycloalkyl having 1 to 2 heteroatoms, each independently N, O, or S; R$^3$ is H, C$_{1-6}$ alkyl, C$_{1-6}$ alkoxy, C$_{1-6}$ alkoxyalkyl, C$_{1-6}$ haloalkyl, or C$_{1-6}$ haloalkoxy; subscripts m and p are each independently 0 to 2; and subscripts n and r are each independently 0 to 3.

In another embodiment, the present invention provides a crystalline compound of (7aS,10R)-10-(diethylcarbamoyl)-8,8-dimethyl-7a,8,9,10-tetrahydro-7H-indolo[7,1-fg][1,7]naphthyridin-8-ium iodide having the following structure:

characterized by unit cell dimensions of a=7.0716(6) Å, α=90°, b=14.4326(12) Å, β=90°, c=23.0876(19) Å, and γ=90°.

In another embodiment, provided herein is a pharmaceutical composition, comprising a therapeutically effective amount of a compound of the present invention, or a pharmaceutically acceptable salt thereof.

In another embodiment, provided herein is a method of treating a disease, comprising administering to a subject in need thereof, a therapeutically effective amount of a compound of the present invention, or a pharmaceutically acceptable salt thereof, thereby treating the disease.

In another embodiment, provided herein is a method for increasing neural plasticity, the method comprising contacting a neuronal cell with a compound of the present invention, or a pharmaceutically acceptable salt thereof, in an amount sufficient to increase neural plasticity of the neuronal cell, wherein the compound produces a maximum number of dendritic crossings with an increase of greater than 1.0 fold by a Sholl Analysis.

In another embodiment, provided herein is a method for increasing neural plasticity and increasing dendritic spine density, the method comprising contacting a neuronal cell with a compound of the present invention, or a pharmaceutically acceptable salt thereof, in an amount sufficient to increase neural plasticity and increase dendritic spine density of the neuronal cell.

BRIEF DESCRIPTION OF THE DRAWINGS

Figure 1:
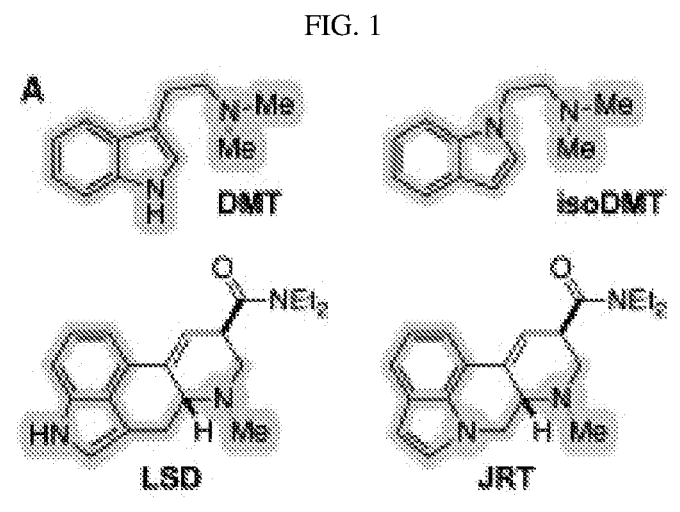

FIG. 1 shows the structural basis for the rational design of JRT, including the comparison between the structures of N,N-dimethyltryptamine and LSD with N,N-dimethyl-isotryptamine and JRT.

Figure 3E:
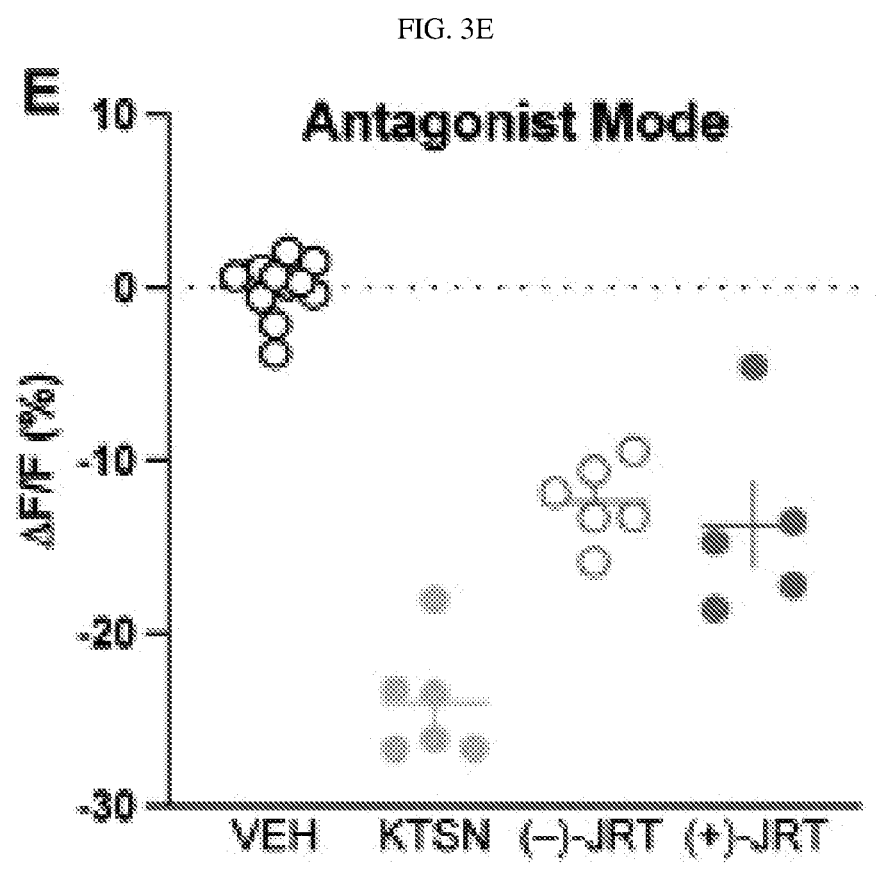

FIG. 3A to FIG. 3E shows (+)-JRT is highly selective for serotonin receptors. FIG. 3A shows the binding profiles of (+)-JRT and (−)-JRT compared to (+)-LSD. Orange and white cells indicate $K_i$ values that are less than or greater than 10 μM, respectively. FIG. 3B shows the traditional GPCR binding and functional assays indicate that (+)-JRT is a potent agonist of 5-HT2 receptors. FIG. 3C to FIG. 3E shows the PsychLight assays indicate that (+)-JRT and (−)-JRT have low hallucinogenic potential. FIG. 3C shows representative images of PSYLI2 cells after treatment in agonist mode. FIG. 3D shows concentration-response psychLight assay performed in agonist mode. FIG. 3E shows single concentration psychLight assay (1 μM) performed in antagonist mode.

FIG. 5A to FIG. 5D shows (+)-JRT exhibits antipsychotic, antidepressant, and pro-cognitive effects in vivo. FIG. 5A shows mouse head-twitch response (HTR) assays in male and female animals demonstrate that (+)-JRT has low hallucinogenic potential when the assay is run in agonist mode. Furthermore, (+)-JRT (1 mg/kg) demonstrates antipsychotic properties by antagonizing a HTR induced by LSD (0.2 mg/kg). FIG. 5B shows pretreatment with (+)-JRT (1 mg/kg) can block AMPH-induced hyperlocomotion in female, but not male, mice. FIG. 5C shows a rat FST conducted 24 h after compound administration demonstrates that (+)-JRT produces antidepressant-like effects comparable to ketamine at substantially lower doses. Doses (mg/mL) are indicated within or above the bars representing various treatment groups. FIG. 5D shows a 4-odor discrimination and reversal assay demonstrates that (+)-JRT does not impact stimulus discrimination but rescues cognitive deficits induced by unpredictable mild stress. AMPH=D-amphetamine.

FIG. 6 shows selectivity profiles for (+)-JRT and (−)-JRT across 55 central nervous system targets. The effects of (+)-JRT (10 μM) and (−)-JRT (10 μM) on a wide range of targets was assessed by Eurofins Discovery. Assays were conducted in duplicate and the results were averaged. Targets with ≥50% inhibition are highlighted in blue.

FIG. 11 shows X-Ray Crystal Structure of 16. One molecule of 16 and one solvent molecule of DCM are present. Atomic numbering matches the provided atomic coordinates.

DETAILED DESCRIPTION OF THE INVENTION

I. General

Figure 2:
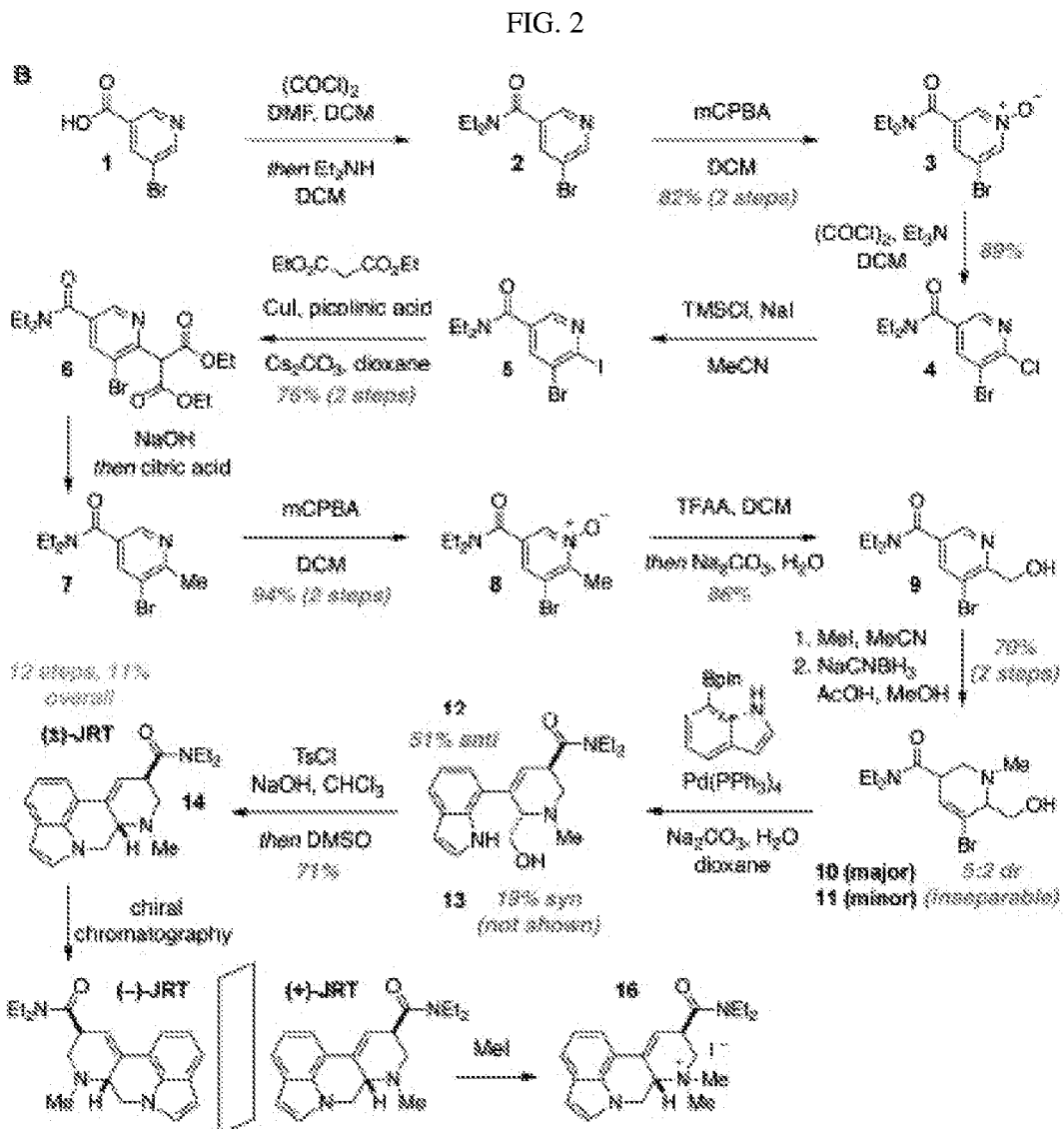
FIG. 2 shows the total synthesis of (±)-JRT was completed in 12 steps and 11% overall yield.
Figures 3A, 3B:
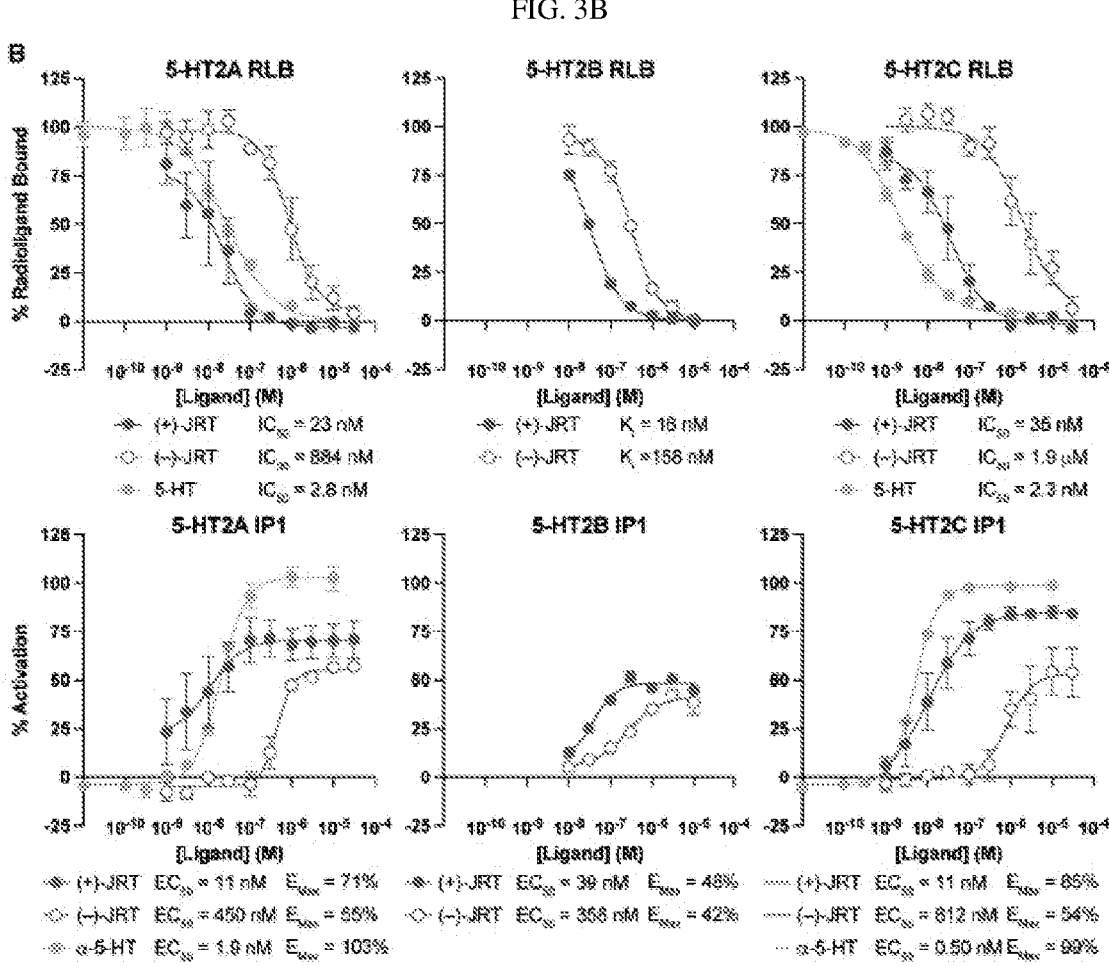
Figure 3C:
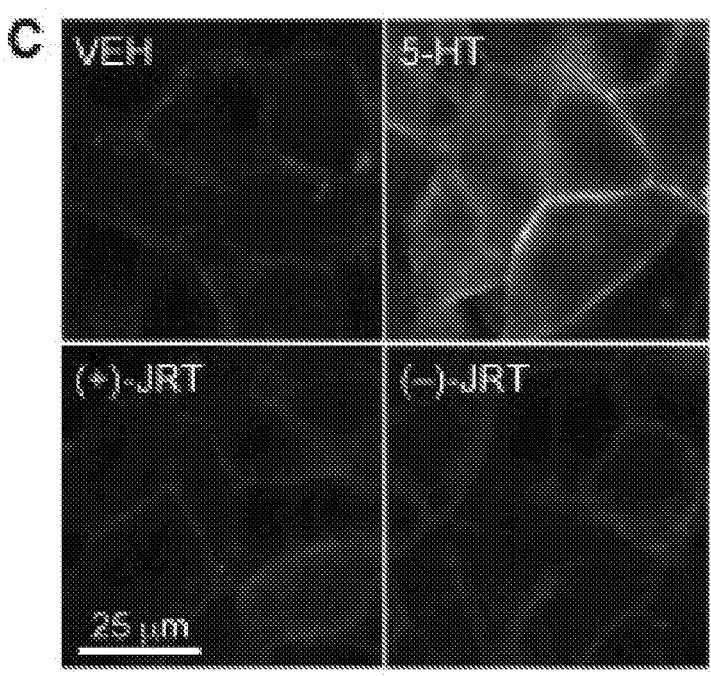
Figure 3D:
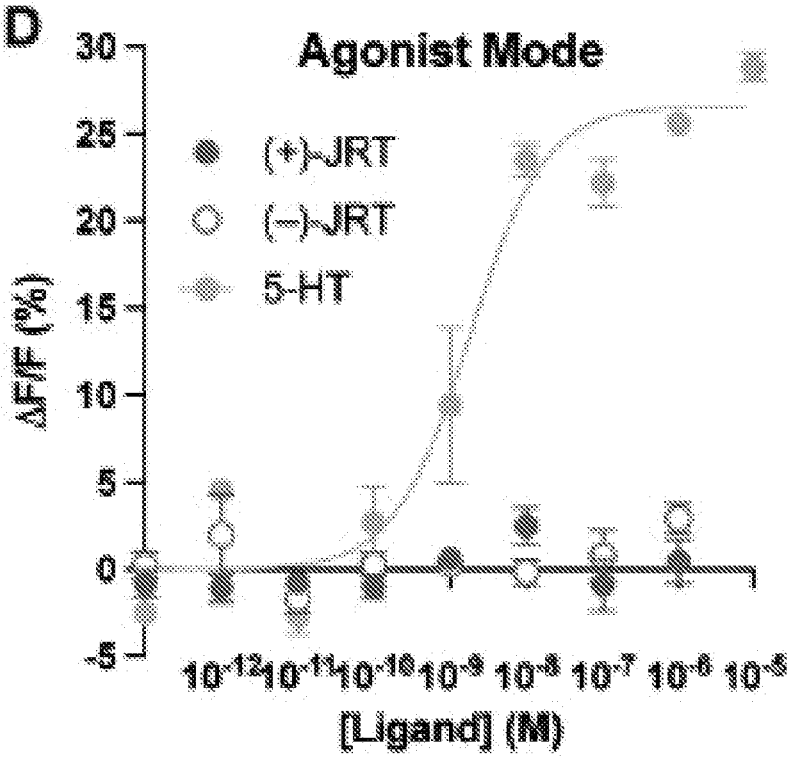
Figure 4:
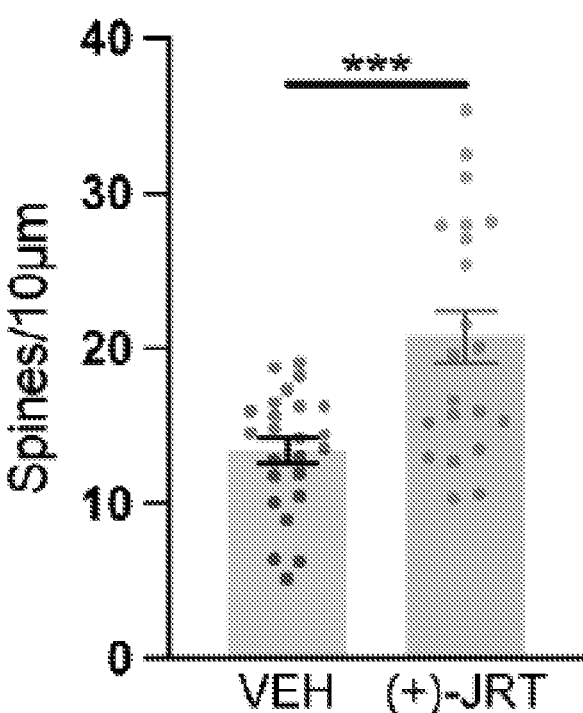
FIG. 4 shows (+)-JRT promotes structural plasticity in vivo. Electron microscopy was used to demonstrate that a single dose of (+)-JRT (1 mg/kg) increases dendritic spine density in the PFC 24 h after administration. Data represent spines counted on 5-8 dendritic segments per animal with 3 animals per group.
Figure 5B:
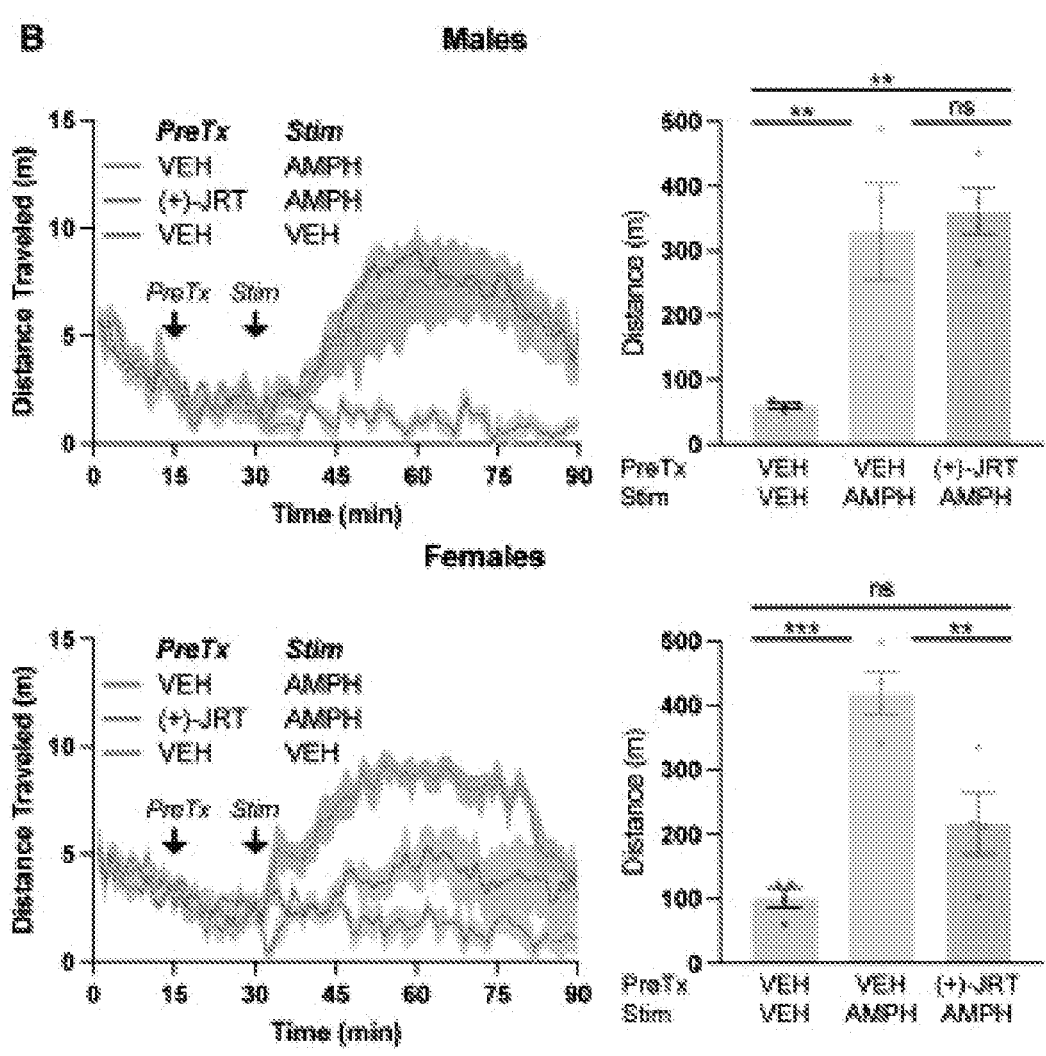
Figure 5C:
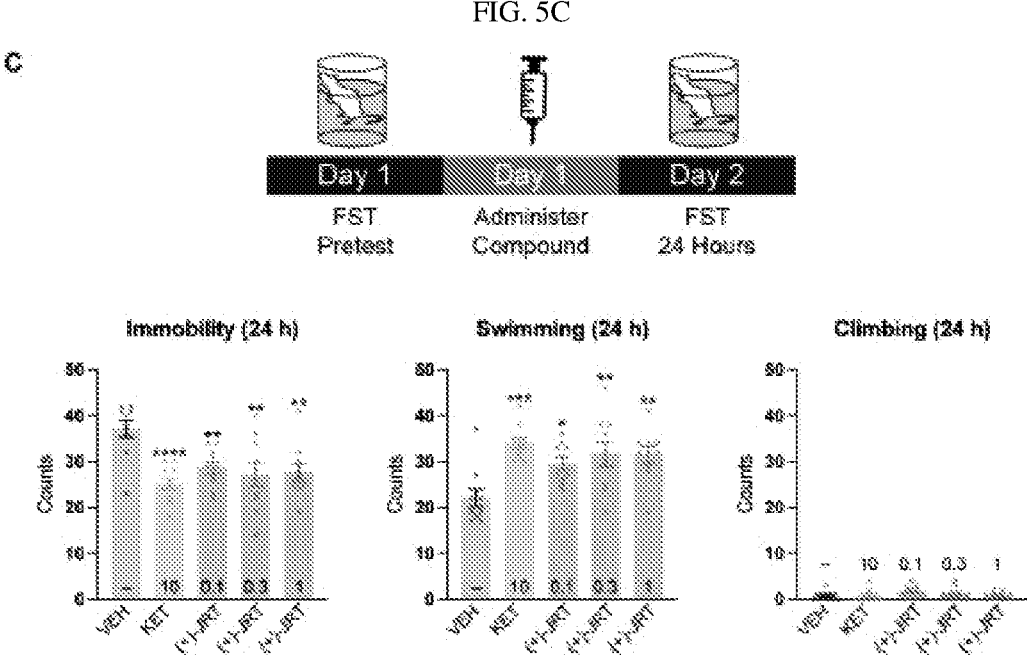
Figure 5D:
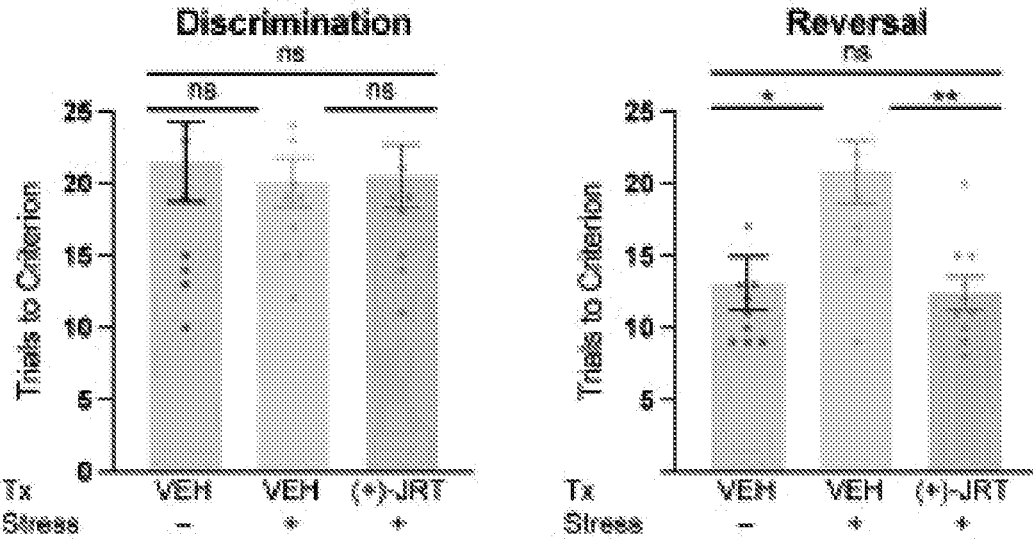

Provided herein are tetracyclic ergoline analogs of heterocyclic compounds. The compounds of the present invention are useful for treatment of diseases, such as brain disorders, neuropsychiatric diseases, and other neurological diseases. The compounds of the present invention are also useful for increasing neural plasticity, increasing dendritic spine density, or both.

II. Definitions

Unless specifically indicated otherwise, all technical and scientific terms used herein have the same meaning as commonly understood by those of ordinary skill in the art to which this invention belongs. In addition, any method or material similar or equivalent to a method or material described herein can be used in the practice of the present invention. For purposes of the present invention, the following terms are defined.

"A," "an," or "the" not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

"Alkyl" refers to a straight or branched, saturated, aliphatic radical having the number of carbon atoms indicated.

Disclosures provided herein of an "alkyl" are intended to include independent recitations of a saturated alkyl, unless otherwise stated. Alkyl groups described herein are generally monovalent, but may also be divalent which may also be described herein as "alkylene" or "alkylenyl" groups. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc. Alkyl groups can be substituted or unsubstituted.

"Alkenyl" refers to a straight chain or branched hydrocarbon having at least 2 carbon atoms and at least one double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can be substituted or unsubstituted.

"Alkynyl" refers to either a straight chain or branched hydrocarbon having at least 2 carbon atoms and at least one triple bond. Alkynyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Examples of alkynyl groups include, but are not limited to, acetylenyl, propynyl, 1-butynyl, 2-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can be substituted or unsubstituted.

"Alkoxy" refers to an alkyl group having an oxygen atom that connects the alkyl group to the point of attachment: alkyl-O—. As for alkyl group, alkoxy groups can have any suitable number of carbon atoms, such as $C_{1-6}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. Alkoxy groups can be substituted or unsubstituted.

"Alkoxyalkyl" refers to a radical having an alkyl component and an alkoxy component, where the alkyl component links the alkoxy component to the point of attachment. The alkyl component is as defined above, except that the alkyl component is at least divalent, an alkylene, to link to the alkoxy component and to the point of attachment. The alkyl component can include any number of carbons, such as $C_{0-6}$, $C_{1-2}$, $C_{1-3}$, $C_{1-4}$, $C_{1-5}$, $C_{1-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. In some instances, the alkyl component can be absent. The alkoxy component is as defined above. Examples of the alkoxyalkyl group include, but are not limited to, 2-ethoxy-ethyl and methoxymethyl.

"Halogen" refers to fluorine, chlorine, bromine and iodine.

"Haloalkyl" refers to alkyl, as defined above, where some or all of the hydrogen atoms are replaced with halogen atoms. As for alkyl group, haloalkyl groups can have any suitable number of carbon atoms, such as $C_{1-6}$. For example, haloalkyl includes trifluoromethyl, flouromethyl, etc. In some instances, the term "perfluoro" can be used to define a compound or radical where all the hydrogens are replaced with fluorine. For example, perfluoromethyl refers to 1,1,1-trifluoromethyl.

"Haloalkoxy" refers to an alkoxy group where some or all of the hydrogen atoms are substituted with halogen atoms. As for an alkyl group, haloalkoxy groups can have any suitable number of carbon atoms, such as $C_{1-6}$. The alkoxy groups can be substituted with 1, 2, 3, or more halogens. When all the hydrogens are replaced with a halogen, for example by fluorine, the compounds are per-substituted, for example, perfluorinated. Haloalkoxy includes, but is not limited to, trifluoromethoxy, 2,2,2,-trifluoroethoxy, perfluoroethoxy, etc.

"Cycloalkyl" refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. In some embodiments, cycloalkyls are spirocyclic or bridged compounds. In some embodiments, cycloalkyls are optionally fused with an aromatic ring, and the point of attachment is at a carbon that is not an aromatic ring carbon atom. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_{3-8}$ cycloalkyl, exemplary groups include, but are not limited to cyclopropyl, cyclobutyl, cyclopentyl, cyclohexyl, cycloheptyl and cyclooctyl. When cycloalkyl is a saturated monocyclic $C_{3-6}$ cycloalkyl, exemplary groups include, but are not limited to cyclopropyl, cyclobutyl, cyclopentyl, and cyclohexyl. Cycloalkyl groups can be substituted or unsubstituted. Cycloalkyl groups can contain one or more double bonds in the ring.

"Heterocycloalkyl" refers to a saturated ring system having from 3 to 12 ring members and from 1 to 4 heteroatoms of N, O and S. The heteroatoms can also be oxidized, such as, but not limited to, —S(O)— and —S(O)$_2$—. Heterocycloalkyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. In some embodiments, heterocycloalkyls are spirocyclic or bridged compounds. In some embodiments, heterocycloalkyls are optionally fused with an aromatic ring, and the point of attachment is at a carbon or heteroatom (e.g., nitrogen atom) that is not an aromatic ring carbon atom. The heterocycloalkyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. The heterocycloalkyl groups can also be fused to aromatic or non-aromatic ring systems to form members including, but not limited to, indoline. Heterocycloalkyl groups can be unsubstituted or substituted. For example, heterocycloalkyl groups can be substituted with $C_{1-6}$ alkyl or oxo (=O), among many others.

The heterocycloalkyl groups can be linked via any position on the ring. For example, aziridine can be 1- or 2-aziridine, azetidine can be 1- or 2-azetidine, pyrrolidine can be 1-, 2- or 3-pyrrolidine, piperidine can be 1-, 2-, 3- or 4-piperidine, pyrazolidine can be 1-, 2-, 3-, or 4-pyrazolidine, imidazolidine can be 1-, 2-, 3- or 4-imidazolidine, piperazine can be 1-, 2-, 3- or 4-piperazine, tetrahydrofuran can be 1- or 2-tetrahydrofuran, oxazolidine can be 2-, 3-, 4- or 5-oxazolidine, isoxazolidine can be 2-, 3-, 4- or 5-isoxazolidine, thiazolidine can be 2-, 3-, 4- or 5-thiazolidine, isothiazolidine can be 2-, 3-, 4- or 5-isothiazolidine, and morpholine can be 2-, 3- or 4-morpholine.

When heterocycloalkyl includes 3 to 8 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxzoalidine, thiazolidine, isothiazolidine, morpholine, thiomorpholine, dioxane and dithiane. Heterocycloalkyl can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

"Heterocycle" or "heterocyclic" refers to heteroaromatic rings (also known as heteroaryls) and heterocycloalkyl rings (also known as heteroalicyclic groups) containing one to four heteroatoms in the ring(s), where each heteroatom in the ring(s) is selected from O, S and N, wherein each heterocyclic group has from 3 to 10 atoms in its ring system, and with the proviso that any ring does not contain two adjacent O or S atoms. Unless stated otherwise specifically in the specification, the heterocyclyl radical is a monocyclic, bicyclic, tricyclic or tetracyclic ring system, which optionally includes fused or bridged ring systems. The heteroatoms in the heterocyclyl radical are optionally oxidized. One or more nitrogen atoms, if present, are optionally quaternized. The heterocyclyl radical is partially or fully saturated. The heterocyclyl is attached to the rest of the molecule through any atom of the ring(s). Non-aromatic heterocyclic groups (also known as heterocycloalkyls) include rings having 3 to 10 atoms in its ring system and aromatic heterocyclic groups include rings having 5 to 10 atoms in its ring system. The heterocyclic groups include benzo-fused ring systems. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, indolin-2-onyl, isoindolin-1-onyl, isoindoline-1,3-dionyl, 3,4-dihydroisoquinolin-1(2H)-onyl, 3,4-dihydroquinolin-2(1H)-onyl, isoindoline-1,3-dithionyl, benzo[d]oxazol-2(3H)-onyl, 1H-benzo[d]imidazol-2(3H)-onyl, benzo[d]thiazol-2(3H)-onyl, and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups are either C-attached (or C-linked) or N-attached where such is possible. For instance, a group derived from pyrrole includes both pyrrol-1-yl (N-attached) or pyrrol-3-yl (C-attached). Further, a group derived from imidazole includes imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles are optionally substituted with one or two oxo (=O) moieties, such as pyrrolidin-2-one. In some embodiments, at least one of the two rings of a bicyclic heterocycle is aromatic. In some embodiments, both rings of a bicyclic heterocycle are aromatic. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^y$—$OR^x$, —$R^y$—OC(O)—$R^x$, —$R^y$—OC(O)—$OR^x$, —$R^y$—OC(O)—N($R^x$)$_2$, —$R^y$—N($R^x$)$_2$, —$R^y$—C(O)$R^x$, —$R^y$—C(O)$OR^x$, —$R^y$—C(O)N($R^x$)$_2$, —$R^y$—O—$R^z$—C(O)N($R^x$)$_2$, —$R^y$—N($R^x$)C(O)$OR^x$, —$R^y$—N($R^x$)C(O)$R^x$, —$R^y$—N($R^x$)S(O)$_t$$R^x$ (where t is 1 or 2), —$R^y$—S(O)$_t$$R^x$ (where t is 1 or 2), —$R^y$—S(O)$_t$$OR^x$ (where t is 1 or 2) and —$R^y$—S(O)$_t$N($R^x$)$_2$ (where t is 1 or 2), where each $R^x$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^y$ is independently a direct bond or a straight or branched alkylene or alkenylene chain, and $R^z$ is a straight or branched alkylene or alkenylene chain, and where each of the above substituents is unsubstituted unless otherwise indicated.

"Salt" refers to acid or base salts of the compounds used in the methods of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

Pharmaceutically acceptable salts of the acidic compounds of the present invention are salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts.

Similarly acid addition salts, such as of mineral acids, organic carboxylic and organic sulfonic acids, e.g., hydrochloric acid, methanesulfonic acid, maleic acid, are also possible provided a basic group, such as pyridyl, constitutes part of the structure.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

"Therapeutically effective amount or dose" or "therapeutically sufficient amount or dose" or "effective or sufficient amount or dose" refer to a dose that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins). In sensitized cells, the therapeutically effective dose can often be lower than the conventional therapeutically effective dose for non-sensitized cells.

"Treat", "treating" and "treatment" refers to any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; or, in some situations, preventing the onset of the symptom. The treatment or amelioration of symptoms can be based on any objective or subjective parameter; including, e.g., the result of a physical examination.

"Disease" refers abnormal cellular function in an organism, which is not due to a direct result of a physical or external injury. Diseases can refer to any condition that causes distress, dysfunction, disabilities, disorders, infections, pain, or even death. Diseases include, but are not limited to hereditary diseases such as genetic and non-genetic diseases, infectious diseases, non-infectious diseases such as cancer, deficiency diseases, neurological diseases, and physiological diseases.

"Administering" refers to oral administration, administration as a suppository, topical contact, parenteral, intravenous, intraperitoneal, intramuscular, intralesional, intranasal or subcutaneous administration, intrathecal administration, or the implantation of a slow-release device e.g., a mini-osmotic pump, to the subject.

"Subject" refers to animals such as mammals, including, but not limited to, primates (e.g., humans), cows, sheep, goats, horses, dogs, cats, rabbits, rats, mice and the like. In certain embodiments, the subject is a human.

"Neural plasticity" refers to the ability of the brain to change its structure and/or function continuously throughout a subject's life. Examples of the changes to the brain include, but are not limited to, the ability to adapt or respond to internal and/or external stimuli, such as due to an injury, and the ability to produce new neurites, dendritic spines, and synapses.

"Dendritic crossing" refers to dendritic branches which overlap each other or form a cluster. Dendritic crossing can be measured by Sholl Analysis.

"Dendritic spine" refers to the small membrane protruding from a dendrite which can receive electric signal from an axon at the synapse. Dendritic spines are useful for transmitting electric signals to the neuron's cell body. Dendrites of a single neuron can comprise hundreds to thousands of spines. Dendritic spine density refers to the number of spines within the length of a dendrite. As an illustrative example, a dendritic spine density of 5 $\mu m^{-1}$ indicates 5 spines per 1 $\mu m$ stretch of a dendrite.

"Modulate" or "modulating" or "modulation" refers to an increase or decrease in the amount, quality, or effect of a particular activity, function or molecule. By way of illustration and not limitation, agonists, partial agonists, antagonists, and allosteric modulators (e.g., a positive allosteric modulator) of a G protein-coupled receptor (e.g., $5HT_{2A}$ or $5HT_{2C}$) are modulators of the receptor.

"Agonism" refers to the activation of a receptor or enzyme by a modulator, or agonist, to produce a biological response.

"Agonist" refers to a modulator that binds to a receptor or enzyme and activates the receptor to produce a biological response. By way of example only, "$5HT_{2A}$ agonist" can be used to refer to a compound that exhibits an $EC_{50}$ with respect to $5HT_{2A}$ activity of no more than about 100 $\mu M$. In some embodiments, the term "agonist" includes full agonists or partial agonists. "Full agonist" refers to a modulator that binds to and activates a receptor with the maximum response that an agonist can elicit at the receptor. "Partial agonist" refers to a modulator that binds to and activates a given receptor, but has partial efficacy, that is, less than the maximal response, at the receptor relative to a full agonist. "Functionally selective agonist" refers to a modulator that produces one or a subset of biological responses that are possible from activation of a receptor. For example, activation of $5HT_{2A}$ receptors is known to cause many downstream effects including increased neural plasticity, increased intracellular calcium concentrations, and hallucinations, among many other biological responses. A functionally selective agonist would produce only a subset of the biological responses possible from activation of the $5HT_{2A}$ receptor.

"Positive allosteric modulator" refers to a modulator that binds to a site distinct from the orthosteric binding site and enhances or amplifies the effect of an agonist.

"Antagonism" refers to the inactivation of a receptor or enzyme by a modulator, or antagonist. Antagonism of a receptor, for example, is when a molecule binds to the receptor and does not allow activity to occur. "Functionally selective antagonists" block one signaling pathway while leaving others in tact.

"Antagonist" or "neutral antagonist" refers to a modulator that binds to a receptor or enzyme and blocks a biological response. An antagonist has no activity in the absence of an agonist or inverse agonist but can block the activity of either, causing no change in the biological response.

III. Compounds

The present invention provides tetracyclic heterocyclic compounds useful for the treatment of a variety of neurological diseases and disorders as well as increasing neuronal plasticity.

In some embodiments, the compounds provided herein have improved physiochemical properties as a result of the loss of a hydrogen bond donor, decreasing total polar surface area and improving central nervous system multiparameter optimization (MPO) scores. Described herein in some embodiments are non-hallucinogenic compounds that demonstrate similar therapeutic potential as hallucinogenic 5-HT modulators (e.g., $5HT_{2A}$ and/or $5HT_{2C}$ modulators). In some embodiments, the non-hallucinogenic compounds described herein provide better therapeutic potential than hallucinogenic 5-HT modulators (e.g., $5HT_{2A}$ and/or $5HT_{2C}$ modulators) for neurological diseases.

Provided herein is a heterocyclic compound useful for the treatment of a variety of diseases such as brain disorders and other conditions. In some embodiments, the heterocyclic compounds provided herein are $5\text{-HT}_2$ modulators and promote neural plasticity (e.g., cortical structural plasticity).

In some embodiments, provided herein is a compound, or a pharmaceutically acceptable salt thereof, having a structure of Formula (K):

(K)

wherein: each $R^{1a}$, $R^{1b}$, $R^{1c}$, and $R^{1d}$ is independently H, $C_{1-6}$ alkyl, $C_{2-6}$ alkenyl, $C_{2-6}$ alkynyl, $C_{1-6}$ alkoxy, $C_{1-6}$ alkoxyalkyl, halogen, $C_{1-6}$ haloalkyl, $C_{1-6}$ haloalkoxy, —$NO_2$, or —CN; alternatively, two $R^{1a}$ groups on adjacent ring atoms are combined to form a $C_{4-8}$ cycloalkyl or 4 to 8 membered heterocycloalkyl having 1 to 2 heteroatoms, each independently N, O, or S; $R^{2a}$ and $R^{2b}$ are each independently H, $C_{1-6}$ alkyl, $C_{3-6}$ cycloalkyl, $C_{1-6}$ alkoxy, $C_{1-6}$ alkoxyalkyl, $C_{1-6}$ haloalkyl, or $C_{1-6}$ haloalkoxy; alternatively, $R^{2a}$ and $R^{2b}$ are combined to form a 4 to 8 membered heterocycloalkyl having 1 to 2 heteroatoms, each independently N, O, or S; $R^3$ is H, $C_{1-6}$ alkyl, $C_{1-6}$ alkoxy, $C_{1-6}$ alkoxyalkyl, $C_{1-6}$ haloalkyl, or $C_{1-6}$ haloalkoxy; $R^{3a}$ is absent or $C_{1-6}$ alkyl; alternatively, $R^3$ and $R^{3a}$ are combined to form a 3 to 8 membered heterocycloalkyl having 1 to 2 heteroatoms, each independently N, O, or S; subscripts m and p are each independently 0 to 2; and subscripts n and r are each independently 0 to 3.

In some embodiments, provided herein is a compound, or a pharmaceutically acceptable salt thereof, having a structure of Formula (J):

(J)

wherein: each $R^{1a}$, $R^{1b}$, $R^{1c}$, and $R^{1d}$ is independently H, $C_{1-6}$ alkyl, $C_{2-6}$ alkenyl, $C_{2-6}$ alkynyl, $C_{1-6}$ alkoxy, $C_{1-6}$ alkoxyalkyl, halogen, $C_{1-6}$ haloalkyl, $C_{1-6}$ haloalkoxy, —$NO_2$, or —CN; alternatively, two $R^{1a}$ groups on adjacent ring atoms are combined to form a $C_{4-8}$ cycloalkyl or 4 to 8 membered heterocycloalkyl having 1 to 2 heteroatoms, each independently N, O, or S; $R^{2a}$ and $R^{2b}$ are each independently H, $C_{1-6}$ alkyl, $C_{3-6}$ cycloalkyl, $C_{1-6}$ alkoxy, $C_{1-6}$ alkoxyalkyl, $C_{1-6}$ haloalkyl, or $C_{1-6}$ haloalkoxy; alternatively, $R^{2a}$ and $R^{2b}$ are combined to form a 4 to 8 membered heterocycloalkyl having 1 to 2 heteroatoms, each independently N, O, or S; $R^3$ is H, $C_{1-6}$ alkyl, $C_{1-6}$ alkoxy, $C_{1-6}$ alkoxyalkyl, $C_{1-6}$ haloalkyl, or $C_{1-6}$ haloalkoxy; subscripts m and p are each independently 0 to 2; and subscripts n and r are each independently 0 to 3.

In some embodiments, provided herein is a compound, or a pharmaceutically acceptable salt thereof, having a structure of Formula (I):

(I)

In some embodiments, provided herein is a compound, or a pharmaceutically acceptable salt thereof, having a structure of Formula (Ia), Formula (Ib), Formula (Ic), or Formula (Id):

(Ia)

-continued (Ib)

(Ic)

(Id)

In some embodiments, provided herein is a compound having a structure of Formula (Ia):

(Ia)

In some embodiments, provided herein is a compound having a structure of Formula (Ib):

(Ib)

In some embodiments, provided herein is a compound having a structure of Formula (Ic):

(Ic)

In some embodiments, provided herein is a compound having a structure of Formula (Id):

(Id)

$R^{1a}$ can be any suitable functional group. In some embodiments, $R1^{1a}$ is H, $C_{1-6}$ alkyl, $C_{2-6}$ alkenyl, $C_{2-6}$ alkynyl, $C_{1-6}$ alkoxy, $C_{1-6}$ alkoxyalkyl, halogen, $C_{1-6}$ haloalkyl, $C_{1-6}$ haloalkoxy, —$NO_2$, or —CN. In some embodiments, $R^{1a}$ is H, $C_{1-6}$ alkyl, $C_{1-6}$ alkoxy, or halogen. In some embodiments, $R^{1a}$ is H, $C_{1-6}$ alkoxy, or halogen. In some embodiments, $R^{1a}$ is H.

$R^{2a}$ and $R^{2b}$ can be any suitable functional group. In some embodiments, $R^{2a}$ and $R^{2b}$ are each independently H, $C_{1-6}$ alkyl, $C_{3-6}$ cycloalkyl, $C_{1-6}$ alkoxy, $C_{1-6}$ alkoxyalkyl, $C_{1-6}$ haloalkyl, or $C_{1-6}$ haloalkoxy; alternatively, $R^{2a}$ and $R^{2b}$ are combined to form a 4 to 8 membered heterocycloalkyl having 1 to 2 heteroatoms, each independently N, O, or S. In some embodiments, $R^{2a}$ and $R^{2b}$ are each independently H, $C_{1-6}$ alkyl, $C_{3-6}$ cycloalkyl, $C_{1-6}$ alkoxyalkyl, or $C_{1-6}$ haloalkyl. In some embodiments, $R^{2a}$ and $R^{2b}$ are each independently H or $C_{1-6}$ alkyl. In some embodiments, $R^{2a}$ and $R^{2b}$ are each independently $C_{1-6}$ alkyl. In some embodiments, $R^{2a}$ and $R^{2b}$ are each independently ethyl.

$R^3$ can be any suitable functional group. In some embodiments, $R^3$ is H, $C_{1-6}$ alkyl, $C_{1-6}$ alkoxy, $C_{1-6}$ alkoxyalkyl, $C_{1-6}$ haloalkyl, or $C_{1-6}$ haloalkoxy. In some embodiments, $R^3$ is H or $C_{1-6}$ alkyl. In some embodiments, $R^3$ is $C_{1-6}$ alkyl. In some embodiments, $R^3$ is methyl.

In some embodiments, $R^{3a}$ can be absent or $C_{1-6}$ alkyl. In some embodiments, $R^{3a}$ is absent. In some embodiments, $R^{3a}$ is $C_{1-6}$ alkyl. In some embodiments, $R^{3a}$ is methyl.

Subscripts m, n, p, and r can be any suitable integer. In some embodiments, subscripts m and p are each independently 0 to 2; and subscripts n and r are each independently 0 to 3. In some embodiments, n is 0.

In some embodiments, provided herein is a compound or a pharmaceutically acceptable salt thereof, having the following structure:

In some embodiments, provided herein is a compound having the following structure:

In some embodiments, provided herein is a compound or a pharmaceutically acceptable salt thereof, having the following structure:

In some embodiments, provided herein is a compound or a pharmaceutically acceptable salt thereof, having the following structure:

In some embodiments, provided herein is a compound having the following structure:

In some embodiments, provided herein is a compound or a pharmaceutically acceptable salt thereof, having the following structure:

In some embodiments, provided herein is a compound having the following structure:

In some embodiments, provided herein is a compound or a pharmaceutically acceptable salt thereof, having the following structure:

In some embodiments, provided herein is a compound or a pharmaceutically acceptable salt thereof, having the following structure:

In some embodiments, provided herein is a compound having the following structure:

In some embodiments, the present invention provides a crystalline compound of (7aS,10R)-10-(diethylcarbamoyl)-8,8-dimethyl-7a,8,9,10-tetrahydro-7H-indolo[7,1-fg][1,7] naphthyridin-8-ium iodide having the following structure:

characterized by unit cell dimensions of a=7.0716(6) Å, α=90°, b=14.4326(12) Å, β=90°, c=23.0876(19) Å, and γ=90°.

The compounds of the present invention can also be in the salt forms, such as acid or base salts of the compounds of the present invention. Illustrative examples of pharmaceutically acceptable salts are mineral acid (hydrochloric acid, hydrobromic acid, phosphoric acid, and the like) salts, organic acid (fumaric acid, acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

The present invention also includes isotopically-labeled compounds of the present invention, wherein one or more atoms are replaced by one or more atoms having specific atomic mass or mass numbers. Examples of isotopes that can be incorporated into compounds of the invention include, but are not limited to, isotopes of hydrogen, carbon, nitrogen, oxygen, fluorine, sulfur, and chlorine (such as $^{2}$H, $^{3}$H, $^{13}$C, $^{14}$C, $^{15}$N, $^{18}$O, $^{17}$O, $^{18}$F, $^{35}$S and $^{36}$Cl). Isotopically-labeled compounds of the present invention are useful in assays of the tissue distribution of the compounds and their prodrugs and metabolites; preferred isotopes for such assays include $^{3}$H and $^{14}$C. In addition, in certain circumstances substitution with heavier isotopes, such as deuterium ($^{2}$H), can provide increased metabolic stability, which offers therapeutic advantages such as increased in vivo half-life or reduced dosage requirements. Isotopically-labeled compounds of this invention can generally be prepared according to the methods known by one of skill in the art by substituting an isotopically-labeled reagent for a non-isotopically labeled reagent. Compounds of the present invention can be isotopically labeled at positions adjacent to the basic amine, in aromatic rings, and the methyl groups of methoxy substituents.

The present invention includes all tautomers and stereoisomers of compounds of the present invention, either in admixture or in pure or substantially pure form. The compounds of the present invention can have asymmetric centers at the carbon atoms, and therefore the compounds of the present invention can exist in diastereomeric or enantiomeric forms or mixtures thereof. All conformational isomers (e.g., cis and trans isomers) and all optical isomers (e.g., enantiomers and diastereomers), racemic, diastereomeric and other mixtures of such isomers, as well as solvates, hydrates, isomorphs, polymorphs and tautomers are within the scope of the present invention. Compounds according to the present invention can be prepared using diastereomers, enantiomers or racemic mixtures as starting materials. Furthermore, diastereomer and enantiomer products can be separated by chromatography, fractional crystallization or other methods known to those of skill in the art.

5-HT

5-HT$_2$ agonism has been correlated with the promotion of neural plasticity (Ly et al., 2018). 5-HT$_2$ antagonists abrogate the neuritogenesis and spinogenesis effects of hallucinogenic compounds with 5-HT$_2$ agonist activity, e.g., DMT, LSD, and DOI. Furthermore, DMT and other psychedelic compounds promote increased dendritic arbor complexity, dendritic spine density, and synaptogenesis through a 5-HT$_2$-dependent process. Importantly, the psychoplastogenic effects of compounds provided herein are also blocked under these conditions, implicating the 5-HT$_2$ receptor in their mechanism of action. In addition, modulation of the 5-HT$_2$ receptor appears to be important in neuroplasticity as well as various psychological conditions, such as, for example, anxiety, depression, post-traumatic stress disorder (PTSD), and schizophrenia.

Furthermore, non-hallucinogenic compounds (e.g., lisuride and 6-MeO-DMT) compete off 5-HT when an 5HT$_{2A}$ sensor assay is run in antagonist mode. Additionally, compounds, such as, for example, 6-F-DET and Ketanserin, which are non-hallucinogenic in animals (e.g., humans), compete with 5HT binding to 5HT$_{2A}$ in an antagonist mode sensor assay. In some embodiments, a compound provided herein prevents binding of 5-HT to 5HT$_{2A}$. In some embodiments, the 5HT$_{2A}$ sensor assay is in an antagonist mode. In some embodiments, a compound provided herein prevents binding of 5-HT to 5HT$_{2A}$ and has non-hallucinogenic potential. In some embodiments, a compound provided herein prevents binding of 5-HT to 5HT$_{2A}$ and is non-hallucinogenic. In some embodiments, a compound provided herein prevents binding of 5-HT to 5HT$_{2A}$ in antagonist mode has non-hallucinogenic potential. In some embodiments, a compound provided herein prevents binding of 5-HT in antagonist mode is a non-hallucinogenic compound. In some embodiments, a compound provided herein inhibits the response of a sensor assay in antagonist mode has non-hallucinogenic potential. In some embodiments, a compound provided herein inhibits the response of a sensor assay in antagonist mode is a non-hallucinogenic compound.

In some embodiments, the effect of a compound provided herein on an agonist mode sensor assay suggests the compound is a non-hallucinogenic ligand of the 5-HT$_{2A}$ receptor and/or the 5-HT$_{2C}$ receptor. In some embodiments, the effect of a compound provided herein on an antagonist mode sensor assay suggests the compound is a non-hallucinogenic ligand of the 5-HT$_{2A}$ receptor and/or the 5-HT$_{2C}$ receptor. In some embodiments, effect of a compound provided herein on an agonist mode and an antagonist mode sensor assay together suggest the compound is a non-hallucinogenic ligand of the 5-HT$_{2A}$ receptor and/or the 5-HT$_{2C}$ receptor.

Described in some embodiments are non-hallucinogenic compounds that demonstrate similar therapeutic potential as hallucinogenic 5-HT$_2$ agonists. In some embodiments, the non-hallucinogenic compounds described herein provide better therapeutic potential than hallucinogenic 5-HT$_2$ agonists for neurological diseases. In some embodiments, the compounds of the present invention are modulators of the 5-HT$_{2A}$ receptor and/or the 5-HT$_{2C}$ receptor and promote neural plasticity (e.g., cortical structural plasticity).

In some embodiments, the compounds provided herein have activity at the 5-HT$_{2A}$ receptor and/or the 5-HT$_{2C}$ receptor. In some embodiments, the compounds provided herein elicit a biological response by activating the 5-HT$_{2A}$ receptor and/or the 5-HT$_{2C}$ receptor (e.g., allosteric modulation or modulation of a biological target that activates the 5-HT$_{2A}$ receptor and/or the 5-HT$_{2C}$ receptor). In some embodiments, the compounds provided herein are selective 5-HT$_{2A}$ modulators and promote neural plasticity (e.g., cortical structural plasticity). In some embodiments, the compounds provided herein are selective 5-HT$_{2C}$ modulators and promote neural plasticity (e.g., cortical structural plasticity). In some embodiments, promotion of neural plasticity includes, for example, increased dendritic spine growth, increased synthesis of synaptic proteins, strengthened synaptic responses, increased dendritic arbor complexity, increased dendritic branch content, increased spinogenesis, increased neuritogenesis, or any combination thereof. In some embodiments, increased neural plasticity includes, for example, increased cortical structural plasticity in the anterior parts of the brain.

In some embodiments, a compound provided herein (e.g., a 5-HT$_{2A}$ modulator and/or a 5-HT$_{2C}$ modulator) is non-hallucinogenic. In some embodiments, a compound provided herein (e.g., a 5-HT$_{2A}$ modulator and/or a 5-HT$_{2C}$ modulator) is used to treat neurological diseases, which modulators do not elicit dissociative side-effects. In some embodiments, the hallucinogenic potential of the compounds described herein is assessed in vitro. In some embodiments, the hallucinogenic potential assessed in vitro of the compounds described herein is compared to the hallucinogenic potential assessed in vitro of hallucinogenic homologs. In some embodiments, the compounds provided herein elicit less hallucinogenic potential in vitro than the hallucinogenic homologs.

In some embodiments, a compound provided herein (e.g., a 5-HT$_{2A}$ modulator and/or a 5-HT$_{2C}$ modulator) is used to treat neurological diseases. In some embodiments, the neurological diseases comprise decreased neural plasticity, decreased cortical structural plasticity, decreased 5-HT$_{2A}$ receptor content, increased 5-HT$_{2C}$ receptor content, decreased dendritic arbor complexity, loss of dendritic spines, decreased dendritic branch content, decreased spinogenesis, decreased neuritogenesis, retraction of neurites, or any combination thereof.

In some embodiments, a compound provided herein (e.g., a 5-HT$_{2A}$ modulator and/or a 5-HT$_{2C}$ modulator) is used for increasing neuronal plasticity. In some embodiments, a compound provided herein (e.g., a 5-HT$_{2A}$ modulator and/or a 5-HT$_{2C}$ modulator) is used for treating a brain disorder. In some embodiments, a compound provided herein (e.g., a 5-HT$_{2A}$ modulator and/or a 5-HT$_{2C}$ modulator) is used for increasing at least one of translation, transcription, or secretion of neurotrophic factors.

In some embodiments, a compound provided herein, including pharmaceutically acceptable salts and solvates thereof, is a non-hallucinogenic psychoplastogen. In some embodiments, the non-hallucinogenic psychoplastogen promotes neuronal growth, improves neuronal structure, or a combination thereof.

IV. Pharmaceutical Compositions and Formulations

In some embodiments, provided herein is a pharmaceutical composition, comprising a therapeutically effective amount of a compound of the present invention, or a pharmaceutically acceptable salt thereof.

The compositions of the present invention can be prepared in a wide variety of oral, parenteral and topical dosage forms. Oral preparations include tablets, pills, powder, dragees, capsules, liquids, lozenges, cachets, gels, syrups, slurries, suspensions, etc., suitable for ingestion by the patient. The compositions of the present invention can also be administered by injection, that is, intravenously, intramuscularly, intracutaneously, subcutaneously, intraduodenally, or intraperitoneally. Also, the compositions described herein can be administered by inhalation, for example, intranasally. Additionally, the compositions of the present invention can be administered transdermally. The compositions of this invention can also be administered by intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995). Accordingly, the present invention also provides pharmaceutical compositions including a pharmaceutically acceptable carrier or excipient and the compound of the present invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton PA ("Remington's").

In powders, the carrier is a finely divided solid, which is in a mixture with the finely divided active component. In tablets, the active component is mixed with the carrier having the necessary binding properties in suitable proportions and compacted in the shape and size desired. The powders and tablets preferably contain from 5% or 10% to 70% of the compound the present invention.

Suitable solid excipients include, but are not limited to, magnesium carbonate; magnesium stearate; talc; pectin; dextrin; starch; tragacanth; a low melting wax; cocoa butter; carbohydrates; sugars including, but not limited to, lactose, sucrose, mannitol, or sorbitol, starch from corn, wheat, rice, potato, or other plants; cellulose such as methyl cellulose, hydroxypropylmethyl-cellulose, or sodium carboxymethyl-cellulose; and gums including arabic and tragacanth; as well as proteins including, but not limited to, gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain the compound of the present invention mixed with a filler or binders such as lactose or starches, lubricants such as talc or magnesium stearate, and, optionally, stabilizers. In soft capsules, the compound of the present invention may be dissolved or suspended in suitable liquids, such as fatty oils, liquid paraffin, or liquid polyethylene glycol with or without stabilizers.

For preparing suppositories, a low melting wax, such as a mixture of fatty acid glycerides or cocoa butter, is first melted and the compound of the present invention is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the compound of the present invention in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending the compound of the present invention in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compositions of the present invention can also be delivered as microspheres for slow release in the body. For example, microspheres can be formulated for administration via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). Both transdermal and intradermal routes afford constant delivery for weeks or months.

In another embodiment, the compositions of the present invention can be formulated for parenteral administration, such as intravenous (IV) administration or administration into a body cavity or lumen of an organ. The formulations for administration will commonly comprise a solution of the compositions of the present invention dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the formulations of the compositions of the present invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

The compositions of the present invention can be delivered by any suitable means, including oral, parenteral and topical methods. Transdermal administration methods, by a topical route, can be formulated as applicator sticks, solutions, suspensions, emulsions, gels, creams, ointments, pastes, jellies, paints, powders, and aerosols.

The pharmaceutical preparation is preferably in unit dosage form. In such form the preparation is subdivided into unit doses containing appropriate quantities of the compounds of the present invention. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The compound of the present invention can be present in any suitable amount, and can depend on various factors including, but not limited to, weight and age of the subject, state of the disease, etc. Suitable dosage ranges for the compound of the present invention include from about 0.1 mg to about 10,000 mg, or about 1 mg to about 1000 mg, or about 10 mg to about 750 mg, or about 25 mg to about 500 mg, or about 50 mg to about 250 mg. Suitable dosages for the compound of the present invention include about 1 mg, 5, 10, 20, 30, 40, 50, 60, 70, 80, 90, 100, 200, 300, 400, 500, 600, 700, 800, 900 or 1000 mg.

The compounds of the present invention can be administered at any suitable frequency, interval and duration. For example, the compound of the present invention can be administered once an hour, or two, three or more times an hour, once a day, or two, three, or more times per day, or once every 2, 3, 4, 5, 6, or 7 days, so as to provide the preferred dosage level. When the compound of the present invention is administered more than once a day, representative intervals include 5, 10, 15, 20, 30, 45 and 60 minutes, as well as 1, 2, 4, 6, 8, 10, 12, 16, 20, and 24 hours. The compound of the present invention can be administered once, twice, or three or more times, for an hour, for 1 to 6 hours, for 1 to 12 hours, for 1 to 24 hours, for 6 to 12 hours, for 12 to 24 hours, for a single day, for 1 to 7 days, for a single week, for 1 to 4 weeks, for a month, for 1 to 12 months, for a year or more, or even indefinitely.

The composition can also contain other compatible therapeutic agents. The compounds described herein can be used in combination with one another, with other active agents known to be useful in modulating a glucocorticoid receptor, or with adjunctive agents that may not be effective alone, but may contribute to the efficacy of the active agent.

The compounds of the present invention can be co-administered with another active agent. Co-administration includes administering the compound of the present invention and active agent within 0.5, 1, 2, 4, 6, 8, 10, 12, 16, 20, or 24 hours of each other. Co-administration also includes administering the compound of the present invention and active agent simultaneously, approximately simultaneously (e.g., within about 1, 5, 10, 15, 20, or 30 minutes of each other), or sequentially in any order. Moreover, the compound of the present invention and the active agent can each be administered once a day, or two, three, or more times per day so as to provide the preferred dosage level per day.

In some embodiments, co-administration can be accomplished by co-formulation, i.e., preparing a single pharmaceutical composition including both the compound of the present invention and the active agent. In other embodiments, the compound of the present invention and the active agent can be formulated separately.

The compound of the present invention and the active agent can be present in the compositions of the present invention in any suitable weight ratio, such as from about 1:100 to about 100:1 (w/w), or about 1:50 to about 50:1, or about 1:25 to about 25:1, or about 1:10 to about 10:1, or about 1:5 to about 5:1 (w/w). The compound of the present invention and the other active agent can be present in any suitable weight ratio, such as about 1:100 (w/w), 1:50, 1:25, 1:10, 1:5, 1:4, 1:3, 1:2, 1:1, 2:1, 3:1, 4:1, 5:1, 10:1, 25:1, 50:1 or 100:1 (w/w). Other dosages and dosage ratios of the compound of the present invention and the active agent are suitable in the compositions and methods of the present invention.

V. Methods of Treatment

In some embodiments, provided herein is a method of treating a disease or disorder, such as, but not limited to a neurological disease or disorder, comprising administering to a subject in need thereof, a therapeutically effective amount of a compound of the present invention, or a pharmaceutically acceptable salt thereof, thereby treating the disease or disorder.

In some embodiments, provided herein is a method of treating a disease, comprising administering to a subject in need thereof, a therapeutically effective amount of a compound of the present invention, or a pharmaceutically acceptable salt thereof, thereby treating the disease.

Neurological Disorders

Neuronal plasticity, and changes thereof, have been attributed to many neurological diseases and disorders. For example, during development and in adulthood, changes in dendritic spine number and morphology (e.g., lengths, crossings, density) accompany synapse formation, maintenance and elimination; these changes are thought to establish and remodel connectivity within neuronal circuits. Furthermore, dendritic spine structural plasticity is coordinated with synaptic function and plasticity. For example, spine enlargement is coordinated with long-term potentiation in neuronal circuits, whereas long-term depression is associated with spine shrinkage.

In addition, dendritic spines undergo experience-dependent morphological changes in live animals, and even subtle changes in dendritic spines can affect synaptic function, synaptic plasticity, and patterns of connectivity in neuronal circuits. For example, disease-specific disruptions in dendritic spine shape, size, and/or number accompany neurological diseases and disorders, such as, for example, neurodegenerative (e.g., Alzheimer's disease or Parkinson's disease) and neuropsychiatric (e.g., depression or schizophrenia) diseases and disorders, suggesting that dendritic spines may serve as a common substrate in diseases that involve deficits in information processing.

Unless indicated otherwise, a neurological disease or disorder generally refers to a disease or disorder of the central nervous system (CNS) (e.g., brain, spine, and/or nerves) of an individual.

In some embodiments, provided herein is a method of treating a neurological disease or disorder with a compound provided herein (e.g., a compound of Formula (K), Formula (J), Formula (I), Formula (Ia), Formula (Ib), Formula (Ic), Formula (Id), or a pharmaceutically acceptable salt or solvate thereof).

Provided in some instances herein is a compound useful for the treatment of a variety of brain disorders and other conditions. In some embodiments, the compound provided herein is a 5-HT$_{2A}$ modulator and promotes neural plasticity (e.g., cortical structural plasticity). In some embodiments, the 5-HT$_{2A}$ modulator (e.g., 5-HT$_{2A}$ agonists) is used to treat a brain disorder. In some embodiments, a compound provided herein is a 5-HT$_{2C}$ modulator and promotes neural plasticity (e.g., cortical structural plasticity). In some embodiments, the 5-HT$_{2C}$ modulator is used to treat a brain disorder. In some embodiments, the brain disorder comprises decreased neural plasticity, decreased cortical structural plasticity, decreased 5-HT$_{2A}$ receptor content, increased 5-HT$_{2C}$ receptor content, decreased dendritic arbor complexity, loss of dendritic spines, decreased dendritic branch content, decreased spinogenesis, decreased neuritogenesis, retraction of neurites, or any combination thereof.

In one aspect, a compound provided herein (e.g., a compound of Formula (K), Formula (J), Formula (I), Formula (Ia), Formula (Ib), Formula (Ic), Formula (Id), or a pharmaceutically acceptable salt or solvate thereof) improves dendritic spine number and dendritic spine morphology that is lost in a neurological disease or disorder.

In some embodiments, a compound of the present invention is used to treat neurological diseases. In some embodiments, the compounds have, for example, anti-addictive properties, antidepressant properties, anxiolytic properties, or a combination thereof. In some embodiments, the neurological disease is a neuropsychiatric disease. In some embodiments, the neuropsychiatric disease is a mood or anxiety disorder. In some embodiments, the neurological disease is a migraine, headaches (e.g., cluster headache), post-traumatic stress disorder (PTSD), anxiety, depression, neurodegenerative disorder, Alzheimer's disease, Parkinson's disease, psychological disorder, treatment resistant depression, suicidal ideation, major depressive disorder, bipolar disorder, schizophrenia, stroke, traumatic brain injury, and addiction (e.g., substance use disorder). In some embodiments, the disease is headache disorders. In some embodiments, the neurological disease is a migraine or cluster headache. In some embodiments, the disease is migraines. In some embodiments, the disease is cluster headaches. In some embodiments, the disease is addiction. In some embodiments, the disease is substance use disorder. In some embodiments, the disease is alcohol use disorder. In some embodiments, the disease is alcohol use disorder.

In some embodiments, the neurological disease is a neurodegenerative disorder, Alzheimer's disease, or Parkinson's disease. In some embodiments, the neurological disease is a psychological disorder, treatment resistant depression, suicidal ideation, major depressive disorder, bipolar disorder, schizophrenia, post-traumatic stress disorder (PTSD), addiction (e.g., substance use disorder), depression, or anxiety. In some embodiments, the neuropsychiatric disease is a psychological disorder, treatment resistant depression, suicidal ideation, major depressive disorder, bipolar disorder, schizophrenia, post-traumatic stress disorder (PTSD), addiction (e.g., substance use disorder), depression, or anxiety. In some embodiments, the neuropsychiatric disease or neurological disease is post-traumatic stress disorder (PTSD), addiction (e.g., substance use disorder), schizophrenia, depression, or anxiety. In some embodiments, the neuropsychiatric disease or neurological disease is addiction (e.g., substance use disorder). In some embodiments, the neuropsychiatric disease or neurological disease is depression. In some embodiments, the neuropsychiatric disease or neurological disease is anxiety. In some embodiments, the neuropsychiatric disease or neurological disease is post-traumatic stress disorder (PTSD). In some embodiments, the neurological disease is stroke or traumatic brain injury. In some embodiments, the neuropsychiatric disease or neurological disease is schizophrenia.

In some embodiments, the disease is a neuropsychiatric disease. In some embodiments, the diseases is a neurodegenerative disease.

In some embodiments, a compound of the present invention is used to treat brain disorders. In some embodiments, the compounds have, for example, anti-addictive properties, antidepressant properties, anxiolytic properties, or a combination thereof. In some embodiments, the brain disorder is a neuropsychiatric disease. In some embodiments, the neuropsychiatric disease is a mood or anxiety disorder. In some embodiments, brain disorders include, for example, migraine, cluster headache, post-traumatic stress disorder (PTSD), anxiety, depression, schizophrenia, and addiction (e.g., substance abuse disorder). In some embodiments, brain disorders include, for example, migraines, addiction (e.g., substance use disorder), depression, and anxiety.

In some embodiments, provided herein is a method for increasing neural plasticity, the method comprising contacting a neuronal cell with a compound of the present invention, or a pharmaceutically acceptable salt thereof, in an amount sufficient to increase neural plasticity of the neuronal cell, wherein the compound produces a maximum number of dendritic crossings with an increase of greater than 1.0 fold by a Sholl Analysis.

Neural plasticity refers to the ability of the brain to change structure and/or function throughout a subject's life. New neurons can be produced and integrated into the central nervous system throughout the subject's life. Increasing neural plasticity includes, but is not limited to, promoting neuronal growth, promoting neuritogenesis, promoting synaptogenesis, promoting dendritogenesis, increasing dendritic arbor complexity, increasing dendritic spine density, and increasing excitatory synapsis in the brain. In some embodiments, increasing neural plasticity comprises promoting neuronal growth, promoting neuritogenesis, promoting synaptogenesis, promoting dendritogenesis, increasing dendritic arbor complexity, and increasing dendritic spine density.

In some embodiments, increasing neural plasticity can treat neurodegenerative disorder, Alzheimer's, Parkinson's disease, psychological disorder, depression, addiction, anxiety, post-traumatic stress disorder, treatment resistant depression, suicidal ideation, major depressive disorder, bipolar disorder, schizophrenia, stroke, traumatic brain injury, or substance use disorder. In some embodiments, the neuropsychiatric disease is bipolar disorder. In some embodiments, the disease is depression. In some embodiments, the disease is a neurodegenerative disease. In some embodiments, the disease is Alzheimer's disease or Parkinson's disease. In some embodiments, the disease is Alzheimer's disease. In some embodiments, the disease is Parkinson's disease.

In some embodiments, a compound of the present invention is used to increase neural plasticity. In some embodiments, the compounds used to increase neural plasticity have, for example, anti-addictive properties, antidepressant properties, anxiolytic properties, or a combination thereof. In some embodiments, decreased neural plasticity is associated with a neuropsychiatric disease. In some embodiments, the neuropsychiatric disease is a mood or anxiety disorder. In some embodiments, the neuropsychiatric disease includes, for example, migraine, cluster headache, post-traumatic stress disorder (PTSD), schizophrenia, anxiety, depression, and addiction (e.g., substance abuse disorder). In some embodiments, brain disorders include, for example, migraines, addiction (e.g., substance use disorder), depression, and anxiety. In some embodiments, the disease is a neuropsychiatric disease.

In some embodiments, the experiment or assay to determine increased neural plasticity of any compound of the present invention is a phenotypic assay, a dendritogenesis assay, a spinogenesis assay, a synaptogenesis assay, a Sholl analysis, a concentration-response experiment, a $5\text{-HT}_{2A}$ agonist assay, a $5\text{-HT}_{2A}$ antagonist assay, a $5\text{-HT}_{2A}$ binding assay, or a $5\text{-HT}_{2A}$ blocking experiment (e.g., ketanserin blocking experiments). In some embodiments, the experiment or assay to determine the hallucinogenic potential of any compounds of the present invention is a mouse head-twitch response (HTR) assay.

Compounds of the present invention may have activity as $5\text{-HT}_{2A}$ modulators. In some embodiments, the compounds of the present invention have activity as $5\text{-HT}_{2A}$ modulators. In some embodiments, the compounds of the present invention elicit a biological response by activating the $5\text{-HT}_{2A}$ receptor (e.g., allosteric modulation or modulation of a biological target that activates the $5\text{-HT}_{2A}$ receptor). $5\text{-HT}_{2A}$ agonism has been correlated with the promotion of neural plasticity. In some embodiments, the $5\text{HT}_{2A}$ sensor assay is in an agonist mode or an antagonist mode. In some embodiments, the $5\text{HT}_{2A}$ sensor assay is in an agonist mode.

In some embodiments, the compounds described herein are selective $5\text{-HT}_{2A}$ modulators. In some embodiments, the compounds described herein are $5\text{-HT}_{2A}$ modulators and promote neural plasticity (e.g., cortical structural plasticity). In some embodiments, the compounds described herein are selective $5\text{-HT}_{2A}$ modulators and promote neural plasticity (e.g., cortical structural plasticity). In some embodiments, promotion of neural plasticity includes, for example, increased dendritic spine growth, increased synthesis of synaptic proteins, strengthened synaptic responses, increased dendritic arbor complexity, increased dendritic branch content, increased spinogenesis, increased neuritogenesis, or any combination thereof. In some embodiments, increased neural plasticity includes, for example, increased cortical structural plasticity in the anterior parts of the brain.

In some embodiments, non-hallucinogenic $5\text{-HT}_{2A}$ modulators (e.g., $5\text{-HT}_{2A}$ agonists) are used for treating a disease. In some embodiments, non-hallucinogenic $5\text{-HT}_{2A}$ modulators (e.g., $5\text{-HT}_{2A}$ agonists) are used for increasing neural plasticity. In some embodiments, non-hallucinogenic $5\text{-HT}_{2A}$ modulators (e.g., $5\text{-HT}_{2A}$ agonists) are used for increasing neural plasticity and dendritic spine density.

In some embodiments, the experiment or assay to determine increased neural plasticity of any compound of the present invention is a phenotypic assay, a dendritogenesis assay, a spinogenesis assay, a synaptogenesis assay, a Sholl analysis, a concentration-response experiment, a $5\text{-HT}_{2C}$ agonist assay, a $5\text{-HT}_{2C}$ antagonist assay, a $5\text{-HT}_{2C}$ binding assay, or a $5\text{-HT}_{2C}$ blocking experiment (e.g., ketanserin blocking experiments). In some embodiments, the experiment or assay to determine the hallucinogenic potential of any compounds of the present invention is a mouse head-twitch response (HTR) assay.

Compounds of the present invention may have activity as $5\text{-HT}_{2C}$ modulators. In some embodiments, the compounds of the present invention have activity as $5\text{-HT}_{2C}$ modulators. In some embodiments, the compounds of the present invention elicit a biological response by activating the $5\text{-HT}_{2C}$ receptor (e.g., allosteric modulation or modulation of a biological target that activates the $5\text{-HT}_{2C}$ receptor). $5\text{-HT}_{2C}$ agonism has been correlated with the promotion of neural plasticity. In some embodiments, the $5\text{HT}_{2C}$ sensor assay is in an agonist mode or an antagonist mode. In some embodiments, the $5\text{HT}_{2C}$ sensor assay is in an agonist mode.

In some embodiments, the compounds described herein are selective $5\text{-HT}_{2C}$ modulators. In some embodiments, the compounds described herein are $5\text{-HT}_{2C}$ modulators and promote neural plasticity (e.g., cortical structural plasticity). In some embodiments, the compounds described herein are selective 5-HT$_{2C}$ modulators and promote neural plasticity (e.g., cortical structural plasticity). In some embodiments, promotion of neural plasticity includes, for example, increased dendritic spine growth, increased synthesis of synaptic proteins, strengthened synaptic responses, increased dendritic arbor complexity, increased dendritic branch content, increased spinogenesis, increased neurito-genesis, or any combination thereof. In some embodiments, increased neural plasticity includes, for example, increased cortical structural plasticity in the anterior parts of the brain.

In some embodiments, non-hallucinogenic 5-HT$_{2C}$ modu-lators (e.g., 5-HT$_{2C}$ agonists) are used for treating a disease. In some embodiments, non-hallucinogenic 5-HT$_{2C}$ modula-tors (e.g., 5-HT$_{2C}$ agonists) are used for increasing neural plasticity. In some embodiments, non-hallucinogenic 5-HT$_{2C}$ modulators (e.g., 5-HT$_{2C}$ agonists) are used for increasing neural plasticity and dendritic spine density.

In some embodiments, provided herein is a method for increasing neural plasticity and increasing dendritic spine density, the method comprising contacting a neuronal cell with a compound of the present invention, or a pharmaceu-tically acceptable salt thereof, in an amount sufficient to increase neural plasticity and increase dendritic spine den-sity of the neuronal cell.

Dendritic spines are dynamic and can have significant changes in density, shape, and volume over time. The growth or loss of dendritic spines, which contribute to the dendritic spine density, can be important for reinforcing neural pathways for learning, memory, and general cognitive function. Increasing dendritic spine density can be useful for treatment of neurological diseases, such as, but not limited to, neurodegenerative diseases and neuropsychiatric dis-eases.

Increasing dendritic spine density can be measured by staining and immunocytochemical methods known by one of skill in the art. Staining methods include, but are not limited to electron microscopy, Golgi staining, crystal violet staining, DAPI staining, and eosin staining. For example, Golgi staining can be used to measure dendritic spine density.

In some embodiments, a compound provided herein, or pharmaceutically acceptable salts thereof, is useful for pro-moting neuronal growth and/or improving neuronal struc-ture.

In some embodiments, a compound provided herein, or pharmaceutically acceptable salts thereof, is a non-halluci-nogenic psychoplastogens useful for treating one or more diseases or disorders associated with loss of synaptic con-nectivity and/or plasticity.

In some embodiments, an individual administered a com-pound provided herein does not have a hallucinogenic event (e.g., at any point after the compound has been administered to the individual).

In some embodiments, provided herein is a method for treating a disease or disorder in an individual in need thereof, wherein the disease or disorder is a neurological diseases and disorder.

Provided in some embodiments herein is a compound (e.g., or pharmaceutically acceptable salt or solvate thereof) useful for the modulation of a 5-hydroxytryptamine (5-HT) receptor. In some embodiments, the 5-HT receptor modu-lated by a compound provided herein is 5-hydroxytryptam-ine receptor 2A (5-HT$_{2A}$). In some embodiments, the 5-HT receptor modulated by a compound provided herein is 5-hydroxytryptamine receptor 2C (5-HT$_{2C}$).

In some embodiments, provided herein is a modulator of 5-hydroxytryptamine receptor 2A (5-HT$_{2A}$) that is useful for treating one or more diseases or disorders associated with 5-HT$_{2A}$ activity. In some embodiments, provided herein is a modulator of 5-hydroxytryptamine receptor 2C (5-HT$_{2C}$) that is useful for treating one or more diseases or disorders associated with 5-HT$_{2C}$ activity.

In some embodiments, a compound provided herein, or a pharmaceutically acceptable salt thereof, is used in the preparation of medicaments for the treatment of diseases or conditions in a mammal that would benefit from inhibition or reduction of 5-HT$_{2A}$ activity and/or 5-HT$_{2C}$ activity.

In some embodiments, a compound provided herein, or a pharmaceutically acceptable salt thereof, is used in the preparation of medicaments for the treatment of diseases or conditions in a mammal that would benefit from promoting neuronal growth and/or improving neuronal structure.

Methods for treating any of the diseases or conditions described herein in a mammal in need of such treatment, involves administration of pharmaceutical compositions that include at least one compound described herein or a phar-maceutically acceptable salt, active metabolite, prodrug, or pharmaceutically acceptable solvate thereof, in therapeuti-cally effective amounts to said mammal.

In certain embodiments, the compositions containing the compound(s) described herein are administered for prophy-lactic and/or therapeutic treatments. In certain therapeutic applications, the compositions are administered to a mam-mal already suffering from a disease or condition, in an amount sufficient to cure or at least partially arrest at least one of the symptoms of the disease or condition. Amounts effective for this use depend on the severity and course of the disease or condition, previous therapy, the mammal's health status, weight, and response to the drugs, and the judgment of a healthcare practitioner. Therapeutically effective amounts are optionally determined by methods including, but not limited to, a dose escalation and/or dose ranging clinical trial.

In prophylactic applications, compositions containing the compounds described herein are administered to a mammal susceptible to or otherwise at risk of a particular disease, disorder or condition. Such an amount is defined to be a "prophylactically effective amount or dose." In this use, the precise amounts also depend on the mammal's state of health, weight, and the like. When used in mammals, effec-tive amounts for this use will depend on the severity and course of the disease, disorder or condition, previous therapy, the mammal's health status and response to the drugs, and the judgment of a healthcare professional. In some embodiments, prophylactic treatments include admin-istering to a mammal, who previously experienced at least one symptom of the disease being treated and is currently in remission, a pharmaceutical composition comprising a com-pound described herein, or a pharmaceutically acceptable salt thereof, in order to prevent a return of the symptoms of the disease or condition.

In some embodiments wherein the mammal's condition does not improve, upon the discretion of a healthcare professional the administration of the compounds are admin-istered chronically, that is, for an extended period of time, including throughout the duration of the mammal's life in order to ameliorate or otherwise control or limit the symp-toms of the mammal's disease or condition.

In some embodiments wherein a mammal's status does improve, the dose of drug being administered is temporarily reduced or temporarily suspended for a certain length of time (i.e., a "drug holiday"). In some embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In some embodiments, however, the mammal requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg-5000 mg per day. In some embodiments, doses employed for adult human treatment are from about 1 mg to about 1000 mg per day. In some embodiments, the desired dose is conveniently presented in a single dose or in divided doses administered simultaneously or at appropriate intervals, for example as two, three, four or more sub-doses per day.

In some embodiments, the daily dosages appropriate for the compound described herein, or a pharmaceutically acceptable salt thereof, are from about 0.01 to about 50 mg/kg per body weight. In some embodiments, the daily dosage or the amount of active in the dosage form are lower or higher than the ranges indicated herein, based on a number of variables in regard to an individual treatment regime. In some embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{50}$ and the $ED_{50}$. The dose ratio between the toxic and therapeutic effects is the therapeutic index and it is expressed as the ratio between $LD_{50}$ and $ED_{50}$. In some embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In some embodiments, the daily dosage range and/or the unit dosage amount varies within this range depending upon the dosage form employed and the route of administration utilized.

In any of the aforementioned aspects are further embodiments in which the effective amount of the compound described herein, or a pharmaceutically acceptable salt thereof, is: (a) systemically administered to the mammal; and/or (b) administered orally to the mammal; and/or (c)

intravenously administered to the mammal; and/or (d) administered by injection to the mammal; and/or (e) administered topically to the mammal; and/or (f) administered non-systemically or locally to the mammal.

In any of the aforementioned aspects are further embodiments comprising single administrations of the effective amount of the compound, including further embodiments in which (i) the compound is administered once a day; or (ii) the compound is administered to the mammal multiple times over the span of one day.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

In some embodiments, the therapeutic effectiveness of one of the compounds described herein is enhanced by administration of an adjuvant (i.e., by itself the adjuvant has minimal therapeutic benefit, but in combination with another therapeutic agent, the overall therapeutic benefit to the patient is enhanced). Or, in some embodiments, the benefit experienced by a patient is increased by administering one of the compounds described herein with another agent (which also includes a therapeutic regimen) that also has therapeutic benefit.

In some embodiments, different therapeutically-effective dosages of the compounds disclosed herein will be utilized in formulating pharmaceutical composition and/or in treatment regimens when the compounds disclosed herein are administered in combination with one or more additional agent, such as an additional therapeutically effective drug, an adjuvant or the like. Therapeutically-effective dosages of drugs and other agents for use in combination treatment regimens is optionally determined by means similar to those set forth hereinabove for the actives themselves. Furthermore, the methods of prevention/treatment described herein encompasses the use of metronomic dosing, i.e., providing more frequent, lower doses in order to minimize toxic side effects. In some embodiments, a combination treatment regimen encompasses treatment regimens in which administration of a compound described herein, or a pharmaceutically acceptable salt thereof, is initiated prior to, during, or after treatment with a second agent described herein, and continues until any time during treatment with the second agent or after termination of treatment with the second agent. It also includes treatments in which a compound described herein, or a pharmaceutically acceptable salt thereof, and the second agent being used in combination are administered simultaneously or at different times and/or at decreasing or increasing intervals during the treatment period. Combination treatment further includes periodic treatments that start and stop at various times to assist with the clinical management of the patient.

It is understood that the dosage regimen to treat, prevent, or ameliorate the disease(s) for which relief is sought, is modified in accordance with a variety of factors (e.g. the disease or disorder from which the subject suffers; the age, weight, sex, diet, and medical condition of the subject). Thus, in some instances, the dosage regimen actually employed varies and, in some embodiments, deviates from the dosage regimens set forth herein.

VI. Examples

Detailed Methods

Data Analysis and Statistics. Treatments were randomized, and data were analyzed by experimenters blinded to treatment conditions. Statistical analyses were performed using GraphPad Prism (version 9.1.2) unless noted otherwise. All comparisons were planned prior to performing each experiment. Data are represented as mean±SEM, unless noted otherwise, with asterisks indicating *$p<0.05$, $p<0.01$, *$p<0.001$, and ****$p<0.0001$.

Molecular Docking. Docking of (+)-JRT to the 5-HT2AR was performed using Autodock Vina (version 1.1.2) and a previously published structure of the 5-HT2AR bound to LSD (PDB: 7wc6). The existing ligand (i.e., LSD) in the published structure was first removed from the protein. Then, (+)-JRT was docked at the known active site according to specific parameters. The binding pocket search region was defined as a 40×40×40 grid with a spacing of 0.375 Å at coordinates x=−28, y=−11, z=142 as designated in MGL AutoDockTools (version 1.5.7) with an exhaustiveness setting of 20. The generated conformations were analyzed and exported using MGL AutoDockTools (version 1.5.7). A (+)-JRT PDB structure was generated by conversion of a ChemDraw structure using UCSF Chimera. The 3D images of the binding site were produced using UCSF Chimera (version 1.16) from the Resource for Biocomputing, Visualization, and Informatics at the University of California, San Francisco (supported by NIH P41 RR-01081).

Drugs. Many of the drugs used in these studies were purchased from commercial sources including D-amphetamine sulfate (Sigma Aldrich, 1180004), ketamine hydrochloride (Spectrum, K1068), and ketanserin (APExBIO, B2248). Lysergic acid diethylamide (LSD) hemitartrate was generously provided by the NIH Drug Supply Program. Both (+)-JRT and (−)-JRT were synthesized in-house and judged to be analytically pure based on NMR and LC-MS data. For cell culture experiments, VEH=0.1% (agonist studies) or 0.2% (antagonist studies) molecular biology grade dimethyl sulfoxide (Sigma-Aldrich). For in vivo experiments, compounds were administered i.p. at 5 mL/kg using 0.9% saline as the vehicle, unless noted otherwise. VEH=USP grade saline (0.9%). Free bases were used for all cellular experiments while fumarate salts of (+)-JRT and (−)-JRT were used for in vivo studies. Stock solutions for behavioral assays were prepared fresh before use.

Animals. All experimental procedures involving animals were approved by the Institutional Animal Care and Use Committee (IACUC) at the University of California, Davis, the Salk Institute, Weill Cornell Medicine, or the Contract Research Organization (CRO) where the study was performed. All procedures involving animals adhered to principles described in the National Institutes of Health Guide for the Care and Use of Laboratory Animals. Animals were either obtained from Jackson Laboratory (Sacramento, C.A.) or bred in house unless noted otherwise. Power analyses were conducted to ensure appropriate sample size for all experiments involving animals. Animals were housed 2-5 animals of the same sex per cage and were given ad libitum access to food and water unless noted otherwise. Lights in the vivarium were turned on at 07:00 hours and turned off at 19:00 hours. The University of California, Davis, the Salk Institute, and Weill Cornell Medicine are accredited by the Association for Assessment and Accreditation of Laboratory Animal Care International (AAALAC).

Radioligand Binding Selectivity Panel. Competitive radioligand binding studies for (+)-JRT (10 μM) and (−)-JRT (10 μM) were performed across a panel of receptors at Eurofins Discovery. LSD $K_i$ values were obtained from previous reports, and whenever possible, were matched for radioligand and source of receptor.

Radioligand Binding Assays (5-HT2AR and 5-HT2CR). The 5-HT2AR and 5-HT2CR competitive radioligand binding assays were performed at Epics Therapeutics S.A. (Belgium, FAST-0505B) using conventional methods. Briefly, competition binding was performed in duplicate in the wells of a 96-well plate (Master Block, Greiner, 786201) containing binding buffer, membrane extracts, radiotracer [$^3$H]-DOI and test compound. Nonspecific binding was determined by co-incubation with 200-fold excess of cold competitor DOI. The samples were incubated in a final volume of 0.1 mL at a temperature and for a duration optimized for either the 5-HT2AR or 5-HT2CR and then filtered over filter plates. Filters were washed six times with 0.5 ml of ice-cold washing buffer (optimized for 5-HT2AR) and 50 μl of Microscint 20 (Packard) were added in each well. The plates were incubated for 15 min on an orbital shaker and then counted with a TopCount™ for 1 min/well.

Radioligand Binding Assays (5-HT2BR). The 5-HT2BR competitive radioligand binding assays were performed at Eurofins Cerep SA (Celle l'Evescault, France) using conventional methods (Catalog #1333).

IP1 Assay (5-HT2AR and 5-HT2CR). The 5-HT2AR and 5-HT2CR IPOne HTRF assays were performed at Epics Therapeutics S.A. (Belgium, FAST-0505I) using conventional methods. Briefly, CHO-K1 cells expressing human recombinant 5-HT2AR grown to mid-log phase in culture media without antibiotics were detached with PBS-EDTA, centrifuged, and resuspended in medium without antibiotics buffer. Then, 20,000 cells were distributed in a 96-well plate and incubated overnight at 37° C. with 5% $CO_2$. For agonist testing, the medium was removed and 20 μl of assay buffer plus 20 μl of test compound or reference agonist (α-Me-5-HT) were added to each well. The plate was incubated for 60 min at 37° C. with 5% $CO_2$. After addition of the lysis buffer containing IP1-d2 and anti-IP1 cryptate detection reagents, plates were incubated for 1 h at room temperature and fluorescence ratios were measured according to the manufacturer's specifications using the HTRF kit.

IP1 Assay (5-HT2BR). The 5-HT2BR IP1 assays were performed at Eurofins Cerep SA (Celle l'Evescault, France) using conventional methods (Catalog #3344).

β-Arrestin Activation (PathHunter®). The 5-HT2AR PathHunter® β-Arrestin agonist assay was performed at Eurofins DiscoverX (Frement, CA, Catalog #86-0001P-2090AG). The PathHunter® β-Arrestin assay monitors the activation of a GPCR in a homogenous, non-imaging assay format using a technology developed by DiscoverX called Enzyme Fragment Complementation (EFC) with β-galactosidase (β-Gal) as the functional reporter. The enzyme is split into two inactive complementary portions: a small peptide, called ProLink™ (PK) and a larger protein, called Enzyme Acceptor (EA). PK and EA are then expressed as fusion proteins in U2OS cells, with PK fused to the GPCR of interest, and EA fused to β-Arrestin. When the target GPCR is activated and β-Arrestin is recruited to the receptor, PK and EA complementation occurs, restoring β-Gal activity which is measured using chemiluminescent PathHunter® Detection Reagents.

PsychLight Assays. Psychlight assays were performed using a previously published method. Briefly, glass bottom 96-well plates were coated with 50 µg/mL of poly-D-lysine overnight at room temperature and then washed with Dulbecco's PBS. PSYLI2 cells were suspended in DMEM containing 10% FBS with 5% penicillin-streptomycin, plated at a density of 40,000 cells/well, and incubated (37° C., 5% $CO_2$) for 24 h prior to each experiment. Immediately before an experiment, stock solutions of drugs in DMSO were diluted 1:100 in imaging media distributed across an empty 96-well plate (treatment plate) following a randomized plate map. The imaging media consisted of 1×HBSS containing 0.5 M $MgCl_2$ and 0.5 M $CaCl_2$. Cells grown in a separate 96-well plate were gently washed 3× with imaging media, and wells were filled with imaging media. All imaging and incubation (both agonist and antagonist mode) were performed at ambient atmosphere and temperature. Data were from 2 plates with 2-3 wells being analyzed per plate. The VEH treated condition was normalized to 0% ΔF/F.

For agonist mode experiments, 180 µL of imaging media were added to each well containing PSYLI2 cells. Wells were then imaged on a Thermofisher CellInsight CX7 HCS Platform at 40× (N.A.=0.6). Regions of interest (ROI) followed the default ROI pattern for each well with no bias to location and no overlap of the ROIs (exposure=400 ms, LED power=100%). Next, 20 µL from the treatment plate was transferred to the plate containing PSYLI2 cells resulting in a final dilution of 1:1000. As positive, negative, and vehicle controls, 5-HT (10 µM), ketanserin (10 µM), and DMSO (0.1%) were used, respectively. After 5 min of incubation, the same ROIs were re-imaged using the same settings.

Once imaging was complete, the images were exported, and analyzed using a custom Python script. Briefly, segmentation was performed on individual images and a mask highlighting the membrane of the HEK293T cells was generated. The mask was generated by calculating the average fluorescence intensity for the entire image and using that value as a threshold. Pixels with intensities above that threshold were incorporated into the mask. Pixel intensities were obtained from the mask-highlighted area, then used to calculate % ΔF/F and exported to Excel. The % ΔF/F values for each well were calculated using the following equation:

$$\%\Delta F/F = \frac{(\text{average after drug} - \text{average before drug})}{\text{average before drug (baseline)}} \times 100$$

Individual % ΔF/F values were then averaged on a per well basis. The VEH treated condition was arbitrarily assigned a concentration of 1 fM and used as the first concentration point for all treatment response curves.

For antagonist mode experiments, 160 µL of imaging media was added to each well of the assay plate. Wells were then imaged on a CellInsight CX7 HCS Platform at 40× (N.A.=0.6). ROIs followed the default ROI pattern for each well with no bias to location and no overlap of the ROIs (exposure=400 ms, LED power=100%). A 100 µM stock solution of 5-HT in DMSO was diluted 1:100 in imaging buffer. Next, 20 µL of this solution was added to the plate containing PSYLI2 cells for a final concentration of 111 nM 5-HT (0.1% DMSO). The same ROIs were imaged after 5 min of incubation. Next, 20 µL from the treatment plate was transferred to the plate containing PSYLI2 cells for a final dilution of 1:1000 dilution (0.2% DMSO). After 5 min of incubation, the same sites were re-imaged using the same settings.

Once imaging was complete, the images were exported, and analyzed using a custom Python script. Briefly, segmentation was performed on individual images and a mask highlighting the membrane of the JAK293T cells was generated. The mask was generated by calculating the average fluorescence intensity for the entire image and using that value as a threshold. Pixels with intensities above that threshold were incorporated into the mask. Pixel intensities were obtained from the mask-highlighted area, then used to calculate % ΔF/F and exported to Excel. Then the % ΔF/F values for each well were calculated using the following equation:

$$\%\Delta F/F = \frac{(\text{average after drug} - \text{average after } 5-HT)}{\text{average after } 5-HT \text{ (baseline)}} \times 100$$

Individual % ΔF/F values were then averaged on a per well basis.

In Vivo Spinogenesis. Female C57BL/6J mice (Jackson Laboratory, Sacramento, C.A.) were treated with VEH (saline) or (+)-JRT (n=3/group). After 24 h, the animals were sacrificed via transcardial perfusion with oxygenated Ringer's solution followed by a fixative (2% paraformaldehyde, 2.5% glutaraldehyde, 3 mM calcium chloride in 0.1 M cacodylate buffer). Brains were carefully removed from the skull and post-fixed overnight in the same fixative. Brains were then rinsed with PBS and 100 µm coronal sections spanning the prefrontal cortex were collected using a vibrating microtome (Leica). Regions of the infralimbic cortex were microdissected according to the Allen brain atlas and processed further for electron microscopy. Briefly, samples were stained with buffered 1.5% reduced osmium tetroxide for 45 minutes, rinsed thoroughly, further stained with 1% aqueous uranyl acetate overnight at 4° C., dehydrated and embedded in Eponate 12 epoxy resin. A blockface that spanned from the medial cortical surface to the corpus collosum was trimmed and 150-250 serial ultrathin sections (55 nm) were collected onto silicon chips using diamond knives (Diatome) on an ultramicrotome (Leica). Serial sections on silicon chips were loaded into the scanning electron microscope (SEM; Zeiss Sigma VP) for imaging. The apical tuft region was identified, and a series of images were collected from a region of interest identified on consecutive sections. Following image alignment (accomplished using SWIFT-IR through 3dem.org), the datasets for each animal constituted volumes of at least 20×20×10 µm in dimension with voxel sizes of 8×8×55 nm. Cross sections of eight random dendrites were sampled from the central section of each volume. Skeletons of the dendritic centerline and dendritic spines were traced by two human experts in VAST Lite software. Dendritic spine densities (spines/micron) were calculated for each volume.

Head-Twitch Response Assay. The HTR assay was performed using equal numbers of male and female C57BL/6J mice. The mice were obtained from The Jackson Laboratory (Sacramento, CA) and were approximately 8-12 weeks old at the time of the experiments. After compound administration, animals were placed into an empty arena (40 cm×40 cm) and filmed for 20 min. The arena was cleaned with 70% ethanol between trials. Animals were given a one-week washout period before being tested again. Animals were tested a maximum of 4 times. All drug treatments were randomized and no animal received the same drug and dose twice. For the blocking experiments, animals were administered (+)-JRT (1 mg/kg) or vehicle (saline) via IP injection and placed in an empty cage for 15 min. Animals were then administered LSD (0.2 mg/kg, IP), placed in the test arena, and filmed for 20 min. Videos were scored later by two blinded observers, and the results were averaged (Pearson correlation coefficient>0.9).

Amphetamine Induced Locomotion. The amphetamine-induced hyperlocomotion assay was performed using male and female C57BL/6J mice that were approximately 8 weeks old at the time of the experiments. Animals were first placed in the test arena (40 cm×40 cm) for 15 min to obtain a basal reading of locomotion and habituate them to the testing arena. Next, animals were administered (+)-JRT (1 mg/kg) or VEH (2.5 mL/kg, i.p) and placed back in the test arena. After 15 min, the animals were administered D-amphetamine (3 mg/kg) or VEH (2.5 mL/kg) and placed back in the test arena for 60 minutes. Locomotion during the entire experiment was quantified using ANYmaze Video Tracking System, version 7.07 (Stoelting Co.).

Rat Forced Swim Test (FST). This study was performed by Psychogenics (Paramus, NJ). Male Sprague Dawley rats were purchased from Envigo (Indianapolis, IN), and upon receipt, they were assigned unique identification numbers (tail marked) and group housed in ventilated cages with 3 rats per cage. All animals remained housed in groups of three for the remainder of the study. All rats were acclimated to the colony room for up to one week prior to dosing. During the period of acclimation, rats were examined and handled daily, and weighed to assure adequate health and suitability. The room temperature was maintained between 20° C. and 23° C. with a relative humidity of 30%-70%. Lab Rodent Diet 5001 (W.F. Fisher, Cat #11015) and water were provided ad libitum. Animals were randomly assigned across treatment groups. All testing was performed during the light phase of the light/dark cycle. Behavioral testing was conducted according to established protocols approved by the IACUC committee and PGI Standard Operation Procedures (SOP). Each forced swim chamber was constructed of clear acrylic (height=40 cm; diameter=20.3 cm). Only one rat was placed in the swim chamber at a time for each swim test. The water was changed and the chamber cleaned between each animal. The water depth was 16 cm in the first swim session (pre-test) and 30 cm in the second swim session (test). The water was maintained at 23° C.±1° C. for all swim sessions. At the end of each swim test rats were dried with paper towels and returned to the home cage. All animals were carefully monitored to ensure their safety in the swim test and any animal unable to maintain a posture with its nose above water was immediately removed from the water and not used further in the study. Animals were first subjected to a pre-test for 15 min. Immediately after the pre-test, they were administered compounds or VEH via i.p. injection (1 ml/kg). Racemic ketamine hydrochloride (10 mg/kg) was used as a positive control. A salt correction factor of 1.36 was used when preparing formulations of (+)-JRT to ensure that the dose corresponded to that of the free base. A second FST was conducted 24 h after compound administration. This test lasted for 5 min and was video recorded. A blinded experimenter manually scored the videos for swimming, climbing, and immobility behavior. Scoring of the forced swim test was performed by trained technicians using a time sampling technique in which the animal in the video recorded test was viewed every 5 seconds and the behavior observed was noted (e.g., immobile, swimming, or climbing). A total of 60 behaviors were noted per subject per session.

4-Odor Discrimination and Reversal. A 4-odor discrimination and reversal behavioral assay was performed as described previously with slight modifications. Food restriction was begun five days before the discrimination and reversal tests to reduce animals' body weight to ~80% of their starting weight. A total of 31 C57BL/6J mice 2-3 months of age were used in this assay. Eleven mice (5 males, 6 females) served as VEH/unstressed controls, 10 animals (4 males, 6 females) as a VEH/stress group, and 10 animals (4 males, 6 females) as a treatment/stress group. Both the VEH/stress and VEH/treatment groups were subjected to a 7-day unpredictable mild stress protocol using previously validated stressors. Two stressors were delivered during the day, with additional overnight stressors on 4 of the days. In brief, the following stressors were used: Day 1: AM=30 min of predator order, PM=instability (wet bedding+tilt for 30 min), Overnight=tilted cage; Day 2: AM=overcrowding/social interaction (30 min), PM=restraint stress (30 min), Overnight=none; Day 3: AM=restraint stress (30 min), PM=predator odor (30 min), Overnight=none; Day 4: AM=exposure to a new room (30 min)+tail suspension (6 min), PM=restraint stress (30 min), Overnight=tilted cage; Day 5: AM=instability (wet bedding+tilt for 30 min), PM=overcrowding/social interaction (30 min), Overnight=none; Day 6: AM=white noise/room change, PM=instability (wet bedding+tilt for 30 min), Overnight=tilted cage; Day 7: AM=restraint stress (30 min), PM=overcrowding/social interaction (30 min), Overnight=light exposure.

Following unpredictable mild stress, the animals underwent habituation/shaping/training on Days 7 and 8 before discrimination and reversal testing on day 9. The behavioral apparatus was a 12"×12"×9" (length×width×height) opaque white acrylic box with 3" long transparent acrylic internal walls in the center of each exterior wall to create 4 quadrants and a removable transparent cylinder of diameter 6" that fit in the center of the box. On the first training day (Day 7), mice were habituated to the apparatus and four 4-oz white ceramic pots (Yachi, www.amazon.com), which were each placed in a corner of one of the box's quadrants with a piece (~0.015 g) of Honey Nut Cheerio (General Mills, Golden Valley, MN) as food reward inside. For this first day of habituation, mice were placed in the center cylinder, and the cylinder was then removed to begin each round of habituation; mice were allowed to explore freely until all 4 pots' food rewards were consumed or 10 minutes had passed. Mice were then returned to the cylinder and pots were rebaited as necessary, for a total of 6 rounds of habituation during day 1.

On the second training day (Day 8), VEH (saline) or (+)-JRT (1 mg/kg) were administered via IP injection. After a short recovery period, shaping was performed with one pot. The food reward was delivered with increasing amounts of pine shavings (Living World, www.amazon.com) covering it which required the mouse to dig to obtain the reward. The pot was moved between the four apparatus quadrants so that each position was rewarded equally; after finding and consuming the food reward, the mouse was returned to the center cylinder between trials. Trials began with the food reward placed in an empty dish (4 trials), then with a dusting of pine bedding added (4 trials), followed by trials with the dish a quarter full (4 trials), half full (4 trials) and full (12 trials) with pine shavings.

On testing day (Day 9), four pots were filled with shavings and had a piece of filter paper scented with a drop of essential oil (LorAnn Oils, Lansing, MI) attached to the inner rim. Rosemary, thyme, clove, and nutmeg were used in the initial discrimination phase, with rosemary serving as the rewarded odor which indicated which pot contained the food reward. The mouse was placed in the center cylinder and then allowed to explore the arena after the cylinder was removed at the start of each trial. Trials ended after either the food reward was located and eaten, digging was initiated in an unrewarded pot, or three minutes passed without digging occurring. The mouse was then returned to the center cylinder, the rewarded pot was rebaited if necessary, and pots were repositioned so that no one pot remained in the same quadrant during consecutive trials. A trial in which no digging was observed was recorded as an omission; after two consecutive omissions, a pot was placed in the center cylinder with pine shavings and a food reward placed in a well within the shavings, in order to potentiate digging. Mice passed this discrimination phase when they successfully located and ate the food reward in 8 of 10 consecutive trials. Immediately following discrimination, pine shavings were replaced in all pots and the thyme odorant replaced with a novel cinnamon odorant. The rewarded odorant was changed from rosemary to clove. Mice were again considered to have passed this reversal phase after successfully locating and eating the food reward in 8 of 10 consecutive trials.

Materials and Methods

All reagents were obtained from commercial sources and reactions were performed using oven-dried glassware (120° C.) under an inert $N_2$ atmosphere unless otherwise noted. Air- and moisture-sensitive liquids and solutions were transferred via syringe or stainless-steel cannula. Organic solutions were concentrated under reduced pressure (~5 Torr) by rotary evaporation. Solvents were purified by passage under 12 psi Ar through activated alumina columns. Chromatography was performed using Fisher Chemical™ Silica Gel Sorbent (230-400 Mesh, Grade 60). Compounds purified by chromatography were typically applied to the adsorbent bed using the indicated solvent conditions with a minimum amount of added dichloromethane as needed for solubility. Thin layer chromatography (TLC) was performed on Merck silica gel 60 F254 plates (250 μm). Visualization of the developed chromatogram was accomplished by fluorescence quenching or by staining with aqueous potassium permanganate or Ehrlich's reagent.

Nuclear magnetic resonance (NMR) spectra were acquired on a Bruker 400 operating at 400 and 100 MHz for $^1$H and $^{13}$C, respectively, and are referenced internally according to residual solvent signals. Data for $^1$H NMR are recorded as follows: chemical shift (δ, ppm), multiplicity (s, singlet; d, doublet; t, triplet; q, quartet; quint, quintet; m, multiplet), coupling constant (Hz), and integration. Data for $^{13}$C NMR are reported in terms of chemical shift (δ, ppm). Infrared spectra were recorded using a Thermo Nicolet iS10 Fourier transform infrared (FT-IR) spectrometer with a Smart iTX Accessory [diamond attenuated total reflection (ATR)] and are reported in the frequency of absorption (v, cm$^{-1}$). Liquid chromatography-mass spectrometry (LC-MS) was performed using a Waters LC-MS with an ACQUITY Arc QDa detector.

Example 1: Preparation of N,N-diethyl-8-methyl-7a,8,9,10-tetrahydro-7H-indolo[7,1-fg][1,7]naphthyridine-10-carboxamide (14, Major Diastereomer, (±)-JRT)

3-bromo-5-(diethylcarbamoyl)pyridine 1-oxide (3)

To a 0° C. cooled mixture of 5-bromonicotinic acid (10.000 g, 49.503 mmol, 1.0 equiv) in DCM (250 mL) was added oxalyl chloride (6.37 mL, 74.2 mmol, 1.5 equiv) slowly. To the suspension was added DMF (0.5 mL) dropwise, and the mixture was warmed to ambient temperature and stirred for 1 h. The mixture was cooled to 0° C. and a solution of diethylamine (25.61 mL, 247.5 mmol, 5.0 equiv) in DCM (250 mL) was added slowly via cannula. The mixture was warmed to ambient temperature and stirred for 30 min. $H_2O$ (500 mL) was added, followed by 2M HCl (40 mL) until the pH=1 to 2. The layers were separated, and the aqueous layer was further extracted with DCM (3×200 mL). The organic extracts were combined and sequentially washed with saturated aqueous $NaHCO_3$ (1×250 mL) and brine (1×250 mL). The organic extract was dried over $Na_2SO_4$, and concentrated under reduced pressure.

To a 0° C. cooled solution of the resulting brown oil in DCM (200 mL) was added MCPBA (70-75% balance) (22.781 g, 99.006 mmol, 2.0 equiv). The mixture was warmed to ambient temperature and stirred for 18 h. To the solution was added saturated aqueous $NaHCO_3$ (500 mL) and then 1M NaOH (500 mL). The layers were separated, and the aqueous layer was further extracted with 10% IPA in DCM (3×200 mL). The organic layers were combined, dried over Na$_2$SO$_4$, filtered, and concentrated under reduced pressure. The residue was purified via chromatography on silica gel (EtOAc then 12% MeOH in EtOAc) and concentrated under reduced pressure. The resulting pale yellow oil was dissolved in DCM (50 mL), and to the solution was added hexanes (500 mL) slowly with vigorous stirring. The suspension was cooled to 0° C., filtered, and washed with 100 mL cold hexanes to afford 3 (11.041 g, 82%) as a white solid.

$^1$H NMR (400 MHZ, CDCl$_3$) δ=8.32 (t, J=1.5 Hz, 1H), 8.09 (t, J=1.3 Hz, 1H), 7.35 (t, J=1.3 Hz, 1H), 3.54-3.46 (m, 2H), 3.29-3.21 (m, 2H), 1.24-1.12 (m, 6H) ppm. $^{13}$C NMR (100 MHZ, CDCl$_3$) δ=164.3, 141.0, 136.3, 135.9, 126.4, 120.7, 43.5, 39.9, 14.4, 12.8 ppm. LRMS (ES$^+$) m/z [M+H]$^+$ calcd for C$_{10}$H$_{14}$BrN$_2$O$_2$$^+$ 273.02; Found 273.12. IR (diamond, ATR) ν 3445, 3068, 2973, 2934, 1633 cm$^{-1}$.

5-bromo-6-chloro-N,N-diethylnicotinamide (4)

3

4

To a −61° C. cooled (CHCl$_3$/dry ice) solution of 3 (9.900 g, 36.395 mmol, 1.0 equiv) and Et$_3$N (10.15 mL, 72.79 mmol, 2.0 equiv) in DCM (180 mL) was added oxalyl chloride (6.24 mL, 72.8 mmol, 2.0 equiv) slowly dropwise. The mixture was stirred for 30 minutes, then MeOH (5 mL) was added slowly before warming to ambient temperature, then saturated aqueous NaHCO$_3$ (25 mL) was added. The solution was poured into 1M NaOH (600 mL) and the layers were separated. The aqueous layer was further extracted with DCM (3×150 mL). The organic extracts were combined, washed with brine (250 mL), dried over Na$_2$SO$_4$, and concentrated under reduced pressure. The residue was purified by chromatography on silica gel (25% EtOAc in hexanes) to afford 4 (9.442 g, 89%) as a crystalline white solid.

$^1$H NMR (400 MHZ, CDCl$_3$) δ=8.34 (s, 1H), 7.96 (s, 1H), 3.59-3.42 (m, 2H), 3.36-3.18 (m, 2H), 1.28-1.10 (m, 6H) ppm. $^{13}$C NMR (100 MHz, CDCl$_3$) δ=166.0, 151.5, 145.3, 140.7, 133.0, 120.5, 43.6, 39.9, 14.4, 12.9 ppm. LRMS (ES$^+$) m/z [M+H]$^+$ calcd for C$_{10}$H$_{13}$BrClN$_2$O$^+$ 290.99; Found 291.00. IR (diamond, ATR) ν 2974, 2935, 1627, 1574 cm$^{-1}$.

diethyl 2-(3-bromo-5-(diethylcarbamoyl)pyridin-2-yl)malonate (6)

4

5

6

To a vigorously stirred mixture of 4 (5.000 g, 17.243 mmol, 1.0 equiv) and NaI (20.676 g, 137.94 mmol, 8.0 equiv) in acetonitrile (40 mL) was added TMSCl (3.28 mL, 25.86 mmol, 1.5 equiv) slowly. The mixture was stirred at ambient temperature for 30 min, then heated at reflux for 1 hour, with ¼ of the reaction volume removed and collected in a Dean-Stark receiver during this time period. The resulting yellow suspension was cooled to ambient temperature, diluted with DCM (150 mL), and added to a saturated aqueous NaHCO$_3$ solution (250 mL). With vigorous stirring, a saturated aqueous Na$_2$S$_2$O$_3$ solution (100 mL) was added, followed by 1M NaOH (80 mL). The resultant clear solution was transferred to a separatory funnel and the layers were separated. The aqueous layer was further extracted with DCM (3×100 mL). The organic extracts were combined, washed with brine (200 mL), dried over Na$_2$SO$_4$, and concentrated under reduced pressure.

The resulting pale orange solid was added to a sealable screw cap flask along with copper(I) iodide (0.164 g, 0.861 mmol. 0.05 equiv), picolinic acid (0.212 g, 1.72 mmol, 0.1 equiv), and Cs$_2$CO$_3$ (16.854 g, 51.729 mmol, 3.0 equiv). 1,4-dioxane (43 mL) and diethyl malonate (5.26 mL, 34.5 mmol, 2.0 equiv) were added, and the flask capped. The mixture was stirred and heated at 90° C. for 16 h. The mixture was cooled to ambient temperature and filtered over celite, and the filter cake was washed with EtOAc (200 mL). The filtrate was added to H$_2$O (500 mL), then 1M HCl (10 mL) was added and the layers were separated. The aqueous layer was further extracted with EtOAc (2×200 mL). The organic extracts were combined, washed with brine (250 mL), dried over Na$_2$SO$_4$, and concentrated under reduced pressure. The residue was purified by chromatography on silica gel (20% EtOAc in hexanes to 50% EtOAc in hexanes) to afford 6 (5.461 g, 76%) as a pale yellow oil.

US 12,637,464 B2

43

<sup>1</sup>H NMR (400 MHZ, CDCl₃) δ=8.52 (d, J=1.8 Hz, 1H), 7.92 (d, J=1.8 Hz, 1H), 5.22 (s, 1H), 4.34-4.23 (m, 4H), 3.62-3.44 (m, 2H), 3.38-3.19 (m, 2H), 1.32-1.10 (m, 12H) ppm. ¹³C NMR (100 MHZ, CDCl₃) δ=166.62, 166.58, 152.5, 142.2, 138.9, 133.5, 121.9, 62.3, 59.9, 43.6, 39.8, 14.5, 14.1, 12.9 ppm. LRMS (ES⁺) m/z [M+H]⁺ calcd for C₁₇H₂₄BrN₂O₅⁺ 415.09; Found 415.19. IR (diamond, ATR) v 2980, 2937, 1735, 1631 cm⁻¹.

3-bromo-5-(diethylcarbamoyl)-2-methylpyridine 1-oxide (8)

To a solution of 6 (5.350 g, 12.92 mmol, 1.0 equiv) in MeOH (130 mL) was added 2M aq. NaOH (32 mL), and the solution was stirred and heated at 50° C. for 16 h. To the resulting suspension, 1M aq. Citric acid (45 mL) was added to adjust the pH to 4, and the solution was stirred and heated at 60° C. for 24 h. The solution was cooled to ambient temperature and the MeOH was removed by concentration under reduced pressure. The solution was added to H₂O (250 mL) and extracted with DCM (3×200 mL). The organic layers were combined, washed with brine (250 mL), dried over Na₂SO₄, and concentrated under reduced pressure.

To a 0° C. cooled solution of the resulting residue in DCM (50 mL) was added MCPBA (70-75% balance) (5.946 g, 25.84 mmol, 2.0 equiv) slowly. The solution was warmed to ambient temperature and stirred for 22 h. The solution was added to 150 mL 1M NaOH and the layers were separated. The aqueous layer was further extracted with 10% isopropyl alcohol in DCM (3×100 mL). The organic extracts were combined, dried over Na₂SO₄, filtered, and concentrated under reduced pressure. The residue was purified by column chromatography on silica gel (EtOAc then 10% MeOH in EtOAc) to afford 8 (3.469 g, 94%) as a white solid.

<sup>1</sup>H NMR (400 MHZ, CDCl₃) δ=8.19 (d, J=0.9 Hz, 1H), 7.4 (d, J=0.9 Hz, 1H), 3.58-3.39 (m, 2H), 3.36-3.18 (m, 2H), 2.66 (s, 3H), 1.24-1.10 (m, 6H) ppm. ¹³C NMR (100 MHZ, CDCl₃) δ=164.6, 150.2, 136.2, 133.0, 127.0, 122.1, 43.5, 39.9, 17.4, 14.4, 12.8 ppm. LRMS (ES⁺) m/z [M+H]⁺ calcd for C₁₁H₁₆BrN₂O₂⁺ 287.04; Found 287.12. IR (diamond, ATR) v 3455, 2972, 2935, 1632 cm⁻¹.

5-bromo-N,N-diethyl-6-(hydroxymethyl)nicotinamide (9)

To a 0° C. cooled solution of 8 (1.301 g, 4.531 mmol, 1.0 equiv) in DCM (22.6 mL) was added trifluoroacetic anhydride (1.57 mL, 11.3 mmol, 2.5 equiv) dropwise. The solution was warmed to ambient temperature and stirred for 4 h before concentrating under reduced pressure. The residue was re-dissolved in DCM (22.6 mL) and 2M aq. Na₂CO₃ (45.2 mL) was added. The biphasic solution was stirred vigorously at ambient temperature for 18 h, then poured into H₂O (100 mL). The layers were separated and the aqueous layer was further extracted with DCM (3×50 mL). The organic extracts were combined, washed with brine (100 mL), dried over Na₂SO₄, and concentrated under reduced pressure. The residue was purified by column chromatography on silica gel (EtOAc) to afford 9 (1.119 g, 86%) as a yellow oil.

<sup>1</sup>H NMR (400 MHZ, CDCl₃) δ=8.53 (d, J=1.7 Hz, 1H), 7.90 (d, J=1.7 Hz, 1H), 4.77 (d, J=4.7 Hz, 2H), 4.23 (t, J=4.7 Hz, 1H), 3.64-3.46 (m, 2H), 3.38-3.18 (m, 2H), 1.32-1.08 (m, 6H) ppm. ¹³C NMR (100 MHZ, CDCl₃) δ=166.8, 157.6, 144.1, 138.6, 133.2, 118.7, 63.4, 43.6, 39.9, 14.5, 12.9 ppm. LRMS (ES⁺) m/z [M+H]⁺ calcd for C₁₁H₁₆BrN₂O₂ 287.04; Found 287.12. IR (diamond, ATR) v 3412, 2972, 2934, 1624, 1588 cm⁻¹.

5-bromo-N,N-diethyl-6-(hydroxymethyl)-1-methyl-1,2,3,6-tetrahydropyridine-3-carboxamide (10, Major Diastereomer)

5-bromo-N,N-diethyl-6-(hydroxymethyl)-1-methyl-1,2,3,6-tetrahydropyridine-3-carboxamide (11, Minor Diastereomer)

1. MeI MeCN, 70° C.

2. NaCNBH₃ AcOH, MeOH 0° C. to RT 10 (major), 11 (minor)
[5:2 dr; inseparable]

To a solution of 9 (0.980 g, 3.413 mmol, 1.0 equiv) in MeCN (4.25 mL) in a vial was added MeI (1.28 mL, 20.5 mmol, 6.0 equiv). The vial was capped and the solution was heated with stirring at 70° C. for 24 h then subsequently cooled to ambient temperature. To the mixture was added EtOAc (8.5 mL) followed by hexanes (8.5 mL) with vigorous stirring. The suspension was cooled to 0° C., filtered, and washed with hexanes (2×5 mL). The resulting yellow solid was dried under reduced pressure and used directly in the next step.

To a 0° C. cooled solution of the resulting methyl pyridinium salt (1.285 g, 2.995 mmol, 1.0 equiv) in MeOH (30 mL) was added AcOH (0.51 mL, 8.9 mmol, 3.0 equiv) followed by the dropwise addition of NaCNBH₃ (0.565 g, 8.98 mmol, 3.0 equiv) in MeOH (6 mL). The solution was warmed to ambient temperature and stirred for 16 h, then concentrated under reduced pressure. The residue was dissolved in EtOAc (100 mL) and added to 1M NaOH (200 mL). The layers were separated, and the aqueous layer was further extracted with EtOAc (3×100 mL). The organic extracts were combined and washed with brine (150 mL), dried over Na₂SO₄, and concentrated under reduced pressure. The residue was purified by column chromatography on silica gel (3% MeOH in DCM) to afford an inseparable mixture of diastereomers 10 (major diastereomer) and 11 (minor diastereomer) (0.726 g, 70%), 5:2 dr) as a pale yellow oil.

¹H NMR (400 MHZ, CDCl₃) δ=6.21† (s, 1H), 6.11* (d, J=2.8 Hz, 0.4H), 3.94† (dd, J=2.0 Hz, 1H), 3.88-3.78 (m, 1.4H), 3.70-3.64* (m, 0.4H), 3.59* (dd, J=8.8, 11.6 Hz, 0.4H), 3.54-3.47† (m, 1H), 3.34 (quint, J=7.3 Hz, 5.6H), 3.21* (dd, J=9.4, 13.6 Hz, 0.4H), 3.14-3.08* (m, 0.4H), 3.02-2.92† (m, 2H), 2.88-2.80† (m, 1H), 2.76* (dd, J=5.1, 14 Hz, 0.4H), 2.55* (s, 1.2H), 2.45† (s, 3H), 2.24-2.14 (m, 4.2H), 1.09 (t, J=7.1 Hz, 4.2H) ppm. ¹³C NMR (100 MHZ, CDCl₃) δ=170.22, 170.15, 130.4, 127.6, 123.3, 122.9, 68.6, 67.6, 60.9, 59.6, 53.6, 47.0, 43.5, 42.9, 42.2, 42.1, 41.3, 40.7, 40.4, 36.7, 15.1, 14.9, 13.2, 13.1 ppm. LRMS (ES⁺) m/z [M+H]⁺ calcd for C₁₂H₂₂BrN₂O₂⁺ 305.09; Found 305.14. IR (diamond, ATR) v 3418, 2970, 2934, 2799, 1629 cm⁻¹.

†denotes ¹H NMR signal arising exclusively from the major diastereomer; * denotes ¹H NMR signal arising exclusively from the minor diastereomer; undesignated signals arise from a mixture of both.

N,N-diethyl-6-(hydroxymethyl)-5-(1H-indol-7-yl)-1-methyl-1,2,3,6-tetrahydropyridine-3-carboxamide (12, Major Diastereomer, Assigned Anti Stereochemistry Based on the Crystal Structure of 16)

N,N-diethyl-6-(hydroxymethyl)-5-(1H-indol-7-yl)-1-methyl-1,2,3,6-tetrahydropyridine-3-carboxamide (13, Minor Diastereomer, Assigned Syn Stereochemistry Based on the Assignment of 12)

10 (major), 11 (minor)
[5:2 dr; inseparable]

Pd(PPh₃)₄
2M Na₂CO₃
1,4-dioxane
100° C.

12 (major)

+

13 (minor)

A mixture of diastereomers 10 and 11 (5:2 dr) (0.698 g, 2.29 mmol, 1.0 equiv), 1,4-dioxane (22.9 mL), indole-7-boronic acid pinacol ester (0.834 g, 3.43 mmol, 1.5 equiv), and 2M aq. Na₂CO₃ (2.29 mL) were added to a vial and the solution was sparged with N₂ for 10 min before the addition of Pd(PPh₃)₄ (0.132 g, 0.114 mmol, 0.05 equiv). The vial was capped and the mixture was heated with stirring at 100° C. in a preheated oil bath for 4 h. The mixture was cooled to ambient temperature, added to H₂O (400 mL), and extracted with EtOAc (3×150 mL). The organic extracts were combined, washed with brine (200 mL), dried over $Na_2SO_4$, and concentrated under reduced pressure. The residue was purified by column chromatography on silica gel (2% MeOH in DCM to 10% MeOH in DCM) to afford 12 (major diastereomer) (0.398 g, 51%) and 13 (minor diastereomer) (0.148 g, 19%) as off white semi-solids.

Major Diastereomer, 12. $^1$H NMR (400 MHZ, CDCl$_3$) δ=9.46 (s, 1H), 7.56 (d, J=7.8 Hz, 1H), 7.22 (t, J=2.8 Hz, 1H), 7.06 (t, J=7.3 Hz, 1H), 7.00 (dd, J=0.9, 8.4 Hz, 1H), 6.53 (dd, J=2.1, 3.2 Hz, 1H), 5.92 (s, 1H), 3.79 (dd, J=3.0, 11.2 Hz, 1H), 3.74-3.66 (m, 1H), 3.50-3.28 (m, 5H), 3.26-3.08 (m, 3H), 3.07-2.96 (m, 1H), 2.52 (s, 2H), 1.23 (t, J=7.1 Hz, 3H), 1.10 (t, J=7.1 Hz, 3H) ppm. $^{13}$C NMR (100 MHZ, CDCl$_3$) δ=171.7, 137.3, 135.4, 128.11, 128.05, 124.9, 124.1, 121.4, 119.9, 119.4, 102.4, 66.8, 59.1, 54.0, 43.2, 42.0, 40.3, 39.3, 14.9, 13.1 ppm. LRMS (ES$^+$) m/z [M+H]$^+$ calcd for $C_{20}H_{28}N_3O_2^+$ 342.22; Found 342.32. IR (diamond, ATR) v 3267, 2970, 2932, 1615 cm$^{-1}$.

Minor Diastereomer, 13. $^1$H NMR (400 MHZ, CDCl$_3$) δ=9.86 (s, 1H), 7.55 (d, J=7.8 Hz, 1H), 7.29-7.24 (m, 1H), 7.07 (t, J=7.4 Hz, 1H), 6.98 (dd, J=0.6, 7.6 Hz, 1H), 6.51 (dd, J=2.1 Hz, 3.2 Hz, 1H), 6.08-6.04 (m, 1H0, 3.76-3.68 (m, 1H), 3.64-3.28 (m, 8H), 3.15-3.06 (m 1H), 2.99 (dd, J=5.7, 13.2 Hz, 1H), 2.66 (s, 3H), 1.26 (t, J=7.2 Hz, 3H), 1.17 (t, J=7.1 Hz, 3H) ppm. $^{13}$C NMR (100 MHz, CDCl$_3$) δ=173.0, 135.7, 135.0, 128.4, 125.6, 125.4, 123.8, 120.0, 119.4, 119.0, 102.1, 64.8, 60.9, 48.6, 42.7, 42.3, 40.6, 34.8, 15.1, 13.3 ppm. LRMS (ES$^+$) m/z [M+H]$^+$ calcd for $C_{20}H_{28}N_3O_2^+$ 342.22; Found 342.32. IR (diamond, ATR) v 3270, 2973, 2934, 1613 cm$^{-1}$.

N,N-diethyl-8-methyl-7a,8,9,10-tetrahydro-7H-indolo[7,1-fg][1,7]naphthyridine-10-carboxamide (14, (±)-JRT)

12

14

To a 0° C. cooled solution of 12 (0.250 g, 0.732 mmol, 1.0 equiv) in CHCl$_3$ (7.3 mL) was added freshly crushed NaOH (0.234 g, 5.86 mmol, 8.0 equiv). A solution of TsCl (0.167 g, 0.878 mmol, 1.2 equiv) in CHCl$_3$ (1.5 mL) was added dropwise over 10 minutes. The mixture was warmed to ambient temperature and stirred for 1.5 h. The mixture was cooled to 0° C., and DMSO (3.7 mL) was added slowly before warming to ambient temperature and stirring for 1 h. The mixture was partitioned in H$_2$O (250 mL) and EtOAc (200 mL) and the layers were separated. The aqueous layer was further extracted with EtOAc (3×100 mL). The organic extracts were combined, washed with brine (250 mL), dried over Na$_2$SO$_4$, and concentrated under reduced pressure. The residue was purified by column chromatography on silica gel (8% MeOH in EtOAc to 12% MeOH in EtOAc) to afford 14 (0.168 g, 71%) as an off white semi-solid.

$^1$H NMR (400 MHZ, CDCl$_3$) δ=7.5 (d, J=7.9 Hz, 1H), 7.31 (d, J=7.3 Hz, 1H), 7.08-7.04 (m, 2H), 6.46 (d, J=3.0 Hz, 1H), 6.31 (s, 1H), 4.66 (dd, J=5.4, 11.2 Hz, 1H), 3.90-3.82 (m, 1H), 3.80 (t, J=11.1 Hz, 1H), 3.54-3.40 (m, 5H), 3.05 (dd, J=5.0, 11.2 Hz, 1H), 2.95 (t, J=10.7 Hz, 1H), 2.59 (s, 3H), 1.26 (t, J=7.1 Hz, 3H), 1.18 (t, J=7.1 Hz, 3H) ppm. $^{13}$C NMR (100 MHz, CDCl$_3$) δ=171.2, 133.2, 132.5, 126.3, 126.2, 120.3, 120.0, 118.91, 118.88, 114.9, 101.3, 60.5, 55.8, 48.0, 44.0, 42.1, 40.3, 39.9, 15.0, 13.2 ppm. LRMS (ES$^+$) m/z [M+H]$^+$ calcd for $C_{20}H_{26}N_3O^+$ 324.21; Found 324.29. IR (diamond, ATR) v 2972, 2869, 2798, 1636 cm$^{-1}$.

Example 2: Preparation of N,N-diethyl-8-methyl-7a,8,9,10-tetrahydro-7H-indolo[7,1-fg][1,7]naphthyridine-10-carboxamide (15, Minor Diastereomer)

13

15

To a 0° C. cooled solution of 13 (0.130 g, 0.381 mmol, 1.0 equiv) in CHCl$_3$ (3.8 mL) was added freshly crushed NaOH (0.122 g, 3.05 mmol, 8.0 equiv). A solution of TsCl (0.087 g, 0.46 mmol, 1.2 equiv) in CHCl$_3$ (0.76 mL) was added dropwise over 10 minutes. The mixture was warmed to ambient temperature and stirred for 1.5 h. The mixture was cooled to 0° C., and DMSO (1.9 mL) was added slowly before warming to ambient temperature and stirring for 3 h. The mixture was partitioned in H$_2$O (200 mL) and EtOAc (150 mL) and the layers were separated. The aqueous layer was further extracted with EtOAc (3×50 mL). The organic extracts were combined, washed with brine (100 mL), dried over Na$_2$SO$_4$, and concentrated under reduced pressure. The residue was purified by column chromatography on silica gel 8% MeOH in EtOAc to 12% MeOH in EtOAc) to afford 15 (0.044 g, 36%) as a brown semi-solid.

$^1$H NMR (400 MHZ, CDCl$_3$) δ=7.48 (d, J=7.9 Hz, 1H), 7.22 (d, J=7.2 Hz, 1H), 7.08-7.02 (m, 2H), 6.45 (d, J=3.0 Hz, 1H), 6.37 (dd, J=2.0, 3.6 Hz, 1H), 4.50 (dd, J=5.5, 11.2 Hz, 1H), 4.02 (t, J=11.2 Hz, 1H), 3.66-3.60 (m, 1H), 3.56-3.30 (m, 5H), 3.15 (dd, J=5.7, 12.2 Hz, 1H), 2.83 (dd, J=4.8, 12.2 Hz, 1H), 2.62 (s, 3H), 1.27 (t, J=7.0 Hz, 3H), 1.13 (t, J=7.0 Hz, 3H) ppm. $^{13}$C NMR (100 MHz, CDCl) δ=171.5, 133.4, 133.4, 126.5, 126.2, 120.4, 120.1, 119.9, 118.9, 114.2, 101.2, 58.6, 52.5, 47.9, 43.6, 42.0, 40.3, 37.4, 15.0, 13.2 ppm. LRMS (ES$^+$) m/z [M+H]$^+$ calcd for C$_{20}$H$_{26}$N$_3$O$^+$ 324.21; Found 324.29. IR (diamond, ATR) v 2969, 2932, 2871, 2791, 1634 cm$^{-1}$.

Example 3: Thermodynamic Equilibrium 14      15

[1:2]

14      15

[5:1]

Figure 7:
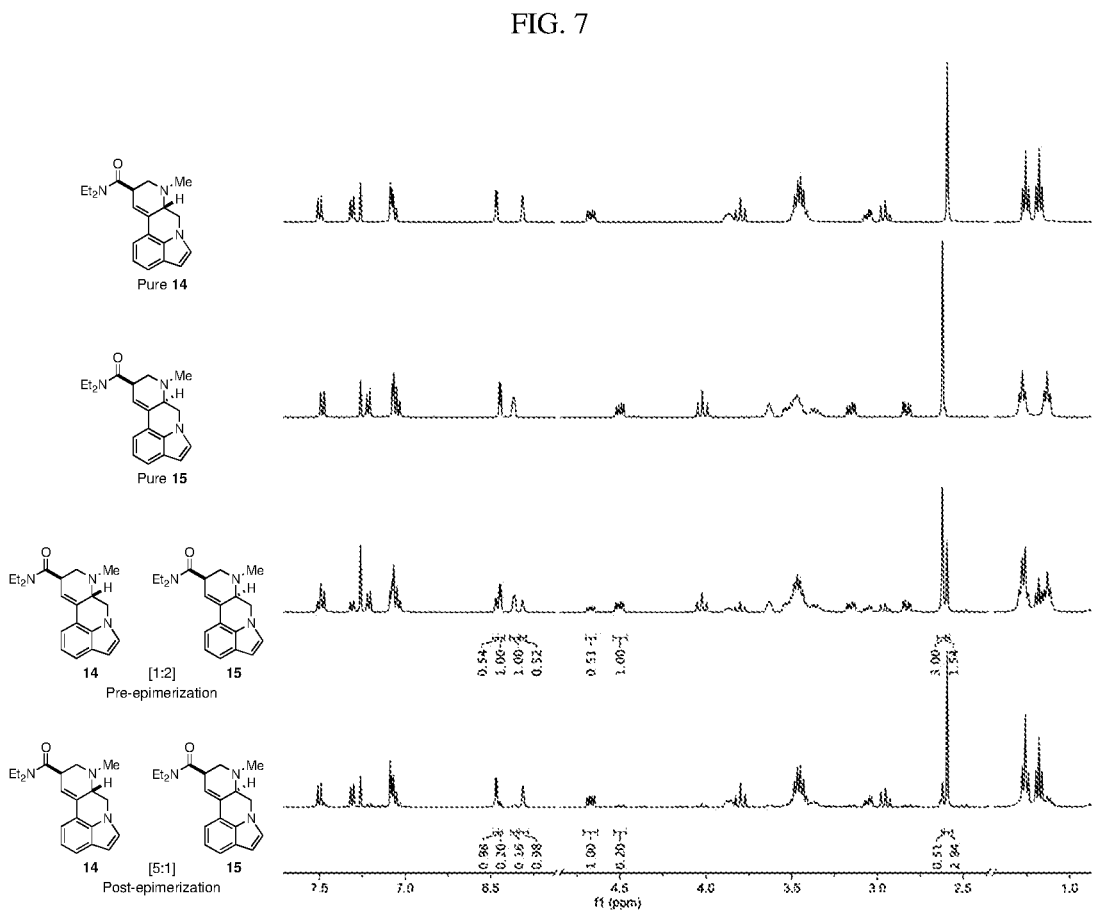
FIG. 7 shows NMR for the thermodynamic equilibrium of compounds 14 and 15.
Figure 8:
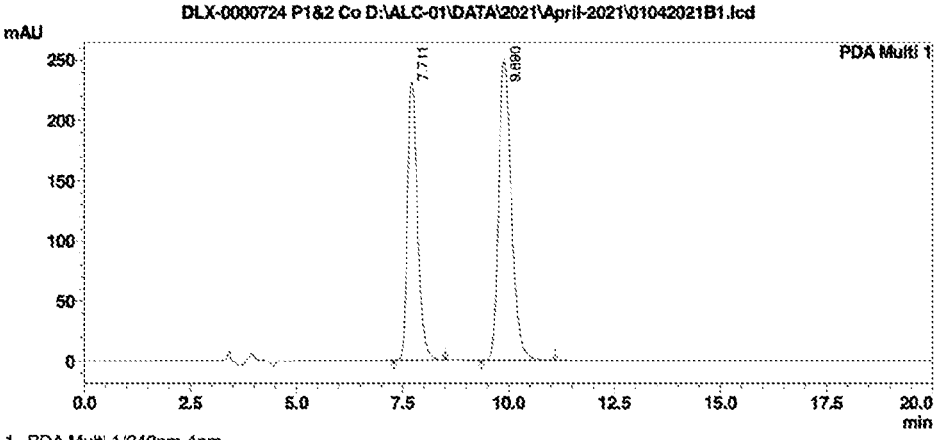
FIG. 8 shows the chiral HPLC graph for (±)-JRT.

To a solution of diastereomers 14 and 15 (1:2 ratio, measured via $^1$H NMR analysis) (0.014 g, 0.043 mmol, 1.0 equiv) in MeOH (1 mL) was added 2M aq. NaOH (0.5 mL). The solution was heated at 60° C. for 1 h and then concentrated under reduced pressure. The mixture was partitioned in H$_2$O (20 mL) and DCM (10 mL) and the layers were separated. The aqueous layer was further extracted with DCM (2×10 mL). The organic extracts were combined, washed with brine (20 mL), dried over Na$_2$SO$_4$, and concentrated under reduced pressure. Diastereomers 14 and 15 were obtained as a 5:1 mixture (measured via $^1$H NMR analysis), with 14 as the major diastereomer and 15 as the minor diastereomer, indicating 14 as the thermodynamically favored product. See FIG. 7.

Example 4: Fumarate Salt

14

(±)-JRT•Fumarate

To a solution of fumaric acid (0.051 g, 0.438 mmol, 1.05 equiv) in acetone (6 mL) stirring at 50° C. was added 14 (0.135 g, 0.417 mmol, 1.0 equiv.) in acetone (2 mL) slowly. The solution was cooled to room temperature slowly with stirring, and hexanes (15 mL) was added slowly. The suspension was cooled to 0° C. for 1 hour and then subsequently in a −20° C. freezer overnight. The resulting mixture was filtered, washed with ice-cold 1:1 acetone/hexanes (2 mL) and dried in a vacuum oven at 50° C. to afford (+)-JRT·fumarate (1:1 salt, 0.126 g, 69%) as a beige solid. $^1$H NMR (400 MHZ, MeOD$_4$) δ=7.45 (d, J=7.8 Hz, 1H), 7.30 (d, J=7.3 Hz, 1H), 7.21 (d, J=3.1 Hz, 1H), 7.03 (t, J=7.6 Hz, 1H), 6.74 (s, 2H), 6.44 (d, J=3.04 Hz, 1H), 6.36 (s, 1H), 4.94-4.86 (m, 1H), 4.08-4.00 (m, 1H), 3.80 (t, J=11.1 Hz, 1H), 3.72-3.65 (m, 1H), 3.56 (q, J=7.2 Hz, 2H), 3.45 (septet, J=7.6 Hz, 2H), 3.29-3.23 (m, 1H), 2.99 (t, J=11.1 Hz, 1H), 2.74 (s, 3H), 1.30 (t, J=7.1 Hz, 3H), 1.18 (t, J=7.1 Hz, 3H) ppm. $^{13}$C NMR (100 MHZ, MeOD$_4$) δ=173.0, 168.8, 135.4, 134.4, 133.1, 128.0, 127.8, 121.32, 121.26, 119.2, 119.1, 115.8, 102.4, 61.6, 56.4, 47.7, 43.8, 43.6, 42.0, 40.2, 15.1, 13.3 ppm. LRMS (ES$^+$) m/z [M+H]$^+$ calcd for C$_{20}$H$_{26}$N$_3$O$^+$ 324.21; Found 324.35. IR (diamond, ATR) v 2971, 2869, 2799, 1630 cm$^{-1}$.

Example 5: Chiral Separation of (+)-JRT and (−)-JRT

14

(+)-JRT (−)-JRT

Racemic (±)-JRT (14) was separated into its enantiomers by preparatory chiral HPLC using an Agilent 1260 Infinity II (Chiralpak-IC 250×30 mm, 5 μm; eluant: 50:50 mixture of 0.1% diethylamine in n-hexane (v/v) and 50% MeOH in $CH_2Cl_2$ (v/v); 35.0 mL/min).

Figure 9:
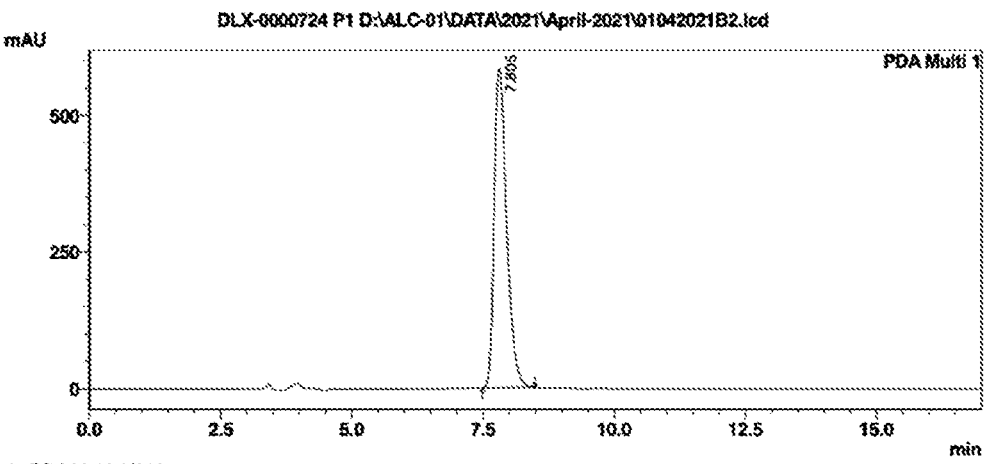
FIG. 9 shows the chiral HPLC graph for (−)-JRT.

First eluting peak, (−)-JRT. See FIG. 9. Analytical chiral HPLC $R_t$=7.81 min (Chiralpak-IC 250×4.6 mm, 5 μm; Eluant: 50:50 mixture of 0.1% DEA in n-hexane and isopropanol, 1.0 mL/min). 250 mg, Pale brown semisolid; LC-MS: m/z=324.1 [M+H]⁺.

(−)-JRT·Fumarate. In a sealed tube, fumaric acid (81 mg, 0.69 mmol, 1.0 equiv) in acetone (0.81 mL) was heated to 40° C. and stirred for 1 hr. To the resulting clear solution was added (−)-JRT (226 mg, 0.69 mmol, 1.0 equiv) dissolved in acetone (1.13 mL), and the mixture was stirred for 2 h at 40° C. After cooling to room temperature, the volatiles were evaporated to yield a residue which was triturated with diethyl ether followed by n-pentane to afford a pale brown semi solid, which was further lyophilized to yield 270 mg of (−)-JRT as the 1:1 fumarate salt (pale brown solid). The NMR data were consistent with those reported for (±)-JRT. Specific Rotation $[\alpha]_D^{20}$ −9.9 (c=0.0011 in ethanol).

Figure 10:
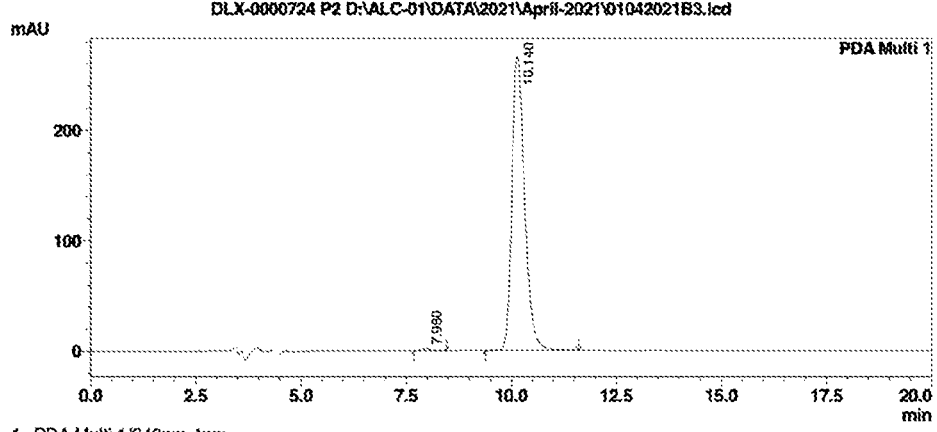
FIG. 10 shows the chiral HPLC graph for (+)-JRT.

Second eluting peak. See FIG. 10. Analytical chiral HPLC $R_t$=10.14 min (Chiralpak-IC 250×4.6 mm, 5 μm; Eluant: 50:50 mixture of 0.1% DEA in n-hexane and isopropanol, 1.0 mL/min). 290 mg, Pale brown semi solid; LC-MS: m/z=324.1 [M+H]⁺

(+)-JRT·Fumarate. In a sealed tube, fumaric acid (95 mg, 0.82 mmol, 1.0 equiv) was added to acetone (0.95 mL), heated to 40° C., and stirred for 1 hr. The resulting clear solution was treated with (+)-JRT (266 mg, 0.82 mmol, 1.0 equiv) dissolved in acetone (1.33 mL) and stirred for 2 hr at 40° C. After cooling to room temperature, the volatiles were evaporated to afford a residue which was triturated with diethyl ether followed by n-pentane to yield a pale brown solid, which was further lyophilized to yield 250 mg of (+)-JRT as the 1:1 fumarate salt (pale brown solid). The NMR data were consistent with those reported for (±)-JRT. Specific Rotation $[\alpha]_D^{20}$ +8.7 (c=0.0011 in ethanol).

Example 6: (7aS,10R)-10-(diethylcarbamoyl)-8,8-dimethyl-7a,8,9,10-tetrahydro-7H-indolo[7,1-fg][1,7]naphthyridin-8-ium iodide (16)

(±)-JRT·Fumarate

16

A mixture of (+)-JRT·fumarate (0.030 g), saturated aqueous $NaHCO_3$ (30 mL), and DCM (30 mL) was stirred vigorously for 20 min. The layers were separated, and the aqueous layer was further extracted with DCM (2×30 mL). The combined organic extracts were washed with brine (1×50 mL), dried over $Na_2SO_4$, and concentrated under reduced pressure. The resulting freebase was dissolved in DCM (4 mL), then methyl iodide (0.4 mL) was added, and the solution was stirred at ambient temperature for 14 hours in a 1 dram vial. Upon reaction completion, the stir bar was removed, and the 1 dram vial was placed inside of a 20 mL scintillation vial containing a solution of hexanes (5 mL) and $Et_2O$ (5 mL) as antisolvents for vapor diffusion. The two-chamber system was sealed by capping only the outer 20 mL scintillation vial and allowed to sit in the dark at ambient temperature for 1 month, with crystals suitable for x-ray diffraction analysis precipitating during this time. A single crystal was used for x-ray analysis, and the remainder was filtered and washed with ice-cold $Et_2O$ (1 mL) and dried in vacuo to afford 16 (0.019 g, 60%) as a light brown crystalline solid. ¹H NMR (400 MHZ, CDCl₃) δ=7.55 (d, J=7.0 Hz, 1H), 7.48 (d, J=7.5 Hz, 1H), 7.32 (d, J=2.9 Hz, 1H), 7.12 (t, J=7.7 Hz, 1H), 6.63 (s, 1H), 6.54 (d, J=3.0 Hz, 1H), 5.18-5.10 (m, 1H), 5.06-4.99 (m, 1H), 4.34-4.26 (m, 1H), 4.21 (t, J=11.3 Hz, 1H), 4.06 (t, J=11.4 Hz, 1H), 3.99-3.92 (m, 1H), 3.76-3.62 (m, 2H), 3.59 (s, 3H), 3.56-3.40 (m, 2H), 3.35 (s, 3H), 1.38 (t, J=3.1 Hz, 3H), 1.20 (t, J=3.1 Hz, 3H) ppm. LRMS (ES⁺) m/z [M]⁺ calcd for $C_{21}H_{28}N_3O^+$ 338.22; Found 338.45. IR (diamond, ATR) v 3456, 2971, 2932, 1633 cm⁻¹.

Example 7: X-Ray Crystallography

An orange block with approximate orthogonal dimensions 0.248×0.448×0.594 mm³ was placed and optically centered on the Bruker Duo APEXII CCD system at −183°
C. (90K). Indexing of the unit cell used a random set of
reflections collected from three series of 0.5° wide ω-scans,
10 seconds per frame, and 30 frames per series that were
well distributed in reciprocal space. Five ω-scan data frame
series were collected [MoK$_\alpha$] with 0.3° wide scans, 15
seconds per frame and 606 frames collected per series at
varying φ angles (φ=0°, 72°, 144°, 216°, 288°). The crystal
to detector distance was 5.15 cm, thus providing a complete
sphere of data to 2θ$_{max}$=61.40°.

TABLE 1

Crystal Data and Structure refinement for 16

| | |
|---|---|
| Empirical Formula | $C_{22}H_{30}Cl_2IN_3O$ |
| Formula Weight | 550.29 |
| Temperature | 90(2) K. |
| Wavelength | 0.71073 Å |
| Crystal System | Orthorhombic |
| Space Group | $P2_12_12_1$ |
| Unit Cell Dimensions | a = 7.0716(6) Å  $\alpha = 90°$ |
| | b = 14.4326(12) Å  $\beta = 90°$ |
| | c = 23.0876(19) Å  $\gamma = 90°$ |
| Volume | 2356.4(3) Å$^3$ |
| Z | 4 |
| $\rho_{calcd}$ | 1.551 g/cm$^3$ |
| Absorption Coefficient (μ) | 1.604 mm$^{-1}$ |
| F(000) | 1112 |
| Crystal Size | 0.594 × 0.448 × 0.248 mm |
| Crystal Color and Shape | Orange Block |
| Diffractometer | Bruker APEX-II CCD |
| θ Range for Data Collection | 1.664 to 30.735° |
| Index Ranges | −10 <= h <= 10, −20 <= k <= 20, −33 <= l <= 33 |
| Reflections Collected | 28854 |
| Independent Reflections | 7321 [R(int) = 0.0163] |
| Observed Reflections (I > 2σ(I)) | 7222 |
| Completeness to θ = 25.242° | 99.8% |
| Absorption Correction | Semi-empirical from equivalents |
| Max and Min. Transmission | 0.6095 and 0.4862 |
| Solution Method | SHELXT |
| Refinement Method | SHELXL-2018/3 Full-matrix least-squares on F$^2$ |
| Data/Restraints/Parameters | 7321/0/266 |
| Goodness-of-fit on F$^2$ | 1.081 |
| Final R Indices [I > 2σ(I)] | R1 = 0.0184, wR2 = 0.0493 |
| R Indices (all data) | R1 = 0.0189, wR2 = 0.0496 |
| Absolute Structure Parameters | Flaock = −0.014(3); Parsons = −0.013(3); Hooft = −0.013(2) |
| Largest Diff. Peak and Hole | 1.009 and −0.672e · Å$^{-3}$ |

TABLE 2

Non-hydrogen atomic coordinates (×10$^4$) and equivalent isotropic
displacement parameters (Å$^2$ × 10$^3$) for 16. U$_{eq}$ is defined
as one third of the trace of the orthogonalized U$^{ij}$ tensor.

| Label | x | y | z | U$_{eq}$ |
|---|---|---|---|---|
| C(1) | 7844(3) | 5098(1) | 6685(1) | 14(1) |
| C(2) | 7093(3) | 4697(1) | 7247(1) | 15(1) |
| N(2) | 6608(3) | 3678(1) | 7180(1) | 16(1) |
| C(3) | 4913(3) | 3611(1) | 6779(1) | 15(1) |
| C(4) | 5239(3) | 4172(1) | 6228(1) | 15(1) |
| C(5) | 6606(3) | 4811(1) | 6184(1) | 16(1) |
| C(6) | 4371(3) | 2587(1) | 6656(1) | 20(1) |
| N(6) | 2719(3) | 2616(1) | 6285(1) | 21(1) |
| C(7) | 1281(4) | 1975(2) | 6207(1) | 24(1) |
| C(8) | 240(4) | 2202(2) | 5728(1) | 26(1) |
| C(9) | 1056(3) | 3026(2) | 5484(1) | 22(1) |
| C(10) | 2603(3) | 3249(2) | 5844(1) | 19(1) |
| C(11) | 3804(3) | 4007(2) | 5774(1) | 17(1) |
| C(12) | 3393(3) | 4572(2) | 5301(1) | 21(1) |
| C(13) | 1868(4) | 4372(2) | 4928(1) | 25(1) |
| C(14) | 694(4) | 3612(2) | 5013(1) | 26(1) |

TABLE 2-continued

Non-hydrogen atomic coordinates (×10$^4$) and equivalent isotropic
displacement parameters (Å$^2$ × 10$^3$) for 16. U$_{eq}$ is defined
as one third of the trace of the orthogonalized U$^{ij}$ tensor.

| Label | x | y | z | U$_{eq}$ |
|---|---|---|---|---|
| C(15) | 8299(3) | 3145(2) | 6965(1) | 22(1) |
| C(16) | 6084(4) | 3316(2) | 7770(1) | 22(1) |
| C(17) | 7780(3) | 6165(1) | 6732(1) | 16(1) |
| N(17) | 8884(3) | 6659(1) | 6369(1) | 17(1) |
| O(17) | 6664(2) | 6533(1) | 7070(1) | 22(1) |
| C(18) | 10359(3) | 6288(2) | 5986(1) | 17(1) |
| C(19) | 12324(3) | 6395(2) | 6245(1) | 24(1) |
| C(20) | 8679(3) | 7674(2) | 6374(1) | 20(1) |
| C(21) | 7253(4) | 8000(2) | 5926(1) | 29(1) |
| I(31) | 8094(1) | 198(1) | 7065(1) | 19(1) |
| C(41) | 1778(4) | 9810(2) | 5726(1) | 29(1) |
| Cl(41) | 3738(1) | 10001(1) | 6186(1) | 30(1) |
| Cl(42) | 2063(1) | 8775(1) | 5312(1) | 32(1) |

TABLE 3

Hydrogen coordinates (×10$^4$) and isotropic displacement
parameters (Å$^2$ × 10$^3$) for 16.

| Label | x | y | z | U$_{eq}$ |
|---|---|---|---|---|
| H(1) | 9172 | 4886 | 6619 | 17 |
| H(2A) | 5949 | 5043 | 7366 | 18 |
| H(2B) | 8057 | 4771 | 7554 | 18 |
| H(3) | 3819 | 3900 | 6986 | 18 |
| H(5) | 6806 | 5098 | 5818 | 19 |
| H(6A) | 5425 | 2261 | 6461 | 23 |
| H(6B) | 4078 | 2260 | 7022 | 23 |
| H(7) | 1053 | 1456 | 6450 | 29 |
| H(8) | −827 | 1876 | 5584 | 31 |
| H(12) | 4155 | 5102 | 5229 | 25 |
| H(13) | 1636 | 4770 | 4608 | 29 |
| H(14) | −332 | 3493 | 4758 | 31 |
| H(15A) | 8074 | 2479 | 7015 | 33 |
| H(15B) | 9421 | 3327 | 7186 | 33 |
| H(15C) | 8502 | 3280 | 6554 | 33 |
| H(16A) | 5771 | 2656 | 7741 | 33 |
| H(16B) | 4987 | 3657 | 7917 | 33 |
| H(16C) | 7153 | 3397 | 8035 | 33 |
| H(18A) | 10309 | 6615 | 5610 | 21 |
| H(18B) | 10108 | 5623 | 5914 | 21 |
| H(19A) | 12585 | 7053 | 6313 | 36 |
| H(19B) | 13265 | 6143 | 5976 | 36 |
| H(19C) | 12389 | 6059 | 6613 | 36 |
| H(20A) | 9921 | 7963 | 6293 | 24 |
| H(20B) | 8266 | 7877 | 6763 | 24 |
| H(21A) | 7679 | 7818 | 5539 | 43 |
| H(21B) | 7138 | 8676 | 5945 | 43 |
| H(21C) | 6020 | 7717 | 6006 | 43 |
| H(41A) | 1633 | 10344 | 5461 | 35 |
| H(41B) | 614 | 9763 | 5963 | 35 |

Structural determination and Refinement. All crystallo-
graphic calculations were performed on a Surface Pro7 with
Intel i7-1065G7 at 1.30 GHz with four cores, eight proces-
sors and 16 GB of extended memory. Data collected were
corrected for Lorentz and polarization effects with Saint and
absorption using Blessing's method and merged as incor-
porated with the program Sadabs. The SHELXTL program
package was implemented to determine the probable space
group and set up the initial files. System symmetry, system-
atic absences and intensity statistics indicated the non-
centrosymmetric orthorhombic space group $P2_12_12_1$ (no.
19). The structure was determined by direct methods with
the molecule being located using the program XT. The
structure was refined with XL. The 48297 data collected
were merged based upon identical indices to 28854, then
merged for least squares refinement to 7321 unique data

[R(int)=0.0163]. All non-hydrogen atoms were refined anisotropically. Hydrogen atoms were idealized throughout the final refinement stages. The final structure was refined to convergence with $R(F)=1.89\%$, $wR(F^2)=4.96\%$, $GOF=1.081$ for all 7321 unique reflections [$R(F)=1.84$, $wR(F^2)=4.93$ for those 7222 data with $Fo>4\sigma(Fo)$]. The final difference-Fourier map was featureless indicating that the structure is both correct and complete. An empirical correction for extinction was also attempted and found to be negative and therefore not applied. The structure's absolute structure parameters were determined to be: Flack(x), −0.014(3); Hooft(y), −0.013(2) and the Parsons(z), −0.013 (3) indicating that the structure's absolute configuration has been determined reliably; these values would be close to 1.0 if the structure were inverted.

Example 8: Serotonin Assays

Serotonin 5-HT$_{2A}$ In Vitro Radioligand Binding Competition Assay. The 5-HT2A radioligand binding competition assay was performed at Epics Therapeutics S.A. (Belgium, FAST-0505B) using conventional methods. Briefly, competition binding is performed in duplicate in the wells of a 96 well plate (Master Block, Greiner, 786201) containing binding buffer (optimized for each receptor), membrane extracts (amount of protein/well optimized for each receptor), radiotracer [$^3$H]-DOI (final concentration optimized for each receptor) and test compound. Nonspecific binding is determined by co-incubation with 200-fold excess of cold competitor. The samples are incubated in a final volume of 0.1 ml at a temperature and for a duration optimized for each receptor and then filtered over filter plates. Filters are washed six times with 0.5 ml of ice-cold washing buffer (optimized for each receptor) and 50 µl of Microscint 20 (Packard) are added in each well. The plates are incubated 15 min on an orbital shaker and then counted with a TopCount™ for 1 min/well.

Serotonin 5-HT2A In Vitro Cellular IPOne Agonism Assay. The 5-HT2A IPOne HTRF assay was performed at Epics Therapeutics S.A. (Belgium, FAST-0505I) using conventional methods. Briefly, CHO-K1 cells expressing human recombinant 5-HT2A receptor grown to mid-log phase in culture media without antibiotics were detached with PBS-EDTA, centrifuged, and resuspended in medium without antibiotics buffer. 20,000 cells are distributed in a 96 well plate and incubated overnight at 37° C. with 5% $CO_2$.

For agonist testing, the medium is removed and 20 µl of assay buffer plus 20 µl of test compound or reference agonist are added in each well. The plate is incubated for 60 min. at 37° C. with 5% $CO_2$.

After addition of the lysis buffer containing IP1-d2 and anti-IP1 cryptate detection reagents, plates are incubated 1-hour at room temperature, and fluorescence ratios are measured according to the manufacturer specification, with the HTRF kit.

Serotonin 5-HT2C In Vitro Radioligand Binding Competition Assay. The 5-HT2Cedited (accession number AAF35842.1) radioligand binding competition assay was performed at Epics Therapeutics S.A. (Belgium, FAST-0507B) using conventional methods. Briefly, competition binding is performed in duplicate in the wells of a 96 well plate (Master Block, Greiner, 786201) containing binding buffer (optimized for each receptor), membrane extracts (amount of protein/well optimized for each receptor), radiotracer [$^3$H]-DOI (final concentration optimized for each receptor) and test compound. Nonspecific binding is determined by co-incubation with 200-fold excess of cold competitor. The samples are incubated in a final volume of 0.1 ml at a temperature and for a duration optimized for each receptor and then filtered over filter plates. Filters are washed six times with 0.5 ml of ice-cold washing buffer (optimized for each receptor) and 50 µl of Microscint 20 (Packard) are added in each well. The plates are incubated 15 min on an orbital shaker and then counted with a TopCount™ for 1 min/well.

Serotonin 5-HT2C In Vitro Cellular IPOne Agonism Assay. The 5-HT2C IPOne HTRF assay was performed at Epics Therapeutics S.A. (Belgium, FAST-0507I) using conventional methods. Briefly, CHO-K1 cells expressing human recombinant 5-HT2Cedited receptor (accession number AAF35842.1) grown to mid-log phase in culture media without antibiotics were detached with PBS-EDTA, centrifuged, and resuspended in medium without antibiotics buffer. 20,000 cells are distributed in a 96 well plate and incubated overnight at 37° C. with 5% $CO_2$.

For agonist testing, the medium is removed and 20 µl of assay buffer plus 20 µl of test compound or reference agonist are added in each well. The plate is incubated for 60 min. at 37° C. with 5% $CO_2$.

After addition of the lysis buffer containing IP1-d2 and anti-IP1 cryptate detection reagents, plates are incubated 1-hour at room temperature, and fluorescence ratios are measured according to the manufacturer specification, with the HTRF kit.

Example 9: Neurite Assays

Neurite Outgrowth in Primary Neuronal Cultures Assay. Changes in the pattern of neurite outgrowth have been implicated in psychiatric and neurodegenerative disorders as well as traumatic injuries. The discovery of new compounds that can positively affect neuritogenesis are important for developing new therapeutics for neurological diseases. Measurement of neurite outgrowth of rat cortical neurons using an automated image-based assay was used to determine the neuroplastic effects of the compounds of the present invention. The neurite outgrowth assay was performed at Neurofit SAS (France) as described below.

Pregnant Wistar rats (Janvier; France) were used for the study. They were delivered 6 days before their use. Upon arrival at Neurofit animal facility, they were housed one per cage and maintained in a room with controlled temperature (21-22° C.) and a reversed light-dark cycle (12 h/12 h; lights on: 17:30-05:30; lights off: 05:30-17:30) with food and water available ad libitum.

Female Wistar rats of 17 days gestation were killed by cervical dislocation and the fetuses were removed from the uterus. Their brains were placed in ice-cold medium of Leibovitz (L15, Gibco, Fisher bioblock, France). Cortices were dissected and meninges were carefully removed. The cortical neurons were dissociated by trypsinization for 30 min at 37° C. (trypsin-EDTA, Gibco) in presence of 0.1 mg/ml DNAse I (Roche, France). The reaction was stopped by addition of Dulbecco's Modified Eagle Medium (DMEM; Gibco) with 10% of fetal bovine serum (FBS; Gibco). The suspension was triturated with a 10-ml pipette and using a needle syringe 21G and centrifuged at 350×g for 10 min at room temperature. The pellet of dissociated cells was resuspended in a medium consisting of Neurobasal (Gibco) supplemented with 2% B27 supplement (Gibco), 0.5 mM L-Glutamine (Gibco), an antibiotic-antimicotic mixture. Viable cells were counted in a Neubauer cytometer using the trypan blue exclusion test (Sigma). Cells were seeded at a density of 10000 cells per well in 96-well plate (Costar) precoated with poly-L-lysine. Test compound at different concentrations were added to the cultures. Done-pezil (positive control) was tested at 250 nM.

After 72 h (3 days) of plating, cultures were fixed with paraformaldehyde in PBS (4%, Sigma) for 30 min at 4° C. Then, cells were successively permeabilized with 0.1% Triton X100 for 30 min, saturated with PBS containing 3% of BSA and were incubated 1 h with anti-beta III tubulin antibody (Sigma) at 1/10 000 in PBS containing 0.5% of BSA. Cells were washed three times with PBS containing 0.5% of BSA, and they were incubated 1 h with goat anti-mouse antibody coupled with AF488 (Invitrogen A11001) diluted at 1/1000 in PBS containing 0.5% of BSA. Finally, nuclei were staining with DAPI 1 mg/ml at 1/1000 in PBS containing 0.5% of BSA. After rinsing with PBS, the plate was filmed and neurite networks were examined and analyzed using High-Content Screening (CellInsight, Thermo Scientific). The average number of neurites per neuron and the average total length of neurites per neuron were the main parameters analyzed. Analysis of data was performed using analysis of variance (ANOVA). The Fisher's Protected Least Significant Difference test was used for multiple comparisons. A p value≤0.05 was considered significant. The software used is StatView 5.0 from SAS Institut.

In some embodiments, a compound of the present invention increases the pattern of neurite outgrowth. In some embodiments, a compound of the present invention increases neurite average length compared to a control. In some embodiments, a compound of the present invention increases neurite branch points compared to a control. In some embodiments, a compound of the present invention significantly increases the number of new neurites, and/or the average neurite length, and/or the total length of the dendritic arbor compared to a control.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A compound, or a pharmaceutically acceptable salt thereof, having a structure of Formula (K):

(K)

wherein:

each $R^{1a}$, $R^{1b}$, $R^{1c}$, and $R^{1d}$ is independently H, $C_{1-6}$ alkyl, $C_{2-6}$ alkenyl, $C_{2-6}$ alkynyl, $C_{1-6}$ alkoxy, $C_{1-6}$ alkoxyalkyl, halogen, $C_{1-6}$ haloalkyl, $C_{1-6}$ haloalkoxy, —$NO_2$, or —CN;

alternatively, two $R^{1a}$ groups on adjacent ring atoms are combined to form a $C_{4-8}$ cycloalkyl or 4 to 8 membered heterocycloalkyl having 1 to 2 heteroatoms, each independently N, O, or S;

$R^{2a}$ and $R^{2b}$ are each independently H, $C_{1-6}$ alkyl, $C_{3-6}$ cycloalkyl, $C_{1-6}$ alkoxy, $C_{1-6}$ alkoxyalkyl, $C_{1-6}$ haloalkyl, or $C_{1-6}$ haloalkoxy;

alternatively, $R^{2a}$ and $R^{2b}$ are combined to form a 4 to 8 membered heterocycloalkyl having 1 to 2 heteroatoms, each independently N, O, or S;

$R^3$ is H, $C_{1-6}$ alkyl, $C_{1-6}$ alkoxy, $C_{1-6}$ alkoxyalkyl, $C_{1-6}$ haloalkyl, or $C_{1-6}$ haloalkoxy;

$R^{3a}$ is absent or $C_{1-6}$ alkyl;

alternatively, $R^3$ and $R^{3a}$ are combined to form a 3 to 8 membered heterocycloalkyl having 1 to 2 heteroatoms, each independently N, O, or S;

subscripts m and p are each independently 0 to 2; and subscripts n and r are each independently 0 to 3.

2. The compound of claim 1, or a pharmaceutically acceptable salt thereof, having a structure of Formula (I):

(I)

3. The compound of claim 1, or a pharmaceutically acceptable salt thereof, having a structure of Formula (Ia), Formula (Ib), Formula (Ic), or Formula (Id):

(Ia)

(Ib)

-continued (Ic)

(Id)

4. The compound of claim 1, or a pharmaceutically acceptable salt thereof, wherein $R^{1a}$ is H, $C_{1-6}$ alkyl, $C_{1-6}$ alkoxy, or halogen.

5. The compound of claim 1, or a pharmaceutically acceptable salt thereof, wherein $R^{1a}$ is H.

6. The compound of claim 1, or a pharmaceutically acceptable salt thereof, wherein $R^{2a}$ and $R^{2b}$ are each independently H, $C_{1-6}$ alkyl, $C_{3-6}$ cycloalkyl, $C_{1-6}$ alkoxyalkyl, or $C_{1-6}$ haloalkyl.

7. The compound of claim 1, or a pharmaceutically acceptable salt thereof, wherein $R^{2a}$ and $R^{2b}$ are each independently $C_{1-6}$ alkyl.

8. The compound of claim 1, or a pharmaceutically acceptable salt thereof, wherein $R^{2a}$ and $R^{2b}$ are each independently ethyl.

9. The compound of claim 1, or a pharmaceutically acceptable salt thereof, wherein $R^3$ is H or $C_{1-6}$ alkyl.

10. The compound of claim 1, or a pharmaceutically acceptable salt thereof, wherein $R^3$ is methyl.

11. The compound of claim 1, or a pharmaceutically acceptable salt thereof, having the following structure:

12. The compound of claim 1, having the following structure:

-continued

13. The compound of claim 1, or a pharmaceutically acceptable salt thereof, having the following structure:

14. The compound of claim 1, having the following structure:

15. The compound of claim 1, having the following structure:

16. A crystalline compound of (7aS,10R)-10-(diethylcar-bamoyl)-8,8-dimethyl-7a,8,9,10-tetrahydro-7H-indolo[7,1-fg][1,7]naphthyridin-8-ium iodide having the following structure:

characterized by unit cell dimensions of a=7.0716(6) Å, α=90°, b=14.4326(12) Å, β=90°, c=23.0876(19) Å, and γ=90°.

17. A pharmaceutical composition, comprising a therapeutically effective amount of a compound of claim 1, or a pharmaceutically acceptable salt thereof.

18. A method for increasing neural plasticity, the method comprising contacting a neuronal cell with a compound of claim 1, or a pharmaceutically acceptable salt thereof, in an amount sufficient to increase neural plasticity of the neuronal cell, wherein the compound produces a maximum number of dendritic crossings with an increase of greater than 1.0 fold by a Sholl Analysis.

19. A method for increasing neural plasticity and increasing dendritic spine density, the method comprising contacting a neuronal cell with a compound of claim 1, or a pharmaceutically acceptable salt thereof, in an amount sufficient to increase neural plasticity and increase dendritic spine density of the neuronal cell.

\* \* \* \* \*